United States Patent
Angibaud et al.

(10) Patent No.: US 6,458,800 B1
(45) Date of Patent: Oct. 1, 2002

(54) 1,2-ANNELATED QUINOLINE DERIVATIVES

(75) Inventors: Patrick René Angibaud, Fontaine-Bellenger; Marc Gaston Venet, Le Mesnil-Esnard; Xavier Marc Bourdrez, Le Vaudreuil, all of (FR)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 09/868,992

(22) PCT Filed: Dec. 17, 1999

(86) PCT No.: PCT/EP99/10214

§ 371 (c)(1),
(2), (4) Date: Aug. 29, 2001

(87) PCT Pub. No.: WO00/39082

PCT Pub. Date: Jul. 6, 2000

(30) Foreign Application Priority Data

Dec. 23, 1998 (EP) .............................................. 98204444

(51) Int. Cl.[7] .................... C07D 471/04; C07D 487/04; A61K 31/4365; A61K 31/519; A61P 35/00
(52) U.S. Cl. ........................... 514/267; 546/82; 546/84; 514/293; 514/292; 544/251
(58) Field of Search ..................... 546/82, 84; 514/293, 514/292, 267; 544/251

(56) References Cited

FOREIGN PATENT DOCUMENTS

| EP | 0371564 | 6/1990 |
| WO | 97/16443 | 5/1997 |
| WO | 97/21701 | 6/1997 |
| WO | 98/40383 | 9/1998 |
| WO | 98/49157 | 11/1998 |

OTHER PUBLICATIONS

Kohl et al, "Selective Inhibition of ras–Dependent Transformation by a Farnesyltransferase Inhibitor", *Science*, 1993, 260, 1934–1937.

Rak, J. et al., "Mutant ras Oncogenes Upregulate VEGF/VPF Expression: Implications for Induction and Inhibition of Tumor Angiogenesis", *Cancer Res.*, 1995, 55, 4575–4580.

*Primary Examiner*—Richard L. Raymond
*Assistant Examiner*—Hong Liu
(74) *Attorney, Agent, or Firm*—Woodcock Washburn LLP

(57) ABSTRACT

This invention concerns compounds of formula

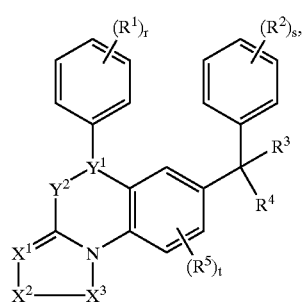

(I)

the pharmaceutically acceptable acid addition salts and the stereochemically isomeric forms thereof, wherein $=X^1-X^2-X^3-$ is a trivalent radical,; $>Y^1-Y^2-$ is a trivalent radical; r and s are each independently 0, 1, 2, 3, 4 or 5; t is 0, 1, 2 or 3; each $R^1$ and $R^2$ are independently hydroxy, halo, cyano, $C_{1-6}$alkyl, trihalomethyl, trihalomethoxy, $C_{2-6}$alkenyl, $C_{1-6}$alkyloxy, hydroxy$C_{1-6}$alkyloxy, $C_{1-6}$alkylthio, $C_{1-6}$alkyloxy$C_{1-6}$alkyloxy, $C_{1-6}$alkyloxycarbonyl, amino$C_{1-6}$alkyloxy, mono- or di($C_{1-6}$alkyl)amino, mono- or di($C_{1-6}$alkyl)amino$C_{1-6}$alkyloxy, aryl, aryl$C_{1-6}$alkyl, aryloxy or aryl$C_{1-6}$alkyloxy, hydroxycarbonyl, $C_{1-6}$alkyloxycarbonyl; or two $R^1$ or $R^2$ on adjacent positions form together a bivalent radical; $R^3$ is hydrogen, halo, $C_{1-6}$alkyl, cyano, halo$C_{1-6}$alkyl, hydroxy$C_{1-6}$alkyl, cyano$C_{1-6}$alkyl, amino$C_{1-6}$alkyl, $C_{1-6}$alkyloxy$C_{1-6}$alkyl, $C_{1-6}$alkylthio-$C_{1-6}$alkyl, aminocarbonyl$C_{1-6}$alkyl, hydroxycarbonyl, hydroxycarbonyl$C_{1-6}$alkyl, $C_{1-6}$alkyloxycarbonyl$C_{1-6}$alkyl, $C_{1-6}$alkylcarbonyl$C_{1-6}$alkyl, $C_{1-6}$alkyloxycarbonyl, aryl, aryl$C_{1-6}$alkyloxy$C_{1-6}$alkyl, mono- or di($C_{1-6}$alkyl)amino$C_{1-6}$alkyl, or a radical of formula $-O-R^{10}$, $-S-R^{10}$ or $-NR^{11}R^{12}$; $R^4$ is an optionally substituted imidazolyl; aryl is an optionally substituted phenyl or naphthalenyl; having farnesyl transferase and geranylgeranyl transferase inhibiting activity; their preparation, compositions containing them and their use as a medicine.

9 Claims, No Drawings

1,2-ANNELATED QUINOLINE DERIVATIVES

The present invention is concerned with novel 1,2-annelated quinoline derivatives, the preparation thereof, pharmaceutical compositions comprising said novel compounds and the use of these compounds as a medicine as well as methods of treatment by administering said compounds.

Oncogenes frequently encode protein components of signal transduction pathways which lead to stimulation of cell growth and mitogenesis. Oncogene expression in cultured cells leads to cellular transformation, characterized by the ability of cells to grow in soft agar and the growth of cells as dense foci lacking the contact inhibition exhibited by non-transformed cells. Mutation and/or overexpression of certain oncogenes is frequently associated with human cancer. A particular group of oncogenes is known as ras which have been identified in mammals, birds, insects, mollusks, plants, fungi and yeasts. The family of mammalian ras oncogenes consists of three major members ("isoforms"): H-ras, K-ras and N-ras oncogenes. These ras oncogenes code for highly related proteins generically known as $p21^{ras}$. Once attached to plasma membranes, the mutant or oncogenic forms of $p21^{ras}$ will provide a signal for the transformation and uncontrolled growth of malignant tumor cells. To acquire this transforming potential, the precursor of the $p_{21}^{ras}$ oncoprotein must undergo an enzymatically catalyzed farnesylation of the cysteine residue located in a carboxyl-terminal tetrapeptide. Therefore, inhibitors of the enzymes that catalyzes this modification, i.e. farnesyl transferase, will prevent the membrane attachment of $p_{21}^{ras}$ and block the aberrant growth of ras-transformed tumors. Hence, it is generally accepted in the art that farnesyl transferase inhibitors can be very useful as anticancer agents for tumors in which ras contributes to transformation.

The K-ras B isoform has been observed to be the dominant isoform which is mutated in human cancers, particular in colon (50% incidence) and pancreatic (90% incidence) cancers. However, it was also found that ras protein activation in the K-ras B isoform transformed cancers is resistant to inhibition of farnesyl transferase. The isoform confers resistance to farnesyl transferase inhibitors, but makes this isoform also substrate for geranylgeranyl transferase I. Therefore, inhibitors of geranylgeranyl transferase may inhibit the aberrant growth of K-ras transformed tumors which are resistant to farnesyl transferase inhibitors.

Since mutated oncogenic forms of ras are frequently found in many human cancers, most notably in more than 50% of colon and pancreatic carcinomas (Kohl et al., Science, vol 260, 1834–1837, 1993), it has been suggested that farnesyl tranferase inhibitors can be very useful against these types of cancer.

In EP-0,371,564 there are described (1H-azol-1-ylmethyl) substituted quinoline and quinolinone derivatives which suppress the plasma elimination of retinoic acids. Some of these compounds also have the ability to inhibit the formation of androgens from progestines and/or inhibit the action of the aromatase enzyme complex.

In WO 97/16443, WO 97/21701, WO 98/40383 and WO 98/49157, there are described 2-quinolone derivatives which exhibit farnesyl transferase inhibiting activity.

Unexpectedly, it has been found that the present novel 1,2-annelated quinoline compounds, bearing a nitrogen- or carbon-linked imidazole, show farnesyl protein transferase and geranylgeranyl transferase inhibiting activity.

The present invention concerns compounds of formula

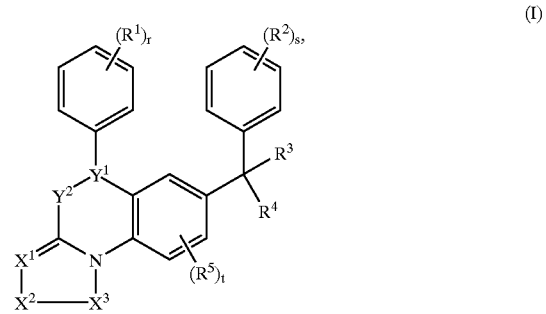

(I)

or the pharmaceutically acceptable acid addition salts and the stereochemically isomeric forms thereof, wherein
=X¹—X²—X³— is a trivalent radical of formula
=N—CR⁶=CR⁷— (x-1),
=N—N=CR⁶— (x-2),
=N—NH—C(=O)— (x-3),
=N—N=N— (x4),
=N—CR⁶=N— (x-5),
=CR⁶—CR⁷=CR⁸— (x-6),
=CR⁶—N=CR⁷— (x-7),
=CR⁶—NH—C(=O)— (x-8), or
=CR⁶—N=N— (x-9);
 wherein each R⁶, R⁷ and R8 are independently hydrogen, $C_{1-4}$alkyl, hydroxy, $C_{1-4}$alkyloxy, aryloxy, $C_{1-4}$alkyloxycarbonyl, hydroxy$C_{1-4}$alkyl, $C_{1-4}$alkyloxy$C_{1-4}$alkyl, mono- or di($C_{1-4}$alkyl)amino$C_{1-4}$alkyl, cyano, amino, thio, $C_{1-4}$alkylthio, arylthio or aryl;
>Y¹—Y²— is a trivalent radical of formula
 >CH—CHR⁹— (y-1),
 >C=N— (y-2),
 >CH—NR⁹— (y-3), or
 >C=CR⁹— (y-4);
 wherein each R⁹ independently is hydrogen, halo, halocarbonyl, aminocarbonyl, hydroxy$C_{1-4}$alkyl, cyano, carboxyl, $C_{1-4}$alkyl, $C_{1-4}$alkyloxy, $C_{1-4}$alkyloxy$C_{1-4}$alkyl, $C_{1-4}$alkyloxycarbonyl, mono- or di($C_{1-4}$alkyl)amino, mono- or di($C_{1-4}$alkyl)amino$C_{1-4}$alkyl, aryl;
r and s are each independently 0, 1, 2, 3, 4 or 5;
t is 0, 1, 2 or 3;
each R¹ and R² are independently hydroxy, halo, cyano, $C_{1-6}$alkyl trihalomethyl, trihalomethoxy, $C_{2-6}$alkenyl, $C_{1-6}$alkyloxy, hydroxy$C_{1-6}$alkyloxy, $C_{1-6}$alkylthio, $C_{1-6}$alkyloxy$C_{1-6}$alkyloxy, $C_{1-6}$alkyloxycarbonyl, amino$C_{1-6}$alkyloxy, mono- or di($C_{1-6}$alkyl)amino, mono- or di($C_{1-6}$alkyl)amino$C_{1-6}$alkyloxy, aryl, aryl$C_{1-6}$alkyl, aryloxy or aryl$C_{1-6}$alkyloxy, hydroxycarbonyl, $C_{1-6}$alkyloxycarbonyl, aminocarbonyl, amino$C_{1-6}$alkyl, mono- or di($C_{1-6}$alkyl)aminocarbonyl, mono- or di($C_{1-6}$alkyl)amino$C_{1-6}$alkyl; or
two R¹ or R² substituents adjacent to one another on the phenyl ring may independently form together a bivalent radical of formula
 —O—CH₂—O— (a-1),
 —O—CH₂—CH₂—O— (a-2),
 —O=CH=CH— (a-3),
 —O—CH₂—CH₂— (a-4),
 —O—CH₂—CH₂—CH₂— (a-5), or
 —CH=CH—CH=CH— (a-6);
R³ is hydrogen, halo, $C_{1-6}$alkyl, cyano, halo$C_{1-6}$alkyl, hydroxy$C_{1-6}$alkyl, cyano$C_{1-6}$alkyl, amino$C_{1-6}$alkyl, $C_{1-6}$alkyloxy$C_{1-6}$alkyl, $C_{1-6}$alkylthio$C_{1-6}$alkyl, aminocarbonyl$C_{1-6}$alkyl, hydroxycarbonyl, hydroxycarbonyl$C_{1-6}$alkyl, $C_{1-6}$alkyloxycarbonyl$C_{1-6}$alkyl, $C_{1-6}$alkylcarbonyl$C_{1-6}$alkyl, $C_{1-6}$alkyloxycarbonyl, aryl, aryl$C_{1-6}$alkyloxy$C_{1-6}$alkyl, mono- or di($C_{1-6}$alkyl)amino$C_{1-6}$alkyl;

or a radical of formula
—O—$R^{10}$ (b-1),
—S—$R^{10}$ (b-2),
—$NR^{11}R^{12}$ (b-3), wherein $R^{10}$ is hydrogen, $C_{1-6}$alkyl, $C_{1-6}$alkylcarbonyl, aryl, aryl$C_{1-6}$alkyl, $C_{1-6}$alkyloxycarbonyl$C_{1-6}$alkyl, or a radical of formula -Alk-$OR^3$ or -Alk—$NR^{14}R^{15}$;

$R^{11}$ is hydrogen, $C_{1-6}$alkyl, aryl or aryl$C_{1-6}$alkyl;

$R^{12}$ is hydrogen, $C_{1-6}$alkyl, aryl, hydroxy, amino, $C_{1-6}$alkyloxy, $C_{1-6}$alkylcarbonyl$C_{1-6}$alkyl, aryl$C_{1-6}$alkyl, $C_{1-6}$alkylcarbonylamino, mono- or di($C_{1-6}$alkyl)amino, $C_{1-6}$alkylcarbonyl, aminocarbonyl, arylcarbonyl, halo$C_{1-6}$alkylcarbonyl, aryl$C_{1-6}$alkylcarbonyl, $C_{1-6}$alkyloxycarbonyl, $C_{1-6}$alkyloxy$C_{1-6}$alkylcarbonyl, mono- or di($C_{1-6}$alkyl)aminocarbonyl wherein the alkyl moiety may optionally be substituted by one or more substituents independently selected from aryl or $C_{1-3}$alkyloxycarbonyl, aminocarbonylcarbonyl, mono- or di($C_{1-6}$alkyl)amino$C_{1-6}$alkylcarbonyl, or a radical or formula -Alk-$OR^{13}$ or -Alk—$NR^{14}R^{15}$;

wherein Alk is $C_{1-6}$alkanediyl;

$R^{13}$ is hydrogen, $C_{1-6}$alkyl, $C_{1-6}$alkylcarbonyl, hydroxy$C_{1-6}$alkyl, aryl or aryl$C_{1-6}$alkyl;

$R^{14}$ is hydrogen, $C_{1-6}$alkyl, aryl or aryl$C_{1-6}$alkyl;

$R^{15}$ is hydrogen, $C_{1-6}$alkyl, $C_{1-6}$alkylcarbonyl, aryl or aryl$C_{1-6}$alkyl;

$R^4$ is a radical of formula

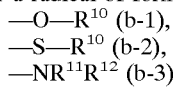 (c-1)

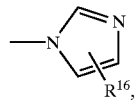 (c-2)

wherein $R^{16}$ is hydrogen, halo, aryl, $C_{1-6}$alkyl, hydroxy$C_{1-6}$alkyl, $C_{1-6}$alkyloxy$C_{1-6}$alkyl, $C_{1-6}$alkyloxy, $C_{1-6}$alkylthio, amino, mono- or di($C_{1-4}$alkyl)amino, hydroxycarbonyl, $C_{1-6}$alkyloxycarbonyl, $C_{1-6}$alkylthio$C_{1-6}$alkyl, $C_{1-6}$alkylS(O)$C_{1-6}$alkyl or $C_{1-6}$alkylS(O)$_2C_{1-6}$alkyl;

$R^{16}$ may also be bound to one of the nitrogen atoms in the imidazole ring of formula (c-1) or (c-2), in which case the meaning of $R^{16}$ when bound to the nitrogen is limited to hydrogen, aryl, $C_{1-6}$alkyl, hydroxy$C_{1-6}$alkyl, $C_{1-6}$alkyloxy$C_{1-6}$alkyl, $C_{1-6}$alkyloxycarbonyl, $C_{1-6}$alkylS(O)$C_{1-6}$alkyl or $C_{1-6}$alkylS(O)$_2C_{1-6}$alkyl;

R17 is hydrogen, $C_{1-6}$alkyl, $C_{1-6}$alkyloxy$C_{1-6}$alkyl, aryl$C_{1-6}$alkyl, trifluoromethyl or di($C_{1-4}$alkyl)aminosulfonyl;

$R^5$ is $C_{1-6}$alkyl, $C_{1-6}$alkyloxy or halo;

aryl is phenyl, naphthalenyl or phenyl substituted with 1 or more substituents each independently selected from halo, $C_{1-6}$alkyl, $C_{1-6}$alkyloxy or trifluoromethyl.

A special group of compounds contains those compounds of formula (I) wherein each $R^1$ and R2 are independently hydroxy, halo, cyano, $C_{1-6}$alkyl, trihalomethyl, trihalomethoxy, $C_{2-6}$alkenyl, $C_{1-6}$alkyloxy, hydroxy$C_{1-6}$alkyloxy, $C_{1-6}$alkylthio, $C_{1-6}$alkyloxy$C_{1-6}$alkyloxy, $C_{1-6}$alkyloxycarbonyl, amino$C_{1-6}$alkyloxy, mono- or di($C_{1-6}$alkyl)amino, mono- or di($C_{1-6}$alkyl)amino$C_{1-6}$alkyloxy, aryl, aryl$C_{1-6}$ alkyl, aryloxy or aryl$C_{1-6}$alkyloxy, hydroxycarbonyl, $C_{1-6}$alkyloxycarbonyl; or two $R^1$ or $R^2$ substituents adjacent to one another on the phenyl ring may independently form together a bivalent radical of formula
—O—$CH_2$—O— (a-1),
—O—$CH_2$—$CH_2$—O— (a-2),
—O=CH=CH— (a-3),
—O—$CH_2$—$CH_2$— (a-4),
—O—$CH_2$—$CH_2$—$CH_2$— (a-5), or
—CH=CH—CH=CH— (a-6);

$R^{16}$ is hydrogen, halo, aryl, $C_{1-6}$alkyl, hydroxy$C_{1-6}$alkyl, $C_{1-6}$alkyloxy$C_{1-6}$alkyl, $C_{1-6}$alkyloxy, $C_{1-6}$alkylthio, amino, mono- or di($C_{1-4}$alkyl)amino, hydroxycarbonyl, $C_{1-6}$alkyloxycarbonyl, $C_{1-6}$alkylthio$C_{1-6}$alkyl, $C_{1-6}$alkylS(O)$C_{1-6}$alkyl or $C_{1-6}$alkylS(O)$_2C_{1-6}$alkyl;

$R^{16}$ may also be bound to one of the nitrogen atoms in the imidazole ring of formula (c-1), in which case the meaning of $R^{16}$ when bound to the nitrogen is limited to hydrogen, aryl, $C_{1-6}$alkyl, hydroxy$C_{1-6}$alkyl, $C_{1-6}$alkyloxy$C_{1-6}$alkyl, $C_{1-6}$alkyloxycarbonyl, $C_{1-6}$alkylS(O)$C_{1-6}$alkyl or $C_{1-6}$alkylS(O)$_2C_{1-6}$alkyl;

$R^{17}$ is hydrogen, $C_{1-6}$alkyl, trifluoromethyl or di($C_{1-4}$alkyl)aminosulfonyl.

As used in the foregoing definitions and hereinafter, halo is generic to fluoro, chloro, bromo and iodo; $C_{1-4}$alkyl defines straight and branched chain saturated hydrocarbon radicals having from 1 to 4 carbon atoms such as, e.g. methyl, ethyl, propyl, butyl, 1-methylethyl, 2-methylpropyl and the like; $C_{1-6}$alkyl includes $C_{1-4}$alkyl and the higher homologues thereof having 5 to 6 carbon atoms such as, for example, pentyl, 2-methylbutyl, hexyl, 2-methylpentyl and the like; $C_{1-6}$alkanediyl defines bivalent straight and branched chained saturated hydrocarbon radicals having from 1 to 6 carbon atoms, such as, for example, methylene, 1,2-ethanediyl, 1,3-propanediyl, 1,4-butanediyl, 1,5-pentanediyl, 1,6-hexanediyl and the branched isomers thereof; $C_{2-6}$alkenyl defines straight and branched chain hydrocarbon radicals containing one double bond and having from 2 to 6 carbon atoms such as, for example, ethenyl, 2-propenyl, 3-butenyl, 2-pentenyl, 3-pentenyl, 3-methyl-2-butenyl, and the like. The term "S(O)" refers to a sulfoxide and "S(O)$_2$" to a sulfon.

The pharmaceutically acceptable acid addition salts as mentioned hereinabove are meant to comprise the therapeutically active non-toxic acid addition salt forms which the compounds of formula (I) are able to form. The compounds of formula (I) which have basic properties can be converted in their pharmaceutically acceptable acid addition salts by treating said base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The term acid addition salts also comprises the hydrates and the solvent addition forms which the compounds of formula (I) are able to form. Examples of such forms are e.g. hydrates, alcoholates and the like.

The term stereochemically isomeric forms of compounds of formula (I), as used hereinbefore, defines all possible compounds made up of the same atoms bonded by the same sequence of bonds but having different three-dimensional structures which are not interchangeable, which the compounds of formula (I) may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of formula (I) both in pure form or in admixture with each other are intended to be embraced within the scope of the present invention.

Some of the compounds of formula (I) may also exist in their tautomeric forms. Such forms although not explicitly indicated in the above formula are intended to be included within the scope of the present invention.

Whenever used hereinafter, the term "compounds of formula (I)" is meant to include also the pharmaceutically acceptable acid addition salts and all stereoisomeric forms.

A group of interesting compounds consists of those compounds of formula (I) wherein one or more of the following restrictions apply:

=$X^1$—$X^2$—$X^3$ is a trivalent radical of formula (x-1), (x-2), (x-3), (x4) or (x-9) wherein each $R^6$ independently is hydrogen, $C_{1-4}$alkyl, $C_{1-4}$alkyloxycarbonyl, amino or aryl and $R^7$ is hydrogen;

>$Y^1$—$Y^2$— is a trivalent radical of formula (y-1), (y-2), (y-3), or (y-4) wherein each $R^9$ independently is hydrogen, halo, carboxyl, $C_{1-4}$alkyl or $C_{1-4}$alkyloxycarbonyl;

r is 0, 1 or 2;

s is 0 or 1;

t is 0;

$R^1$ is halo, $C_{1-6}$alkyl or two $R^1$ substituents ortho to one another on the phenyl ring may independently form together a bivalent radical of formula (a-1);

$R^2$ is halo;

$R^3$ is halo or a radical of formula (b-1) or (b-3) wherein $R^{10}$ is hydrogen or a radical of formula -Alk-$OR^{13}$.

$R^{11}$ is hydrogen;

$R^{12}$ is hydrogen, $C_{1-6}$alkyl, $C_{1-6}$alkylcarbonyl, hydroxy, $C_{1-6}$alkyloxy or mono- or di($C_{1-6}$alkyl)amino$C_{1-6}$alkylcarbonyl;

Alk is $C_{1-6}$alkanediyl and $R^{13}$ is hydrogen;

$R^4$ is a radical of formula (c-1) or (c-2) wherein $R^{16}$ is hydrogen, halo or mono- or di($C_{1-4}$alkyl)amino;

$R^{17}$ is hydrogen or $C_{1-6}$alkyl;

aryl is phenyl.

A particular group of compounds consists of those compounds of formula (I) wherein =$X^1$—$X^2$—X3 is a trivalent radical of formula (x-1), (x-2), (x-3) or (x-9), >$Y^1$—Y2 is a trivalent radical of formula (y-2), (y-3) or (y-4), r is 0 or 1, s is 1, t is 0, $R^1$ is halo, $C_{1-4}$)alkyl or forms a bivalent radical of formula (a-1), $R^2$ is halo or $C_{1-4}$alkyl, R is hydrogen or a radical of formula (b-1) or (b-3), $R^4$ is a radical of formula (c-1) or (c-2), $R^6$ is hydrogen, $C_{1-4}$alkyl or phenyl, $R^7$ is hydrogen, $R^9$ is hydrogen or $C_{1-4}$alkyl, $R^{10}$ is hydrogen or -Alk-$OR^{13}$, $R^{11}$ is hydrogen and $R^{12}$ is hydrogen or $C_{1-6}$alkylcarbonyl and $R^{13}$ is hydrogen;

Preferred compounds are those compounds of formula (I) wherein =$X^1$—$X^2$—$X^3$ is a trivalent radical of formula (x-1), >Y1—Y2 is a trivalent radical of formula (y-4), r is 0 or 1, s is 1, t is 0, $R^1$ is halo, preferably chloro and most preferably 3-chloro, $R^2$ is halo, preferably 4-chloro or 4-fluoro, $R^3$ is hydrogen or a radical of formula (b-1) or (b-3), $R^4$ is a radical of formula (c-1) or (c-2), $R^6$ is hydrogen, $R^7$ is hydrogen, $R^9$ is hydrogen, $R^{10}$ is hydrogen, $R^{11}$ is hydrogen and $R^{12}$ is hydrogen;

Other preferred compounds are those compounds of formula (I) wherein =$X^1$—$X^2$—$X^3$ is a trivalent radical of formula (x-2) or (x-3), >Y1—Y2 is a trivalent radical of formula (y-2), (y-3) or (y-4), r and s are 1, t is 0, $R^1$ is halo, preferably chloro, and most preferably 3-chloro or $R^1$ is $C_{1-4}$alkyl, preferably 3-methyl, $R^2$ is halo, preferably chloro, and most preferably 4-chloro, $R^3$ is a radical of formula (b-1) or (b-3), $R^4$ is a radical of formula (c-2), $R^6$ is $C_{1-4}$alkyl, $R^9$ is hydrogen, $R^{10}$ and $R^{11}$ are hydrogen and $R^{12}$ is hydrogen or hydroxy;

The most preferred compounds of formula (I) are 7-[(4-fluorophenyl)(1H-imidazol-1-yl)methyl]-5-phenylimidazo[1,2-a]quinoline; α-(4-chlorophenyl)-α-(1-methyl-1H-imidazol-5-yl)-5-phenylimidazo[1,2-]aquinoline-7-methanol; 5-(3-chlorophenyl)-α-(4-chlorophenyl)-α-(1-methyl-1H-imidazol-5-yl)-imidazol[1,2-a]quinoline-7-methanol; 5-(3-chlorophenyl)-α-(4-chlorophenyl)-α-(1-methyl-1H-imidazol-5-yl)imidazol[1,2-a]quinoline-7-methanamine; 5-(3-chlorophenyl)-α-(4-chlorophenyl)-α-(1-methyl-1H-imidazol-5-yl)tetrazolo[1,5-a]quinoline-7-methanamine; 5-(3-chlorophenyl)-α-(4-chlorophenyl)-1-methyl-α-(1-methyl-1H-imidazol-5-yl)-1,2,4-triazolo[4,3-a]quinoline-7-methanol; 5-(3-chlorophenyl)-α-(4- chlorophenyl)-α-(1-methyl-1-imidazol-5-yl)tetrazolo[1,5-a]quinoline-7-methanamine; 5-(3-chlorophenyl)-α-(4-chlorophenyl)-α-(1-methyl-1H-imidazol-5-yl)tetrazolo[1,5-a]quinazoline-7-methanol; 5-(3-chlorophenyl)-α-(4-chlorophenyl)-4,5-dihydro-α-(1-methyl-1H-imidazol-5-yl)tetrazolo[1,5-a]quinazoline-7-methanol; 5-(3-chlorophenyl)-α-(4-chlorophenyl)-α-(1-methyl-1H-imidazol-5-yl)tetrazolo[1,5-a]quinazoline-7-methanamine; 5-(3-chlorophenyl)-α-(4-chlorophenyl)-N-hydroxy-α-(1-methyl-1H-imidazol-5-yl)tetrahydro[1,5-a]quinoline-7-methanamine; α-(4-chlorophenyl)-α-(1-methyl-1H-imidazol-5-yl)-5-(3-methylphenyl)tetrazolo[1,5-a]quinoline-7-methanamine; the pharmaceutically acceptable acid addition salts and the stereochemically isomeric forms thereof.

The compounds of formula (I) wherein =$X^1$—$X^2$—$X^3$ is a trivalent radical of formula (x-1) and $R^6$ and $R^7$ are hydrogen, represented by compounds of formula (I-1), can generally be prepared by reacting an intermediate of formula (II) with a reagent of formula (III) or a functional derivative thereof, wherein $W^1$ is an appropriate leaving group such as chloro, followed by an intramolecular cyclization which can be performed in a reaction-inert solvent such as xylene and in the presence of a suitable acid, for example acetic acid. The reaction may conveniently be carried out at elevated temperatures ranging from 80° C. to reflux temperature.

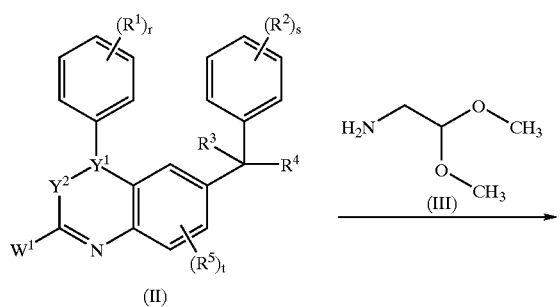

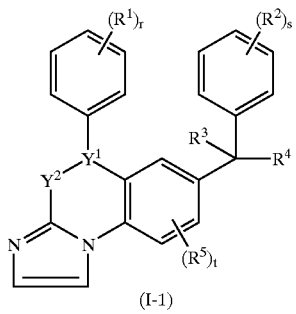

Alternatively, compounds of formula (I) wherein =X¹—X²—X³ is a trivalent radical of formula (x-1), >Y¹—Y² is a trivalent radical of formula (y4), R⁹ is hydrogen and R⁶ and/or R⁷ are not hydrogen, represented by formula (I-1-a) can be prepared by reacting a compound of formula (IV) with a reagent of formula (V) followed by an intramolecular cyclization which can be performed in a reaction-inert solvent such as ethanol. The reaction may conveniently be carried out at temperatures ranging from room temperature to 80° C.

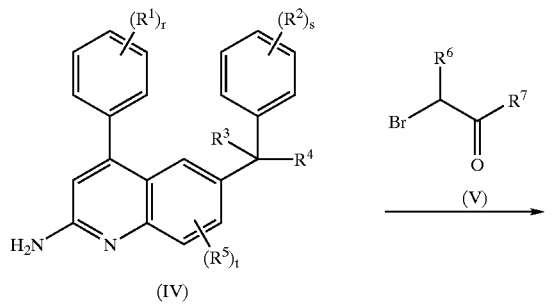

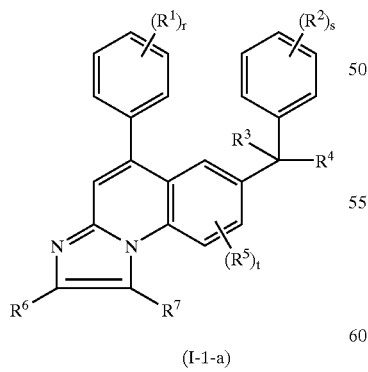

The compounds of formula (1) wherein =X¹—X²—X³ is a trivalent radical of formula (x-2), represented by compounds of formula (I-2), can generally be prepared by reacting a compound of formula (II) with an intermediate of formula (VI). Said reaction can be performed in an appropriate solvent such as 1-butanol at elevated temperatures ranging from 80° C. to reflux temperature.

Alternatively, compounds of formula (I-2) can be prepared by reacting a compound of formula (VIII) with an intermediate of formula (VII). Said reaction can be performed in an appropriate solvent such as n-butanol at a temperature ranging between room temperature and reflux temperature. The intermediates of formula (VII) can be prepared by reacting an intermediate of formula (II) with N₂H₄. Said reaction can be performed in a reaction-inert solvent such as dioxane. The reaction may conveniently be carried out at a temperature ranging between room temperature and 100° C.

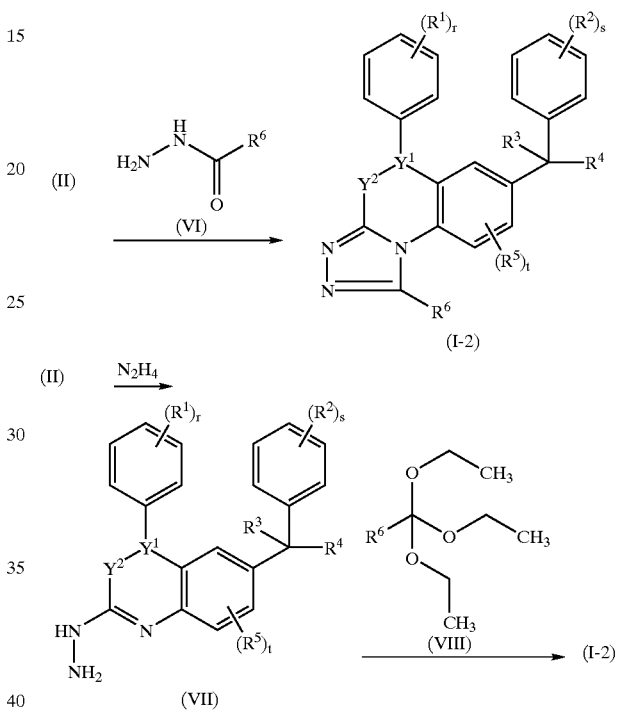

Compounds of formula (I-2) wherein R⁶ is an amine, represented by compounds of formula (I-2-a) can be prepared by reacting an intermediate of formula (VII) with BrCN in a reaction-inert solvent such as methanol. The reaction may conveniently be carried out at a temperature ranging between 0° C. and 100° C.

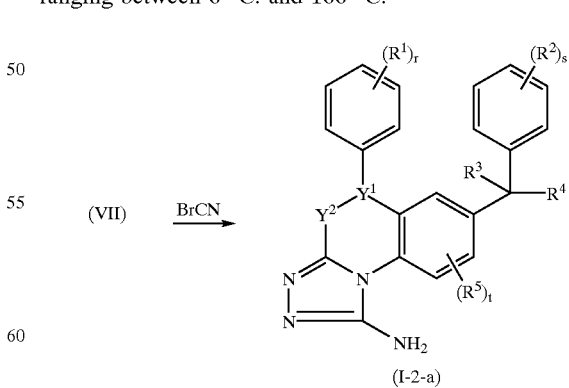

The compounds of formula (I) wherein =X¹—X²—X³ is a trivalent radical of formula (x-3), represented by compounds of formula (I-3), can generally be prepared by reacting an intermediate of formula (VII) with a compound of formula (IX) in a reaction-inert solvent such as tetrahydrofuran. The reaction may conveniently be carried out at a temperature ranging between 0° C. and 50° C.

Alternatively, the compounds of formula (I-3) can be prepared by reacting a compound of formula (X) with an intermediate of formula (II). Said reaction can be performed in an appropriate solvent such as 1-butanol at an elevated temperature ranging from 80° C. to reflux temperature.

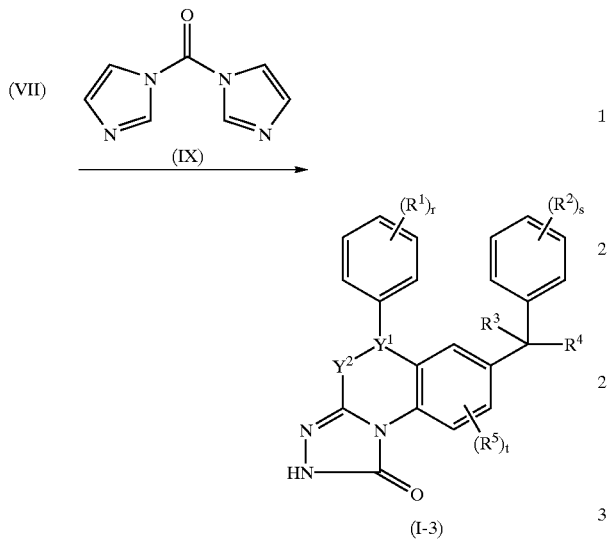

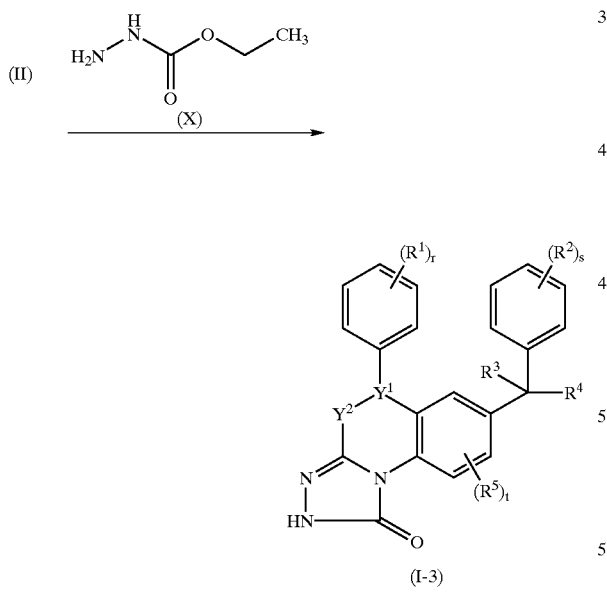

The compounds of formula (1) wherein =X¹—X²—X³ is a trivalent radical of formula (x-4), represented by compounds of formula (I-4), can generally be prepared by reacting an intermediate of formula (II) with $N_aN_3$ in a reaction-inert solvent such as N,N-dimethylformamide. The reaction may conveniently be carried out at an elevated temperature ranging between 60° C. and 150° C.

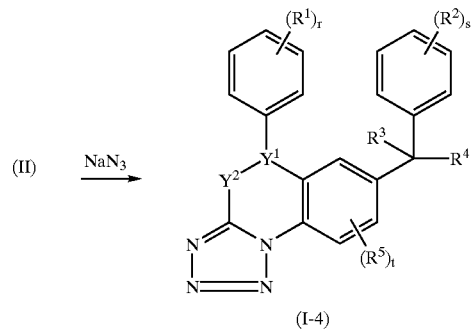

The compounds of formula (I-4) can also be prepared by reacting an intermediate of formula (XVIII) with $NaNO_2$ in an acidic aqueous medium such as, for example HCl in water.

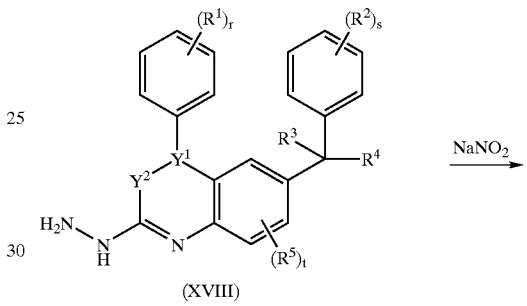

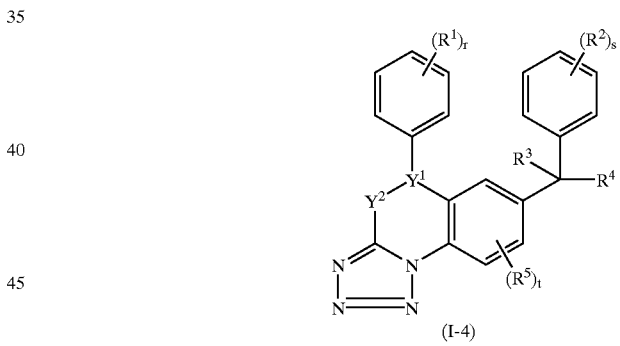

The compounds of formula (I) wherein =X¹—X²—X³ is a trivalent radical of formula (x-9), >Y¹—Y² is a trivalent radical of formula (y-4) and R is hydrogen, represented by compounds of formula (I-5), can generally be prepared by reacting an intermediate of formula (XI) with a compound of formula (XII) in a reaction-inert solvent such as methanol. Convenient reaction temperatures range between room temperature and 80° C. The intermediates of formula (XI) can be prepared by reacting an intermediate of formula (XIII) with $SeO_2$ in a reaction-inert solvent such as dioxane. The reaction may conveniently be carried out at an elevated temperature ranging between room temperature and reflux temperature. Intermediates of formula (XIII) can generally be prepared by reacting an intermediate of formula (XIV) with 2-propanone in an acid solution such as a mixture of acetic acid and $H_2SO_4$. The reaction may conveniently be carried out at an elevated temperature ranging between room temperature and reflux temperature.

formula (y-2) or (y4) can be converted to the corresponding compounds of formula (I-7) wherein $>Y^1—Y^2$ is a trivalent radical of formula (y-3) or (y-1) and $R^9$ is hydrogen, using art-known reduction procedures such as treatment with $NaBH_4$ or $LiAlH_4$ in a suitable solvent such as methanol or tetrahydrofuran.

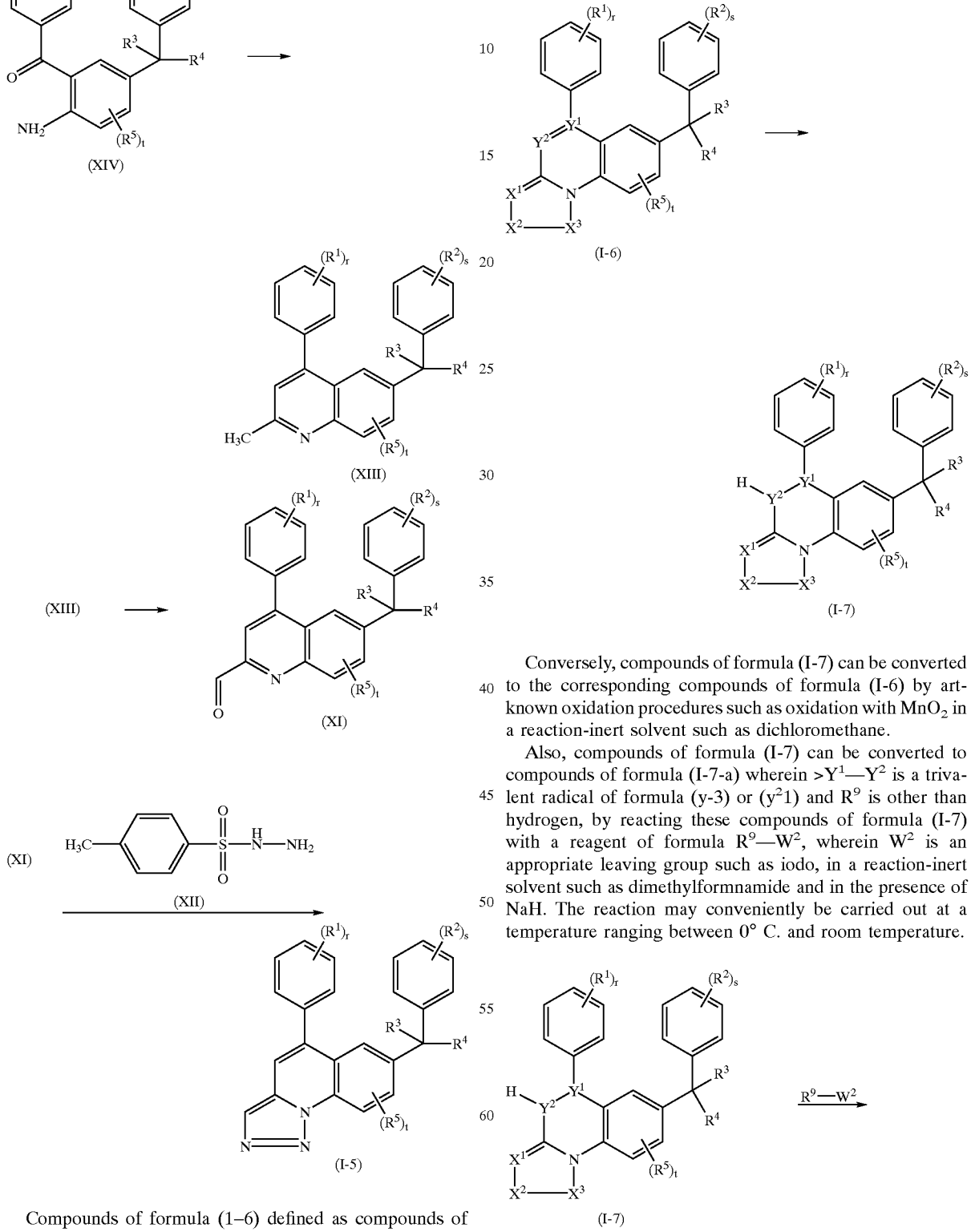

Conversely, compounds of formula (I-7) can be converted to the corresponding compounds of formula (I-6) by art-known oxidation procedures such as oxidation with $MnO_2$ in a reaction-inert solvent such as dichloromethane.

Also, compounds of formula (I-7) can be converted to compounds of formula (I-7-a) wherein $>Y^1—Y^2$ is a trivalent radical of formula (y-3) or ($y^21$) and $R^9$ is other than hydrogen, by reacting these compounds of formula (I-7) with a reagent of formula $R^9—W^2$, wherein $W^2$ is an appropriate leaving group such as iodo, in a reaction-inert solvent such as dimethylformnamide and in the presence of NaH. The reaction may conveniently be carried out at a temperature ranging between 0° C. and room temperature.

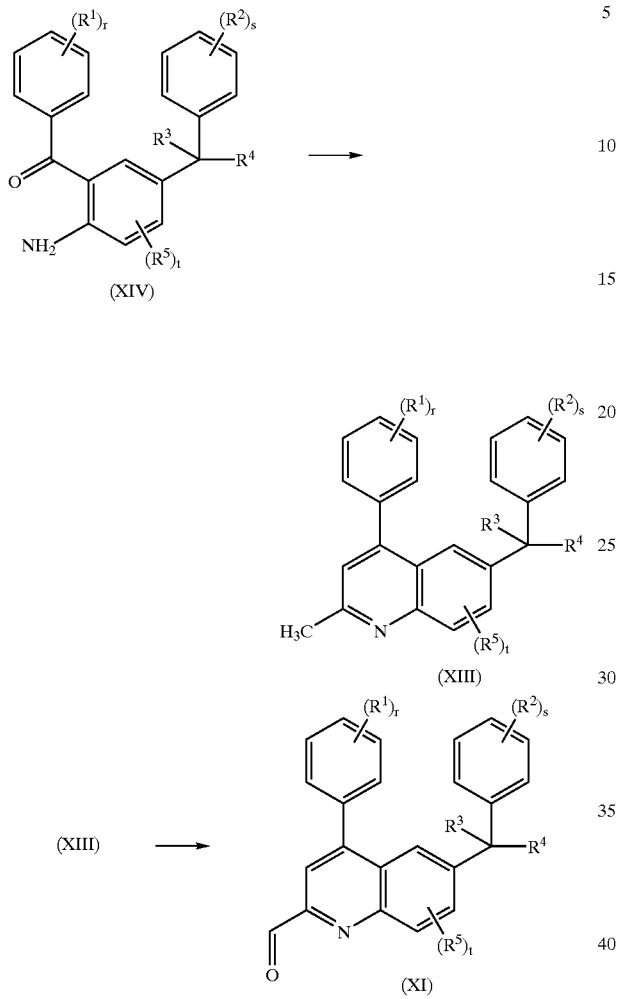

Compounds of formula (1–6) defined as compounds of formula (1) wherein $>Y^1—Y^2$ is a trivalent radical of

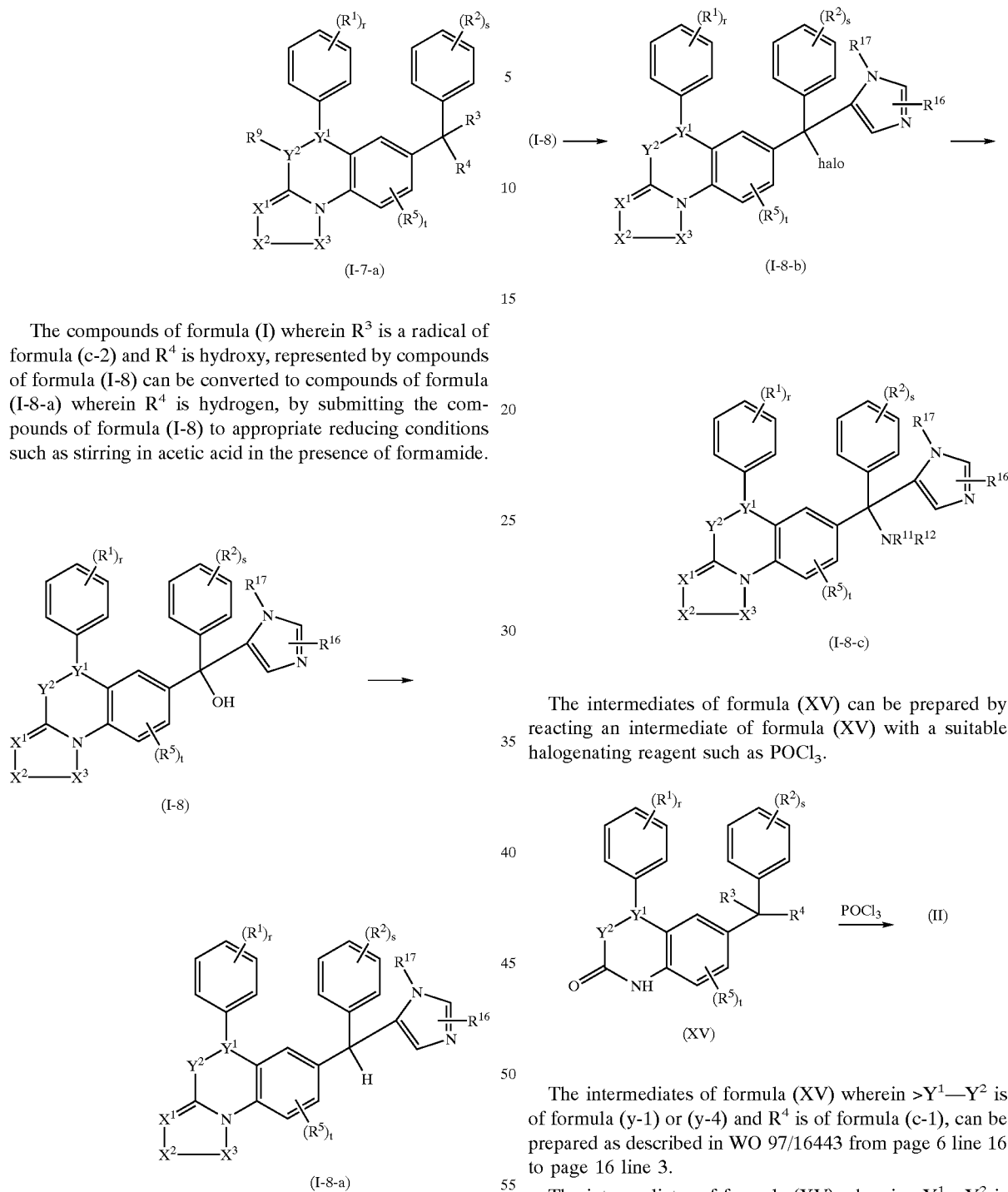

(I-7-a)

The compounds of formula (I) wherein $R^3$ is a radical of formula (c-2) and $R^4$ is hydroxy, represented by compounds of formula (I-8) can be converted to compounds of formula (I-8-a) wherein $R^4$ is hydrogen, by submitting the compounds of formula (I-8) to appropriate reducing conditions such as stirring in acetic acid in the presence of formamide.

(I-8)

(I-8-a)

Further, compounds of formula (I-8) can be converted to compounds of formula (I-8-b) wherein $R^4$ is halo, by reacting the compounds of formula (I-8) with a suitable halogenating agent such as thionyl chloride or phosphorus tribromide. Successively, the compounds of formula (I-8-b) can be treated with a reagent of formula H—$NR^{11}R^{12}$ in a reaction-inert solvent, thereby yielding compounds of formula (I-8-c).

(I-8-b)

(I-8-c)

The intermediates of formula (XV) can be prepared by reacting an intermediate of formula (XV) with a suitable halogenating reagent such as $POCl_3$.

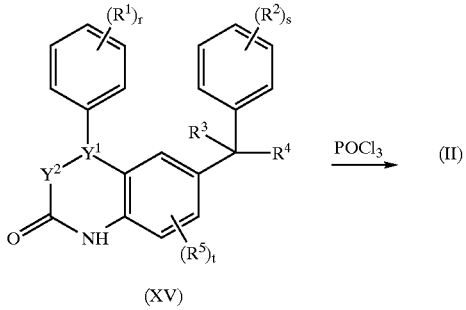

(XV)

The intermediates of formula (XV) wherein >$Y^1$—$Y^2$ is of formula (y-1) or (y-4) and $R^4$ is of formula (c-1), can be prepared as described in WO 97/16443 from page 6 line 16 to page 16 line 3.

The intermediates of formula (XV) wherein >$Y^1$—$Y^2$ is of formula (y-1) or (y-4) and $R^4$ is of formula (c-2), can be prepared as described in WO 97/21701 from page 7 line 28 to page 16 line 3.

The intermediates of formula (XV) wherein >$Y^{12}$—$Y^2$ is of formula (y-2) or (y-3) and $R^4$ is of formula (c-1) or (c-2), can be prepared as described in WO 98/49157 from page 6 line 27 to page 13 line 14.

Alternatively, intermediates of formula (II) wherein $W^1$ is chloro and $R^3$ is hydroxy, represented by intermediates of formula (II-a) can be prepared by reacting an intermediate of formula (XVI), wherein $W^3$ is a suitable leaving group such as Br, with an intermediate ketone of formula (XVII). This reaction is performed by converting the intermediate of formula (XVI) into an organometallic compound, by stirring it with a strong base such as butyl lithium and subsequently adding the intermediate ketone of formula (XVII). The hydroxy derivative can subsequently be converted into other intermediates wherein $R^4$ has another definition by performing art-known functional group transformations.

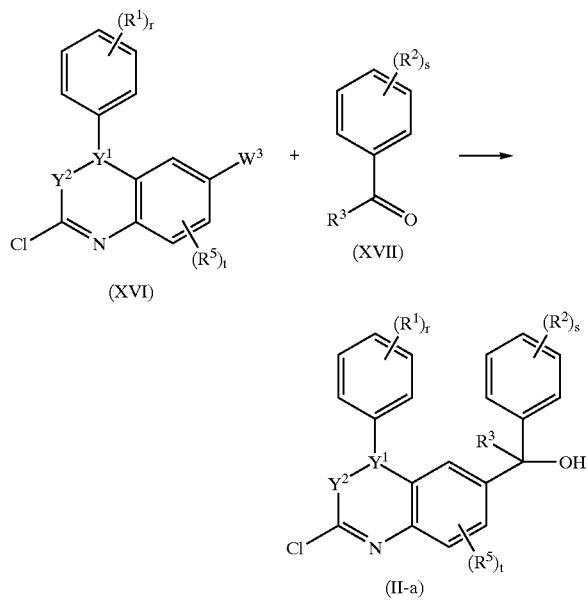

Intermediates of formula (IV) can be prepared by reacting an intermediate of formula (XIV) with $CH_3CN$ in the presence of NaH and a suitable base such as pyridine. The reaction may conveniently be carried out at an elevated temperature ranging between 50° C. and 100° C.

Intermediates of formula (XIV) can be prepared according to methods as described in WO 97/16443 and WO 97/21701.

The compounds of formula (I) and some of the intermediates have at least one stereogenic center in their structure. This stereogenic center may be present in a R or a S configuration.

The compounds of formula (I) as prepared in the hereinabove described processes are generally racemic mixtures of enantiomers which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds of formula (I), the pharmaceutically acceptable acid addition salts and stereoisomeric forms thereof have valuable pharmacological properties in that they surprisingly have both farnesyl protein transferase (FPTase) and geranylgeranyl transferase (GGTase) inhibitory effects.

Furthermore, the compounds of formula (1), in particular those compounds of formula (I) wherein $=X^1-X^2-X^3$ is a trivalent radical of formula (x-4), display potent GGTase inhibition.

Other compounds of formula (I) are found to be particularly useful for the inhibition of FPTase activity.

This invention provides a method for inhibiting the abnormal growth of cells, including transformed cells, by administering an effective amount of a compound of the invention. Abnormal growth of cells refers to cell growth independent of normal regulatory mechanisms (e.g. loss of contact inhibition). This includes the abnormal growth of: (1) tumor cells (tumors) expressing an activated ras oncogene; (2) tumor cells in which the ras protein is activated as a result of oncogenic mutation of another gene; (3) benign and malignant cells of other proliferative diseases in which aberrant ras activation occurs. Furthermore, it has been suggested in literature that ras oncogenes not only contribute to the growth of tumors in vivo by a direct effect on tumor cell growth but also indirectly, i.e. by facilitating tumor-induced angiogenesis (Rak. J. et al, Cancer Research, 55, 4575–4580, 1995). Hence, pharmacologically targeting mutant ras oncogenes could conceivably suppress solid tumor growth in vivo, in part, by inhibiting tumor-induced angiogenesis.

This invention also provides a method for inhibiting tumor growth by administering an effective amount of a compound of the present invention, to a subject, e.g. a mammal (and more particularly a human) in need of such treatment. In particular, this invention provides a method for inhibiting the growth of tumors expressing an activated ras oncogene by the administration of an effective amount of the compounds of the present invention. Examples of tumors which may be inhibited, but are not limited to, lung cancer (e.g. adenocarcinoma), pancreatic cancers (e.g. pancreatic carcinoma such as, for example exocrine pancreatic carcinoma), colon cancers (e.g. colorectal carcinomas, such as, for example, colon adenocarcinoma and colon adenoma), hematopoietic tumors of lymphoid lineage (e.g. acute lymphocytic leukemia, B-cell lymphoma, Burkitt's lymphoma), myeloid leukemias (for example, acute myelogenous leukemia (AML)), thyroid follicular cancer, myelodysplastic syndrome (MDS), tumors of mesenchymal origin (e.g. fibrosarcomas and rhabdomyosarcomas), melanomas, teratocarcinomas, neuroblastomas, gliomas, benign tumor of the skin (e.g. keratoacanthomas), breast carcinoma, kidney carcinoma, ovary carcinoma, bladder carcinoma and epidermal carcinoma.

This invention may also provide a method for inhibiting proliferative diseases, both benign and malignant, wherein ras proteins are aberrantly activated as a result of oncogenic mutation in genes. With said inhibition being accomplished by the administration of an effective amount of the compounds described herein, to a subject in need of such a treatment. For example, the benign proliferative disorder neurofibromatosis, or tumors in which ras is activated due to mutation or overexpression of tyrosine kinase oncogenes, may be inhibited by the compounds of this invention.

The compounds of present invention are particularly useful for the treatment of proliferative diseases, both benign and malignant, wherein the K-ras B isoform is activated as a result of oncogenic mutation.

Hence, the present invention discloses the compounds of formula (I) for use as a medicine as well as the use of these compounds of formula (I) for the manufacture of a medicament for treating one or more of the above mentioned conditions.

In view of their useful pharmacological properties, the subject compounds may be formulated into various pharmaceutical forms for administration purposes.

To prepare the pharmaceutical compositions of this invention, an effective amount of a particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Those skilled in the art could easily determine the effective amount from the test results presented hereinafter. In general it is contemplated that an effective amount would be from 0.01 mg/kg to 100 mg/kg body weight, and in particular from 0.05 mg/kg to 10 mg/kg body weight. It may be appropriate to administer the required dose as two, three, four or more sub-doses at appropriate intervals throughout the day. Said sub-doses may be formulated as unit dosage forms, for example, containing 0.5 to 500 mg, and in particular 1 mg to 200 mg of active ingredient per unit dosage form.

The following examples are provided for purposes of illustration.

EXPERIMENTAL PART

Hereinafter "THF" means tetrahydrofuran, "DIPE" means diisopropylether, "DME" means 1,2-dimethoxyethane and "EtOAc" means ethylacetate.

A. PREPARATION OF THE INTERMEDIATES

Example A1 a) A mixture of (±)-6-[(4-fluorophenyl)(1H-imidazol-1-yl)methyl]4-phenyl-2(1H)-quinolinone (0.0253 mol) in phosphoryl chloride (30 ml) was refluxed for 1 hour. The mixture was evaporated till dryness and the product was used without further purification, yielding 10.4 g (99%) of (±)-2-chloro-6-[(4-fluorophenyl)(1H-imidazol-1-yl) methyl]-4-phenyl-quinoline (interm. 1).

b) A mixture of intermediate (1) (0.0251 mol) in 2,2-dimethoxyethylamine (20 ml) was stirred at 120° C. for 12 hours. The mixture was poured into ice water and extracted with $CH_2Cl_2$. The organic layer was dried ($MgSO_4$) and evaporated till dryness. The oily residue (21 g) was purified by column chromatography over silica gel. The pure fractions were collected and evaporated, yielding 10 g (83%) of (±)-N-(2,2-dimethoxyethyl)-6-[(4-fluorophenyl)(1H-imidazol-1-yl)methyl]4-phenyl-2-quinolinamine (interm. 2).

Example A2 intermediate (3)

a) Preparation of 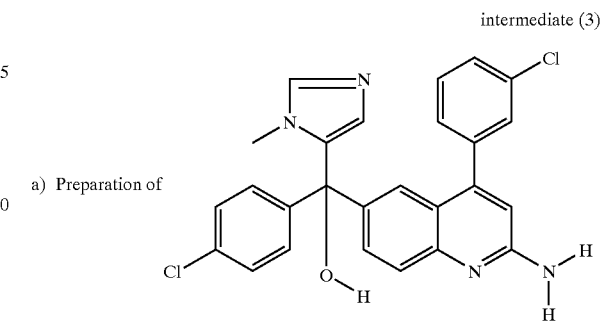

Sodium hydride (0.0384 mol) was added portionwise to a mixture of (±)-[2-amino-5-[(4-chlorophenyl)hydroxy(1-methyl-1H-imidazol-5-yl)methyl]phenyl](3-chlorophenyl) methanone (0.00961 mol) and acetonitrile (0.058 mol) in pyridine (30 ml). The mixture was stirred at 90° C. for 6 hours and then cooled. $H_2O$ was added. The solvent was evaporated. The residue was taken up in $CH_2Cl_2$. The organic solution was washed with $H_2O$, dried ($MgSO_4$), filtered and the solvent was evaporated. The residue (6.1 g) was purified by column chromatography over silica gel. The pure fractions were collected and the solvent was evaporated, yielding 2.9 g (63%) of intermediate 3.

intermediate (4)

a) Preparation of 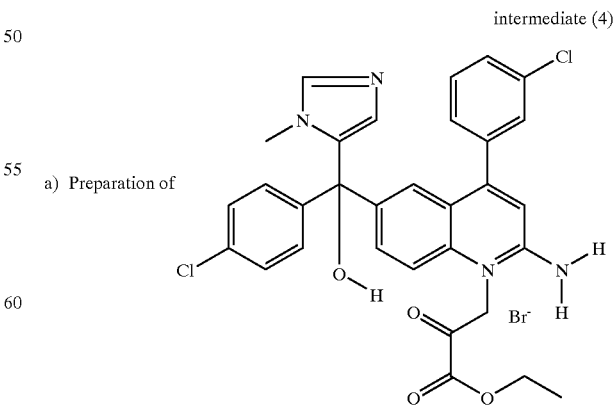

Ethyl bromopyruvate (0.0023 mol) was added to a mixture of intermediate (3) (0.0019 mol) in DME (5 ml). The mixture was stirred at room temperature for 19 hours. A gum was filtered off, washed with diethyl ether and used without further purification, yielding intermediate (4).

Example A3

A mixture of (±)-6-[(4-chlorophenyl)-1H-imidazol-1-ylmethyl]4-phenyl-2(1H)-quinolinone (0.022 mol) in phosphoryl chloride (100 ml) was stirred and refluxed for 2 hours. The mixture was evaporated in vacuo, the residue was taken up in CH$_2$Cl2 and basified with K$_2$CO$_3$ (10%). The organic layer was dried (MgSO$_4$), filtered off and evaporated. The product was used without further purification, yielding 8 g (85%) of (±)-2-chloro-6-[(4-chlorophenyl)-1H-imidazol-1-ylmethyl]-4-phenylquinoline (interm. 5).

Example A4

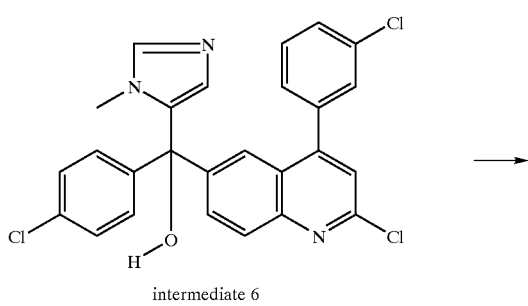

intermediate 6

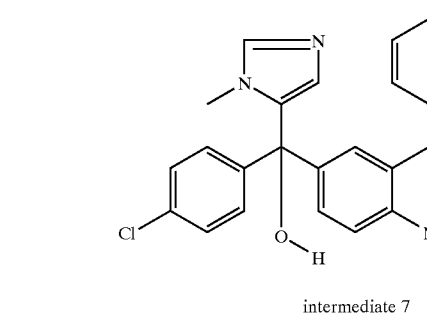

intermediate 7

A mixture of intermediate (6) (0.0242 mol) in hydrazine hydrate (120 ml) and dioxane (240 ml) was stirred at 70° C. overnight and then brought to room temperature. H$_2$O was added and the mixture was extracted with CH$_2$Cl$_2$. The organic layer was separated, washed with a saturated NaCl solution, dried (MgSO$_4$), filtered and the solvent was evaporated, yielding 11.8 g of intermediate 7.

Example A5

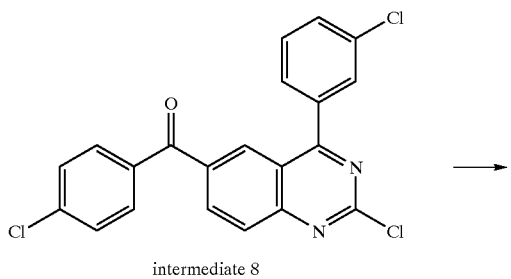

intermediate 8

-continued

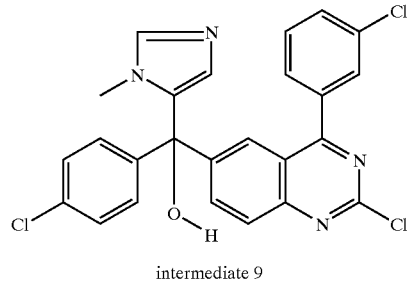

intermediate 9

A solution of butyllithium in hexane (1.6 M) (74.4 ml) was added dropwise at −70° C. under N$_2$ flow to a mixture of 1-methylimidazole (0.119 mol) in THF (200 ml). The mixture was stirred at −70° C. for 30 minutes. Chlorotriethylsilane (0.119 mol) was added. The mixture was brought slowly to 10° C. and cooled again to −70° C. A solution of butyllithium in hexane (1.6 M) (74.4 ml) was added dropwise. The mixture was stirred at −70° C. for 1 hour, brought to −15° C. and cooled again to −70° C. A mixture of intermediate (8) (0.052 mol) in THF (200 ml) was added dropwise. The mixture was stirred at −70° C. for 30 min, hydrolized, extracted with EtOAc and decanted. The organic layer was dried (MgSO$_4$), filtered and the solvent was evaporated. The residue was purified by column chromatography over silica gel. The pure fractions were collected and the solvent was evaporated, yielding 12 g (46.5%) of intermediate (9).

Example A6 a) Preparation of

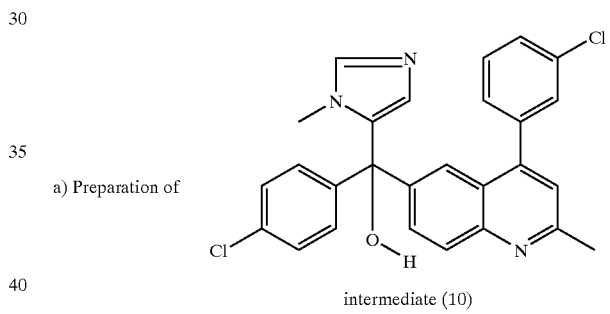

intermediate (10)

A mixture of (±)-[2-amino-5-[(4-chlorophenyl)hydroxy(1-methyl-1H-imidazol-5-yl]methyl)phenyl](3-chlorophenyl)methanone (0.0415 mol) and 2-propanone (0.124 mol) in sulfuric acid (0.6 ml) and acetic acid (55 ml) was stirred and refluxed overnight, brought to room temperature, poured out on ice, basified with NH$_4$OH and extracted with CH$_2$Cl$_2$. The organic layer was separated, dried (MgSO$_4$), filtered and the solvent was evaporated. The residue (30 g) was purified by column chromatography over silica gel. The pure fractions were collected and the solvent was evaporated, yielding 12 g (60%) of product. Part of this fraction (2 g) was crystallized from CH$_3$CN. The precipitate was filtered off and dried, yielding 1.25 g (37.5%) of intermediate (10).

b) Preparation of

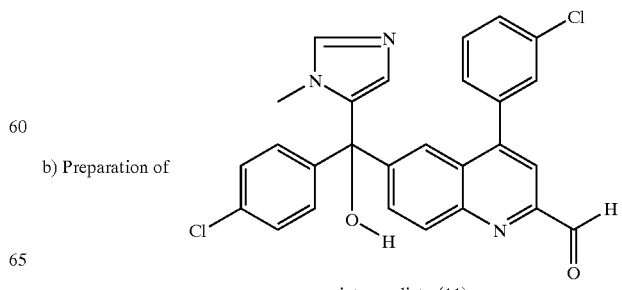

intermediate (11)

A mixture of intermediate (10) (0.0116 mol) and selenium dioxide (0.0116 mol) in dioxane (55 ml) and water (5.5 ml) was stirred and refluxed for 3 hours. The mixture was cooled, filtered over celite, washed with CH₂Cl₂, dried (MgSO₄), filtered and the solvent was evaporated, yielding 5.66 g of intermediate (11).

Example A7

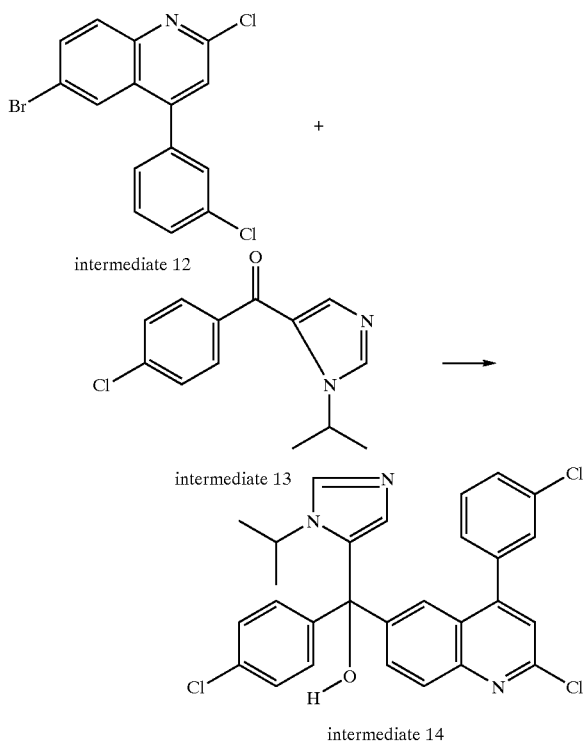

Butyllithium in hexane (1.6 M) (5.3 ml) was added dropwise at −70° C. to a mixture of intermediate (12) (0.0071 mol) in tetrahydrofuran (25 ml). The mixture was stirred at −70° C. for 30 minutes. A solution of intermediate (13) (0.0078 mol) in TBF (10 ml) was added dropwise. The mixture was stirred for 1 hour, hydrolized and extracted with EtOAc. The organic layer was separated, dried (MgSO₄), filtered and the solvent was evaporated till dryness. The residue (3.9 g) was purified by column. chromatography over silica gel. Two pure fractions were collected and their solvents were evaporated, yielding 1.3 g (65%; starting material (intermediate 13) and 0.71 g (19%) of intermediate Example A8

Preparation of 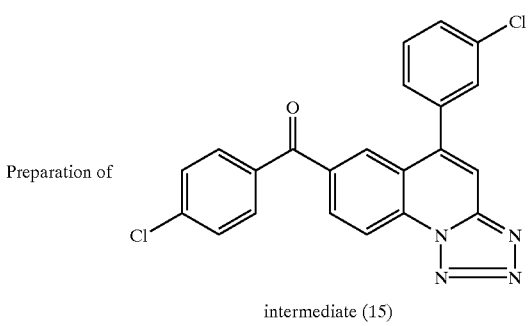

intermediate (15)

A mixture of (4-chlorophenyl)[2-chloro-4-(3-chlorophenyl)-6-quinolinyl]methanone (0.016 mol) and (14). NaN₃ (0.024 mol) in DMF (50 ml) was stirred at 100° C. for 8 hours, brought to room temperature and poured out on ice. The precipitate was filtered off, washed with H₂O and taken up in CH₂Cl₂. The organic layer was separated, dried, filtered and the solvent was evaporated. The residue was taken up in CH₃CN. The precipitate was filtered off and dried, yielding 5.1 g of intermediate (15) (76%).

Example A9

Preparation of 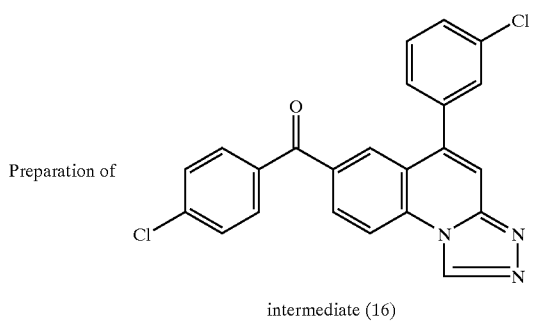

intermediate (16)

A mixture of (4-chlorophenyl)[2-chloro-4-(3-chlorophenyl)-6-quinolinyl]methanone monohydrochloride (0.0349 mol) and hydrazinecarboxaldehyde (0.0524 mol) in 1-butanol (180 ml) was stirred and refluxed for the weekend. The solvent was evaporated. THF (100 ml) and HCl 3N (200 ml) were added. The mixture was stirred and refluxed for 3 hours. The mixture was cooled, poured out on ice, basified with NH₄OH, filtered over celite, washed with EtOAc and decanted. The organic layer was dried (MgSO₄), filtered and the solvent was evaporated. The residue (11.8 g) was purified by column chromatography over silica gel (eluent: CH₂Cl₂/CH₃OH/NH₄OH 97/3/0.1; 20–45 μm). The pure fractions were collected and the solvent was evaporated. Yielding: 5 g of intermediate 16 (34%).

Example A10 a) Preparation of 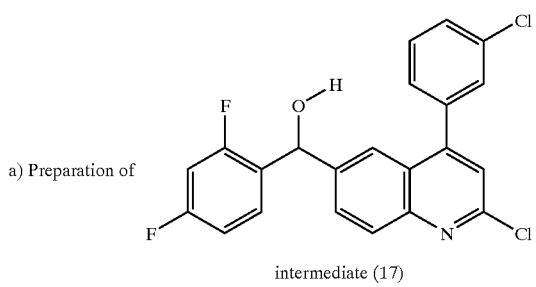

intermediate (17)

A mixture of 6-bromo-2chloro-4-(3-chlorophenyl) quinoline (0.0276 mol) in THF (30 ml) was cooled to −70° C. under N₂ flow. BuLi 1.6N in hexane (0.033 mol) was added dropwise at −70° C. The mixture was stirred at −70° C. for 1 hour. A solution of 2,4-difluorobenzaldehyde (0.0276 mol) in THF (100 ml) was added dropwise at −70° C. The mixture was stirred at −70° C. for 1 hour, hydrolized cold and extracted with EtOAc. The organic layer was separated, washed with H₂O. dried (MgSO₄), filtered and the solvent was evaporated. The residue was purified by column chromatography over silica gel (eluent: CH₂Cl₂/CH₃OH 99.5/0.5; 20–45 μm). The pure fractions were collected and the solvent was evaporated. Yielding: 5.2 g of intermediate (17) (46%).

b) Preparation of
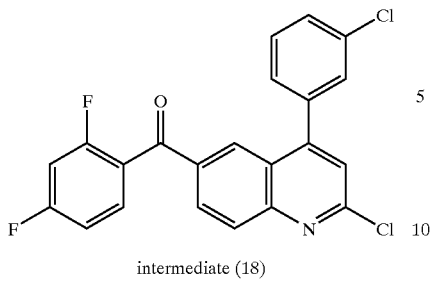
intermediate (18)
MnO$_2$ (0.0374 mol) was added to a mixture of intermediate (17) (0.0125 mol) in dioxane (50 ml). The mixture was stirred at 80° C. overnight, brought to room temperature, filtered over celite and washed with CH$_2$Cl$_2$. The filtrate was evaporated. Yielding: 5 g of intermediate (18) (96%).
Example A11

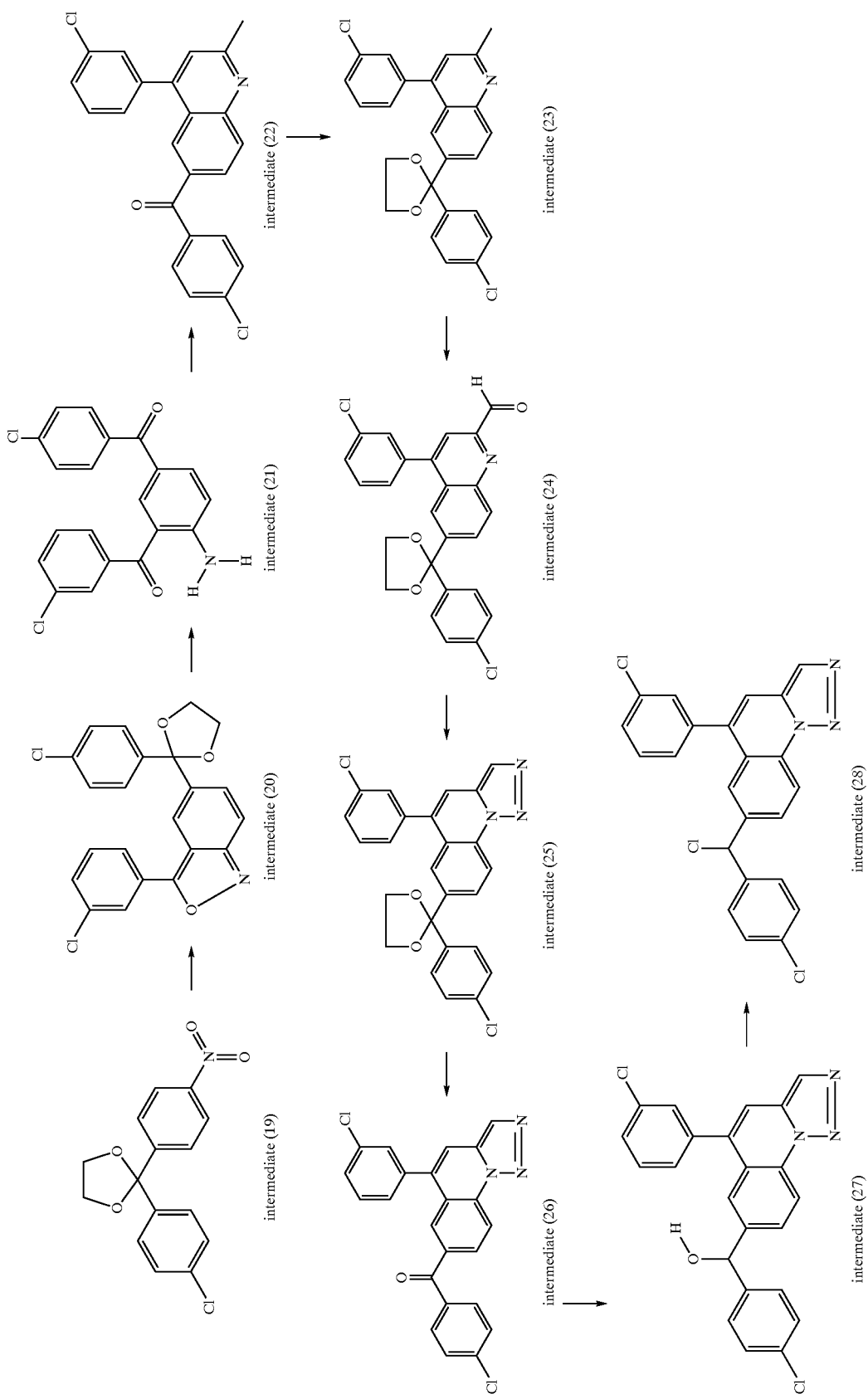

a) A mixture of (4-chlorophenyl)(4-nitrophenyl)-methanone (0.0382 mol), 1,2-ethanediol (0.0764 mol) and p-toluenesulfonic acid (0.19 mol) in toluene.(150 ml) was stirred and refluxed in a Dean Stark apparatus for 24 h. The mixture was washed with $K_2CO_3$ 10% and then with water. The organic layer was dried, filtered off and evaporated, yielding (98%) of intermediate 19.

b) Intermediate 19 and then 3-chloro-benzeneacetonitrile (0.147 mol) were added to a mixture of NaOH (0.409 mol) in methanol (100 ml). The mixture was stirred and refluxed. Ice and then ethanol were added. The mixture was allowed to crystallize out. The precipitate was filtered, washed with ethanol and dried, yielding intermediate 20.

c) $TiCl_3$ (15% in $H_2O$; 308ml) was added at room temperature to a mixture of intermediate 20 (0.124 mol) in THF (308ml). The mixture was stirred at room temperature for 48 hr. Water was added and the mixture was extracted with $CH_2Cl_2$. The organic layer was separated, washed with $K_2CO_3$ 10%, dried, filtered and the solvent was evaporated, yielding intermediate 21.

d) A mixture of intermediate 21 (0.097 mol) and 2-propanone (0.291 mol) in $H_2SO_4$ (1 ml) and acetic acid (100 ml) was stirred and refluxed for 24 hours. The mixture was poured out on ice and $N_4OH$ and extracted twice with $CH_2Cl_2$. The combined organic layer was separated, dried, filtered and the solvent was evaporated. The residue was taken up in $CH_3CN$, filtered off and dried, yielding 24 g (63%) of intermediate 22.

e) A mixture of intermediate 22 (0.0255 mol), 1,2-ethanediol (0.102 mol) and p-toluene sulfonic acid (0.0305 mol) in toluene (200 ml) was stirred and refluxed for 16 hours. The mixture was poured out on ice. $K_2CO_3$ 10% was added and the mixture was extracted twice with $CH_2Cl_2$. The combined organic layer was dried, filtered and the solvent was evaporated. The residue was crystallized from DIPE and pentane. The precipitate was filtered off and dried, yielding 9 g (80%) of intermediate 23.

f) A mixture of intermediate 23 (0.0206 mol) and $SeO_2$ (0.0206 mol) in dioxane (100 ml) and $H_2O$ (10 ml) was stirred and refluxed for 3 hours. The mixture was filtered warm over celite, washed with $H_2O$ and with $CH_2Cl_2$ and decanted. The organic layer was dried, filtered and the solvent was evaporated. The residue was purified by column chromatography over silica gel (eluent: cyclohexane/EtOAc 80/20). The pure fractions were collected and the solvent was evaporated, yielding 4.68 g (50%) of intermediate 24.

g) A Mixture of intermediate 24 (0.0104 mol) and 4-methyl-benzenesulfonic acid, hydrazide (0.0114 mol) in methanol (60 ml) was stirred at 50° C. overnight. The mixture was allowed to cool to room temperature. The precipitate was filtered off, washed with ethanol and dried, yielding 4.09 g (85%) of intermediate 25.

h) A mixture of intermediate 25 (0.00865 mol) in HCl 6N (40 ml) and THF (140 ml) was stirred at room temperature for 48 hours. The mixture was poured out on ice, basified with $K_2CO_3$ 10% and extracted with EtOAc. The organic layer was separated, dried, filtered and the solvent was evaporated. The residue was purified by column chromatography over silica gel (eluent: $CH_2Cl_2$/EtOAc 95/5). The pure fractions were collected and the solvent was evaporated, yielding 1.2 g (33%) intermediate 26.

i) $NaBH_4$ (0.00344 mol) was added at room temperature to a solution of intermediate 26 (0.00286 mol) in TBF (10 ml) and methanol (10 ml). The mixture was stirred at room temperature for 15 min. $H_2O$ was added and the mixture was extracted with $CH_2Cl_2$. The organic layer was separated, dried, filtered and the solvent was evaporated, yielding 1.2 g of intermediate 27.

j) A mixture of intermediate 27 (0.00286 mol) in $CH_2Cl_2$ (20 ml) was stirred at 0° C. under $N_2$. $SOCl_2$ (5 ml) was added. The mixture was stirred at 10° C. for 1 hour. solvent was evaporated, yielding intermediate 28.

Example A12

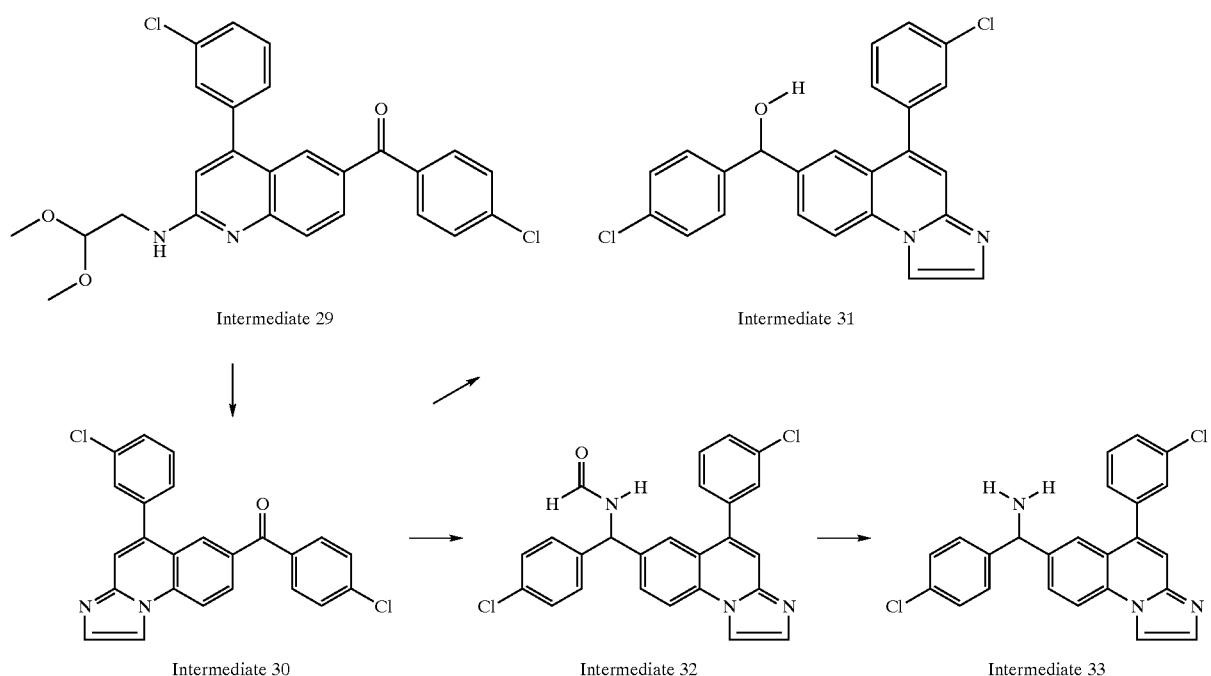

a) A mixture of intermediate 29, prepared analogous to example A1 (0.0727 mol), in acetic acid (90 ml) and xylene (300 ml) was stirred and for 72 h. The solvent was evaporated. The residue was taken in $CH_2Cl_2$, $K_2CO_3$ 10% was added and filtered over celite. The organic layer was decanted, dried, filtered and the solvent was evaporated. The residue was purified by column chromatography over silica gel (eluent: $CH_2Cl_2/CH_3OH$ 99/1). The pure fractions were collected and the solvent was evaporated. The residue was recrystallized from $CH_3CN$. The precipitate was filtered off and dried, yielding 6.7 g (56%) intermediate 30.

b) $NaBH_4$ (0.0086 mol) was added portionwise at 10° C. to a solution of intermediate 30 (0.00719 mol) in methanol (30 ml) and THF (20 ml). The mixture was stirred at ° C. for 15 min. Water was added and the mixture was concentrated. The concentrate was taken up in $CH_2Cl_2$. The organic layer was separated, washed with water, dried, filtered and the solvent was evaporated. The residue was crystallized from 2-propanone. The precipitate was filtered off and dried, yielding 1.45 g (48%) of intermediate 31.

c) A mixture of intermediate 30 (0.0096 mol) in formamide (19 ml) and acetic acid (20 ml) was stirred at 160° C. for 48 hours. The mixture was cooled. Ice was added. The mixture was extracted with $CH_2Cl_2$ and decanted. The organic layer was dried, filtered and the solvent was evaporated, yielding 4.2 g of intermediate 32.

d) A mixture of intermediate 32 (0.0096 mol) in HCl 3N (60 ml) and 2-propanol (60 ml) was stirred at 80° C. for 2.5 hours. The mixture was poured out on ice, basified with $NH_4OH$ and extracted with $CH_2Cl_2$. The organic layer was separated, dried, filtered and the solvent was evaporated. The residue was purified by column chromatography over silica gel (eluent: $CH_2Cl_2/CH_3OH/NH_4OH$ 98/2/0.1). The pure fractions were collected and the solvent was evaporated. The residue was crystallized from $CH_3CN$ and DIPE. The precipitate was filtered off and dried, yielding 1.15 g (29%) of intermediate 33.

Example A13

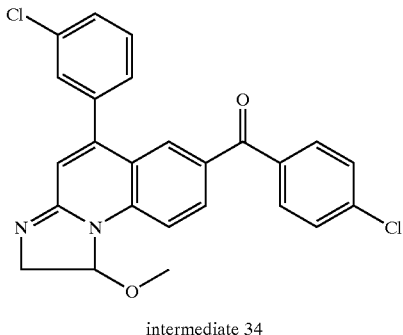

intermediate 34

A mixture of intermediate 29 (0.0472 mol) in acetic acid (30 ml) and xylenes (200 ml) was stirred and refluxed for 48 hr. The solvent was evaporated. The residue was taken up in $CH_2Cl_2$, washed with $K_2CO_3$ 10%, dried, filtered and the solvent was evaporated. The residue was purified by column chromatography over silica gel (eluent: $CH_2Cl_2/CH_3OH_4OH$ 99/1/0.1). The pure fractions were collected and the solvent was evaporated, yielding 15.6 g (75%) of intermediate 34.

B. PREPARATION OF THE FINAL COMPOUNDS

Example B1

A mixture of intermediate (2) (0.0207 mol) in acetic acid (10 ml) and mixed xylenes (100 ml) was stirred and refluxed for 12 hours and cooled. The mixture was evaporated and the residue was taken up in water, basified with NaOH (2N) and extracted with $CH_2Cl_2$. The residue was purified by column chromatography over silica gel. The pure fractions were collected and evaporated. The residue was converted into the ethanedioic acid salt (2:3) in $C_2H_5OH/CH_3OH/2$-propanone, yielding 3.5 g (30%) of (±)-7-[(4-fluorophenyl)(1H-imidazol-1-yl)methyl]-5-phenylimidazo[1,2-a]quinoline ethanedioate(2:3). hemihydrate; mp. 204.3° C. (comp. 3).

Example B2

Preparation of

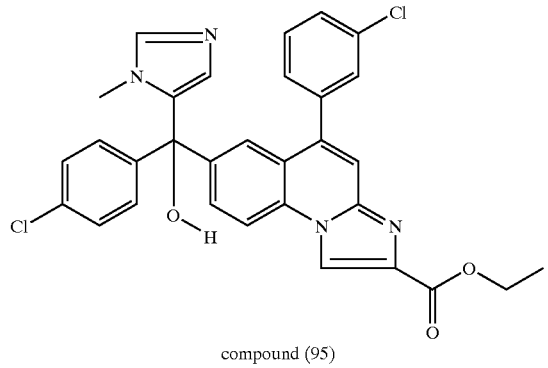

compound (95)

A mixture of intermediate (4) (0.0019 mol) in ethanol (5 ml) was stirred at 80° C. for 5 hours, then cooled and taken up in $CH_2Cl_2$. The organic solution was washed with $K_2CO_3$ (10%), dried, filtered and the solvent was evaporated. The residue was purified by column chromatography over silica gel. The pure fractions were collected and the solvent was evaporated. The residue was crystallized from 2-propanone and DIPE. The precipitate was filtered off and dried yielding 0.14 g (12%) of compound (95); mp. 143° C.

Example B3

A mixture of intermediate (5) (0.029 mol) and formylhydrazine (0.043 mol) in butanol (150 ml) was stirred and refluxed for 48 hours. The mixture was evaporated, the residue was taken up in $CH_2Cl_2$ and washed with water. The organic layer was dried, filtered off and evaporated. The residue was purified by column chromatography over silica gel. The pure fractions were collected and evaporated. The residue was dissolved in 2-propanone and converted into the ethanedioic acid salt (2:3) yielding 4.4 g (26.1%) of (±)-7-[(4-chlorophenyl)-1-imidazol-1-ylmethyl]-5-phenyl[1,2,4]-triazolo[4,3-a]quinoline ethanedioate(2:3).hemihydrate (comp. 5).

Example B4

A mixture of intermediate (7) (0.0071 mol) and triethyl orthoacetate (0.0086 mol) in n-butanol (35 ml) was stirred at 100° C. overnight. The solvent was evaporated. The residue was taken up in $CH_2Cl_2$, washed with $H_2O$ and with a saturated NaCl solution, dried, filtered and the solvent was evaporated. The residue was purified by column chromatography over silica gel. The pure fractions were collected and the solvent was evaporated. The residue was crystallized from 2-propanone. The precipitate was filtered off and dried yielding 1.95 g (53%) of (±)-5-(3-chlorophenyl)-α-(4-chlorophenyl)-1-methyl-α-(1-methyl-1H-imidazol-5-yl)-1,2,4-triazolo[4,3-a]quinoline-7-methanol (comp. 19).

Example B5

Preparation of

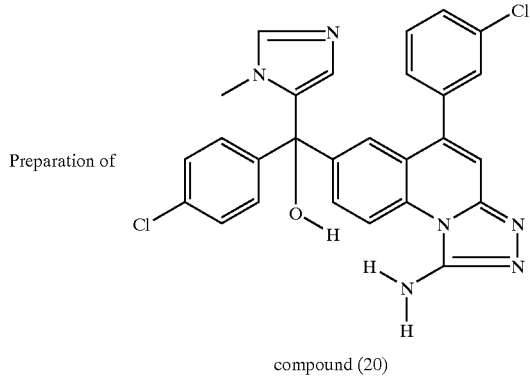

compound (20)

Cyanogen bromide (0.00815 mol) was added portionwise at 5° C. to a solution of intermediate (7) (0.00815 mol) in methanol (80 ml). The mixture was stirred at 60° C. for 10 minutes. and then brought to room temperature. The solvent was evaporated. The residue was taken up in $K_2CO_3$ 10%, filtered off, washed with $K_2CO_3$ (10%) and with $H_2O$ and dried. The residue was purified by column chromatography over silica gel. The pure fractions were collected and the solvent was evaporated. The residue was crystallized from THF/DPE. The precipitate was filtered off and dried yielding 1.45 g (34%) of compound (20).

Example B6

Preparation of

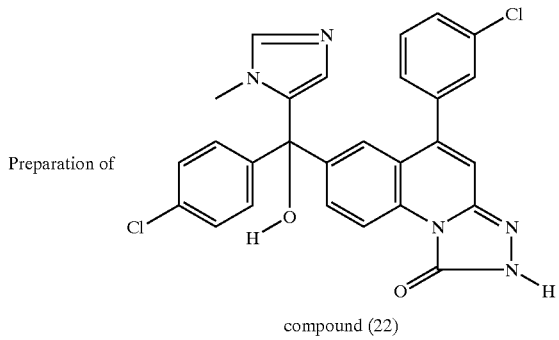

compound (22)

1,1'-carbonylbis-1H-imidazole (0.0055 mol) was added at room temperature to a solution of intermediate (7) (0.00367 mol) in THF (30 ml) and the mixture was stirred at room temperature for 30 min. Ice and then water were added, and the mixture was extracted twice with EtOAc. The combined organic layer was separated, dried, filtered and the solvent was evaporated. The residue was taken up in $CH_2Cl_2$. The precipitate was filtered off and dried. The residue was crystallized from THF/diethyl ether. The precipitate was filtered off and dried, yielding 0.85 g (45%) of compound (22).

Example B7

A mixture of intermediate (5) (0.029 mol) and ethyl carbazate (0.0436 mol) in 1-butanol (150 ml) was stirred and refluxed for one night. The mixture was evaporated in vacuo, the residue was taken up in $CH_2Cl_2$ and washed with water. The organic layer was dried, filtered off and evaporated. The residue was purified by column chromatography over silica gel. The pure fractions were collected and evaporated. The residue was dissolved in 2-propanone and converted into the ethanedioic acid salt (1:1) yielding 1 g (6.3%) of (±)-7-[(4-chlorophenyl)-1H-imidazol-1-ylmethyl]-5-phenyl[1,2,4]triazolo[4,3-a]quinolin-1(2H)-one ethanedioate(1:1).hemihydrate; mp. 198.3° C. (comp. 7).

Example B8

A mixture of intermediate (9) (0.006 mol) and sodium azide (0.018 mol) in DMF (20 ml) was stirred at 140° C. for 4 hours. The mixture was cooled to room temperature and poured out into ice water. The precipitate was filtered off, washed with $H_2O$ and taken up in $CH_2Cl_2$. The organic solution was dried, filtered and the solvent was evaporated. The residue was crystallized from $CH_3CN$ and 2-propanone. The precipitate was filtered off and dried yielding 1.2 g (38.2%) of (±)-5-(3-chlorophenyl)-α-(4-chlorophenyl)-α-(1-methyl-1H-imidazol-5-yl)tetrazolo[1,5-a]quinazoline-7-methanol; mp. 139° C. (comp. 29).

Example B9

A mixture of intermediate (11) (0.01 16 mol) and p-toluenesulfonhydrazide (0.0128 mol) in $CH_3OH$ (60 ml) was stirred at 60° C. for 2 hours and then brought to room temperature. $H_2O$ was added. The mixture was extracted with $CH_2Cl_2$. The organic layer was separated, dried, filtered and the solvent was evaporated. The residue was purified by column chromatography over silica gel. Two pure fractions were collected and their solvents were evaporated. The desired fraction was crystallized from 2-propanone and $CH_3CN$. The precipitate was filtered off and dried yielding 1.25 g (21%) of (±)-5-(3-chlorophenyl)-α-(4-chlorophenyl)-α-(1-methyl-1H-imidazol-5-yl)-[1,2,3]triazolo1,5-a]quinoline-7-methanol; mp. 222° C. (comp. 26).

Example B10

A mixture of compound (29) (0.008 mol) in methanol (60 ml) was cooled to 5° C. Sodium tetrahydroborate (0.008 mol) was added portionwise. The mixture was stirred at 5° C. for 1 hour, hydrolized, extracted with $CH_2Cl_2$ and decanted. The organic layer was dried, filtered and the solvent was evaporated. The residue was crystallized from 2-propanone. The precipitate was filtered off and dried yielding 1.8 g (44.6%) of (±)-5-(3-chlorophenyl)-α-(4-chlorophenyl)-4,5-dihydro-α-(1-methyl-1H-imidazol-5-yl)tetrazolo[1,5-a]quinazoline-7-methanol; mp. 212° C. (comp. 30).

Example B11

A dispersion of sodium hydride (80%) in a mineral oil (0.0083 mol) was added at 5° C. under $N_2$ flow to a mixture of intermediate (10) (0.007 mol) in DMT (33 ml). The mixture was stirred at 5° C. for 30 min. Iodomethane (0.008 mol) was added. The mixture was stirred at 5° C. for 30 minutes and then hydrolized. The precipitate was filtered off, washed with $H_2O$ and taken up in $CH_2Cl_2$. The organic solution was dried, filtered and the solvent was evaporated. The residue was purified by column chromatography over silica gel. The pure fractions were collected and the solvent was evaporated. The residue was crystallized from $CH_3CN$ and DIPE. The precipitate was filtered off and dried, yielding 0.8 g (22%) of (±)-5-(3-chlorophenyl)-α-(4-chlorophenyl)-4,5-dihydro 4-methyl-α-(1-methyl-1H-imidazol-5-yl)tetrazolo[1,5-a]quinazoline-7-methanol; mp. 235° C. (comp. 33).

Example B12

Preparation of

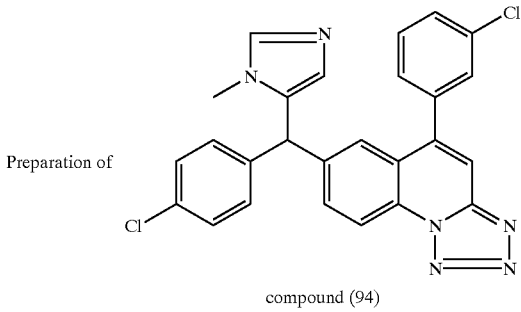

compound (94)

A mixture of (±)-5-(3-chlorophenyl)-α-(4-chlorophenyl)-α-(1-methyl-1H-imidazol-5-yl)tetrazolo[1,5-a]quinoline-7-methanol (0.005 mol) in formamide (10 ml) and acetic acid (20 ml) was stirred at 160° C. for 5 hours, poured out on ice, basified with $NH_4OH$ and extracted with $CH_2Cl_2$. The organic layer was separated, dried, filtered and the solvent was evaporated. The residue was purified by column chromatography over silica gel. The pure fractions were collected and the solvent was evaporated. The residue was crystallized from $CH_3CN$ and diethyl ether. The precipitate was filtered off and dried yielding 0.84 g (35%) of compound (94); mp. 166° C.

Example B13

Preparation of

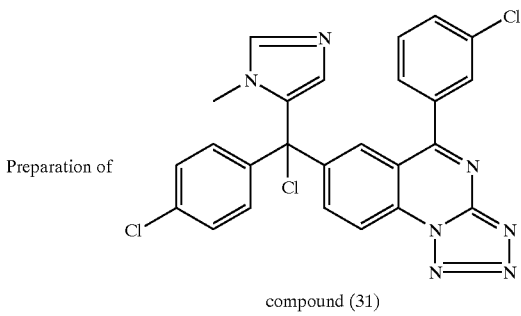

compound (31)

Compound (29) (0.006 mol) was added at a low temperature to thionyl chloride (30 ml). The mixture was stirred at 40° C. for 2 hours. The solvent was evaporated, yielding compound (31).

Example B14

A mixture of 2-propanol and $NH_3$ (35 ml) was added dropwise quickly at 0° C. to a mixture of compound (31) (0.006 mol) in THF (35 ml). The mixture was stirred at 5° C. for 30 min and then brought to room temperature. The solvent was evaporated. The residue was taken up in $CH_2Cl_2$ and $H_2O$ and the mixture was decanted. The organic layer was dried, filtered and the solvent was evaporated. The residue was purified by column chromatography over silica gel. The pure fractions were collected and the solvent was evaporated. The residue was crystallized from $CH_2Cl_2$ and DIPE. The precipitate was filtered off and dried yielding 0.6 g (20%) of (±)-5-(3-chlorophenyl)-α-(4-chlorophenyl)-α-(1-methyl-1H-imidazol-5-yl)tetrazolo[1,5-a]quinazoline-7-methanamine; mp. 159° C. (comp. 32).

Example B15 n-Butyllithium (0.0129 mol) was added slowly at −70° C. under $N_2$ flow to a solution of 1-methylimidazole (0.0129 mol) in THF (25 ml). The mixture was stirred for 30 min. Chlorotriethylsilane (0.0129 mol) was added. The mixture was allowed to warm to room temperature and then cooled to −70° C. n-Butyllithium (0.0129 mol) was added. The mixture was stirred at −70° C. for 1 hour, then allowed to warm to −15° C. and cooled to −70° C. A solution of (±)-α-(4-chlorophenyl)-5-phenylimidazo[1,2-a]quinoline-7-methanone (0.0107 mol) in THF (12 ml) was added. The mixture was stirred at −70° C. for 1 hour. Water was added. The mixture was extracted with EtOAc. The organic layer was separated, dried, filtered and the solvent was evaporated. The residue was purified by column chromatography over silica gel. The pure fractions were collected and the solvent was evaporated. The residue was crystallized from 2-propanone. The precipitate was filtered off and dried, yielding 0.9 g (18%) of (±)-α-(4-chlorophenyl)-α-(1-methyl-1-imidazol-5-yl)-5-phenylimidazo[1,2-a]quinoline-7-methanol (compound 11).

Example B16

Preparation of

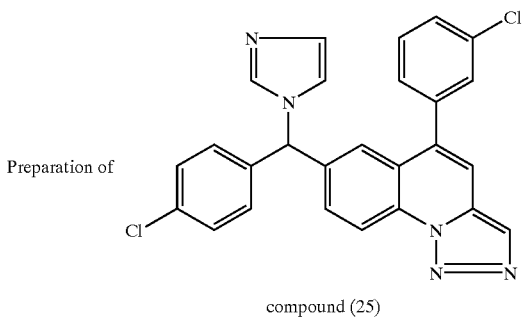

compound (25)

A mixture of intermediate 28 (0.00286 mol) and 1H-imidazole (0.017 mol) in $CH_3CN$ (20 ml) was stirred and refluxed for 48 hours and then brought to room temperature. $H_2O$ was added. The mixture was extracted with $CH_2Cl_2$. The organic layer was separated, dried, filtered and the solvent was evaporated. The residue was purified by column over silica gel (eluent: $CH_2Cl_2/CH_3OH/NH_4OH$ 98/2/0.1). The pure fractions were collected and the solvent was. The residue was crystallized from $CH_3CN$ and DIPE. The precipitate was filtered off and dried, yielding 0.55 g compound 25 (40%).

Example B17

Preparation of

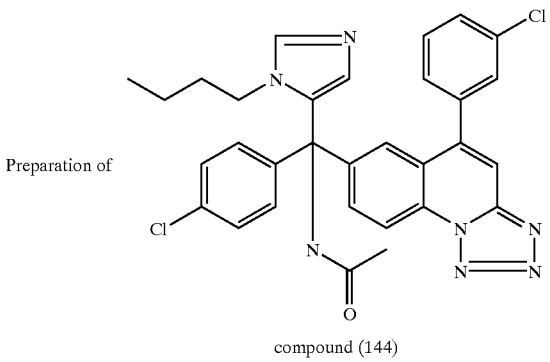

compound (144)

$H_2SO_4$ conc. (0.1 ml) was added dropwise to $CH_3CN$ (5 ml). Then compound (142) (0.00042 mol) was added portionwise. The mixture was stirred at 80° C. for 2 hours, brought to room temperature and poured out into ice water. EtOAc was added. The mixture was basified with $K_2CO_3$ 10% and extracted with EtOAc. The organic layer was separated, washed with $H_2O$, dried, filtered and the solvent was evaporated. The residue was purified by column chromatography over silica gel (eluent: $CH_2Cl_2/CH_3OH/NH_4OH$ 96/4/0.1; 15–40 μm). The pure fractions were collected and the solvent was evaporated. This fraction was crystallized from $CH_3CN$ and DIPE. The precipitate was filtered off and dried, yielding 0.11 g of compound (144) (44%).

Example B18

A mixture of compound 53 (0.00464 mol) in $SOCl_2$ (30ml) was stirred at 60° C. for 6 hours. The solvent was evaporated, yielding compound 76.

Example B19

A mixture of compound 16 (0.0022 mol) in 1,2-ethanediol (15 ml) and $H_2SO_4$ (conc.) (5 drops) was stirred and refluxed at 125° C. for 6 hours. $K_2CO_3$ 10% was added and the mixture was extracted with $CH_2Cl_2$. The organic layer was separated, dried, filtered, and the solvent was evaporated. The residue was purified by column chromatography over silica gel (eluent: toluene/2-propanol/$NH_4OH$ 88/12/0.8). The pure fractions were collected and the solvent was evaporated. The residue was converted into the ethanedioic acid salt (1:1) in 2-propanone and crystallized from $CH_3CN$/2-propanone. The precipitate was filtered off, washed with diethyl ether and dried. yielding 0.5 g of compound 41 (35%); mp. 150° C.

Example B20

4-(3-chlorophenyl)-$α^6$-(4-chlorophenyl)-2-hydrazino-$α^6$-(1-methyl-1H-imidazol-5-yl)-3,6-quinolinedimethanol (0.00371 mol) was added to HCl 1N (25 ml) and stirred at room temperature. A solution of $NaNO_2$ (0.00408 mol) in $H_2O$ (5 ml) was added dropwise and the resulting reaction mixture was stirred and refluxed for one hour. The mixture was allowed to cool to room temperature, then poured out into ice-water and the precipitate was filtered off, washed with water, washed with diethyl ether and dried, yielding 1.95 g of compound 82 (92%; mp: >280 ° C.).

Example B21

HCl 3N (20 ml) was added dropwise to a solution of compound 51 (0.0123 mol) in $H_2O$ (80 ml) (until pH=2). The mixture was stirred for 1 hour. The precipitate was filtered off and dried, yielding 5 g of compound 53 (70%); mp. >260° C.

Example B22

$NH_2CH_3$ (2.5 ml) was added dropwise at room temperature to a mixture of compound and compound 47 (0.0086 mol) in THF (45 ml). The mixture was stirred at 40° C. for 30 min, hydrolized and extracted with $CH_2Cl_2$. The organic layer was separated, dried, filtered and the solvent was evaporated. The residue was purified by column chromatography over silica gel (eluent: toluene/2-propanol/$NH_4OH$ 85/15/1). Three fractions were collected and their solvents were evaporated. Fraction I was crystallized from $CH_3CN$ and DIPE. The precipitate was filtered off and dried, yielding 0.4 g of compound 48 (9%); mp. 167° C. Fraction 2 was crystallized from $CH_3CN$ and diethyl ether. The precipitate was filtered off and dried, yielding 0.6 g of compound 49 (13%); mp. 206° C.

Example B23

(R)-1-(1-isocyanatoethyl)naphthalene (0.0039 mol) was added to a mixture of compound 18 (0.00196 mol) in THF (10 ml). The mixture was stirred and refluxed for 18 hours, hydrolized and extracted with $CH_2Cl_2$. The organic layer was separated, dried, filtered and the solvent was evaporated. The residue was purified by column chromatography over silica gel (eluent: cyclohexane/2-propanol/$NH_4OH$ 70/30/1). The pure fractions were collected and the solvent was evaporated. The residue was crystallized from $CH_3CN$ and DIPE. The precipitate was filtered off and dried, yielding 0.55 g of compound 135 (40%).

Example B24

Compound 18 (0.008 mol) was purified and separated into its enantiomers by chiral column chromatography over Chiralcel OD (eluent: ethanol 100%). Two pure fractions were collected and their solvents were evaporated. Fraction 1 was converted into the ethanedioic acid salt (1:1). The precipitate was filtered off and dried, yielding 1.59 g of compound 28 (34%); mp. 180° C. Fraction 2 was converted into the ethanedioic acid salt (1:1) and crystallized from ethanol. The precipitate was filtered off and dried, yielding 1.85 g of compound 27 (39%); mp. 1 72° C.

Example B25

$K_2CO_3$ (0.096 mol) was added at 5° C. to a mixture of hydroxylamine hydrochloride (0.09 mol) in $H_2O$ (10m). The mixture was stirred for 15 min. A solution of compound 69 (0.003 mol) in THF (15 ml) was added dropwise. The mixture was stirred at 5° C. for 30 min. Ice water was added and the mixture was extracted with $CH_2Cl_2$. The organic layer was separated, dried, filtered and the solvent was evaporated. The residue was purified by column chromatography over silica gel (eluent: $CH_2Cl_2/CH_3OH/NH_4OH$ 95/5/0.3). The pure fractions were collected and the solvent was evaporated. The residue was crystallized from EtOAc. The precipitate was filtered off and dried, yielding 0.17 g of compound 98 (11%); mp. 191° C.

Example B26

$NH_4OH$ conc. (10 ml) was added dropwise at 5° C. to a mixture of compound 76 (0.00464 mol) in THF (20 ml). The mixture was stirred at room temperature for 2 hours, poured out on ice and extracted with $CH_2Cl_2$. The organic layer was separated, dried, filtered and the solvent was evaporated. The residue was purified by column chromatography over silica gel (eluent: $CH_2Cl_2/CH_3OH/NH_4OH$ 95/5/0.1). Two pure fractions were collected and their solvents were evaporated. Fraction 1 was crystallized from $CH_3CN$ and DIPE. The precipitate was filtered off and dried, yielding 0.55 g of compound 77 (21%); mp. >250° C. Fraction 2 was purified by column chromatography over silica gel (eluent: $CH_2Cl_2/CH_3OH/NH_4OH$ 95/5/0.5; 20–45 μm). The pure fractions were collected and the solvent was evaporated. The residue was crystallized from $CH_3CN$. The precipitate was filtered off and dried, yielding 0.17 g of compound 80 (6%); mp. >250° C.

Example B27

Methanamine (30 ml; 40% in $H_2O$) was added to a mixture of compound 119 (0.004 mol) in THF (20 ml). The mixture was stirred for 1 hour. $K_2CO_3$ 10% was added and the mixture was extracted with $CH_2Cl_2$. The organic layer was separated, dried, filtered and the solvent was evaporated. The residue was purified by column chromatography over silica gel (eluent: $CH_2Cl_2/CH_3OH/NH_4OH$ 90/10/0.1 and 80/20/0.1). The pure fractions were collected and the solvent was evaporated. The residue was crystallized from THF and diethyl ether. The precipitate was filtered off and dried, yielding 0.17 g of compound 121 (48%); mp. 224° C.

Example B28

LiAlH$_4$ (0.00663 mol) was added at 5° C. under N$_2$ flow to THF (30 ml). Then compound 52 (0.00331 mol) was added portionwise. The mixture was stirred at room temperature for 1 hour. EtOAc was added. The mixture was hydrolized cold, filtered over celite and washed with EtOAc. The filtrate was extracted with EtOAc. The organic layer was separated, washed with H$_2$O, dried, filtered and the solvent was evaporated. The residue was purified by column chromatography over silica gel (eluent: cyclohexane/2-propanol/NH$_4$OH 80/20/1). The pure fractions were collected and the solvent was evaporated. This fraction was crystallized from 2-propanone and diethyl ether. The precipitate was filtered off and dried, yielding 0.98 g of compound 75(51%).

The following compounds were prepared analogous to the one of the above examples (the example number analogous to which they were prepared is indicated between square brackets after the compound number).

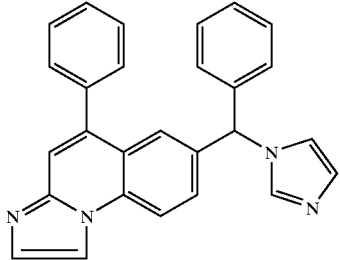

Ethanedioate (2:3) Hydrate (2:1)
Comp 1[B1]; mp. 225° C.

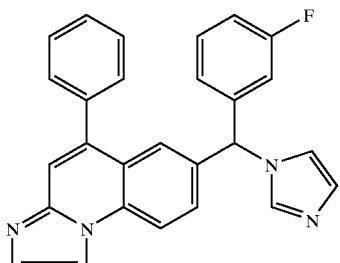

Ethanedioate (2:3) Hydrate (1:1)
Comp 2[B1]; mp. 203° C.

-continued

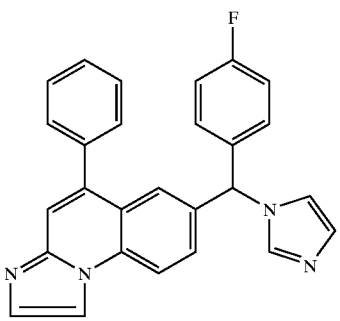

Ethanedioate (2:3) Hydrate (2:1)
Comp 3[B1]; mp. 204° C.

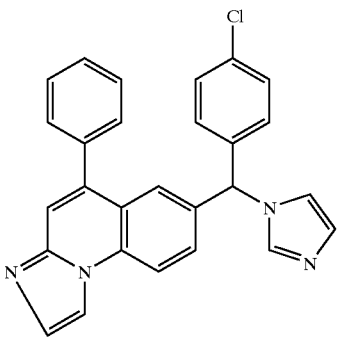

Ethanedioate (2:3) Hydrate (2:1)
Comp 4[B1]; mp. 202° C.

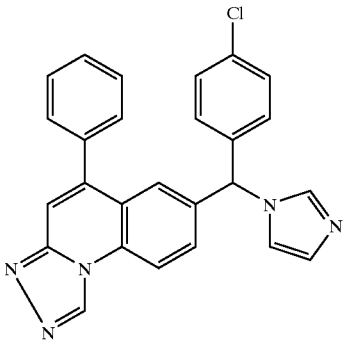

Ethanedioate (2:3) Hydrate (2:1)
Comp 5[B3]

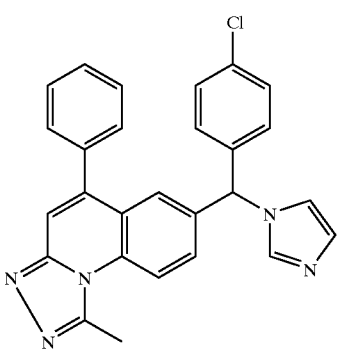

Comp 6[B3]; mp. 259° C.

-continued
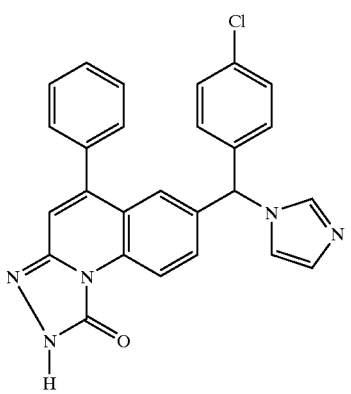
Ethanedioate (1:1) Hydrate (2:1)
Comp 7[B7]; mp. 198° C.
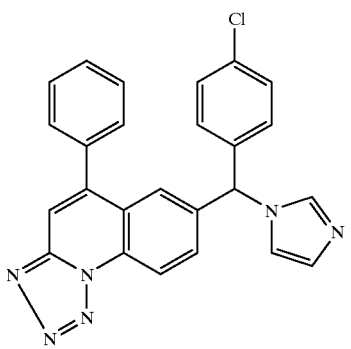
Ethanedioate (1:1)
Comp 8[B20]
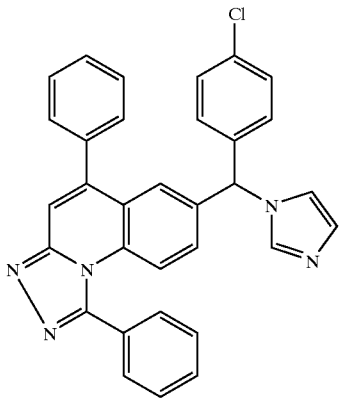
Ethanedioate (2:3)
Comp 9[B3]; mp. 194° C.
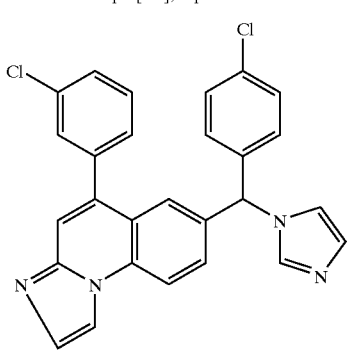
Comp 10[B1]; mp. 131° C.
-continued
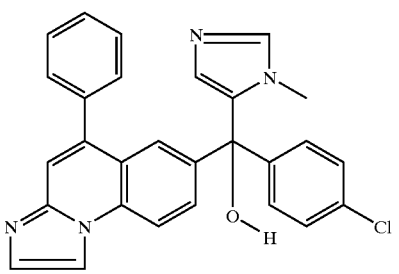
Comp 11[B15]
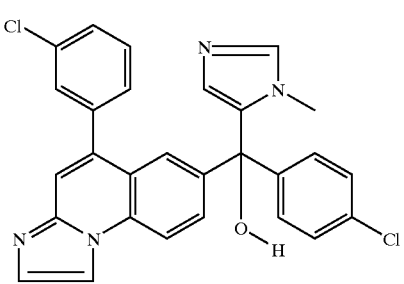
Comp 12[B15]
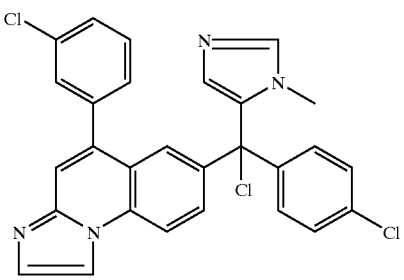
Hydrochloride (1:2)
Comp 13[B13]
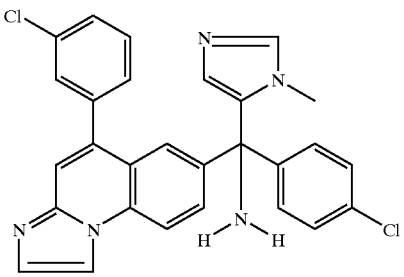
Ethanedioate (1:2) Hydrate (2:3)
Comp 14[B14]
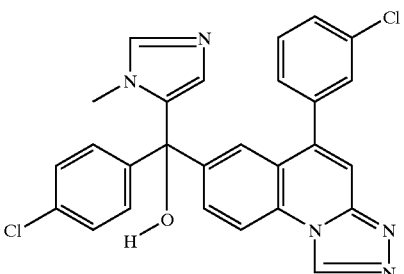
Ethanedioate (1:1)
Comp 15[B15]

-continued
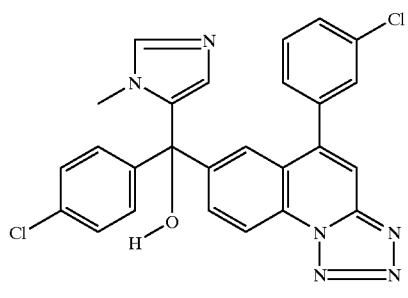
Comp 16[B8]
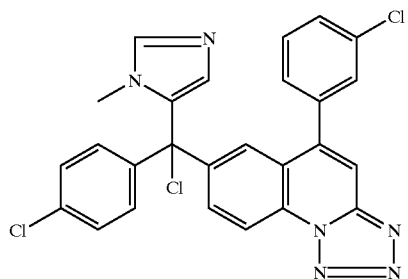
Hydrochloride (1:1)
Comp 17[B13]
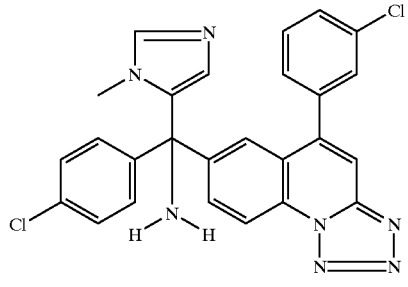
Comp 18[B14]
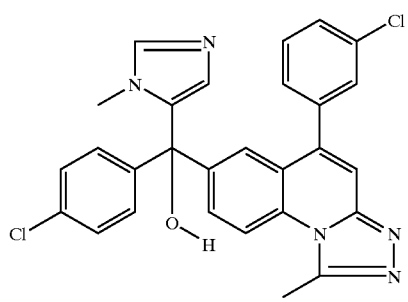
Comp 19[B4]
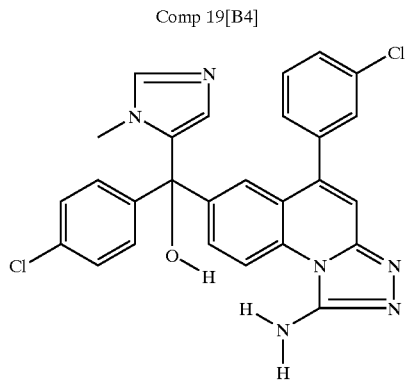
Comp 20[B5]
-continued
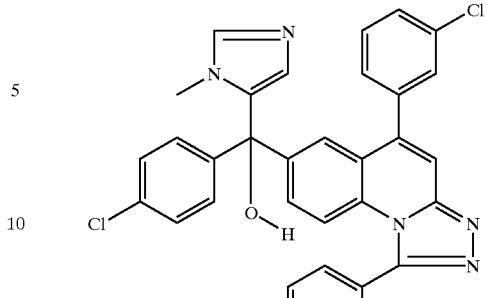
Comp 21[B4]
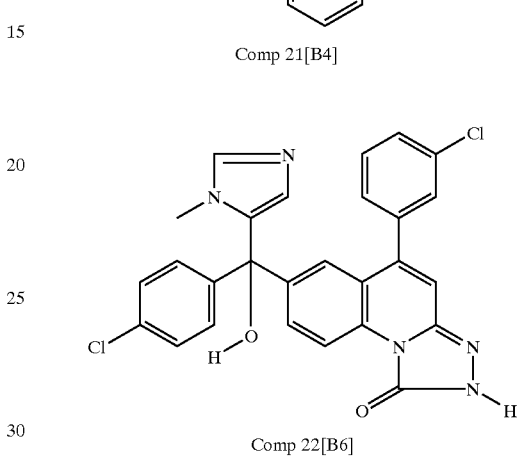
Comp 22[B6]
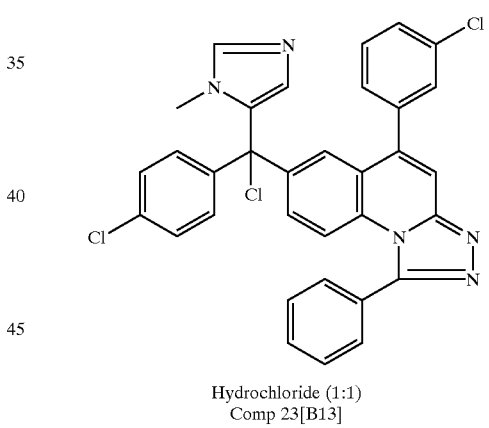
Hydrochloride (1:1)
Comp 23[B13]
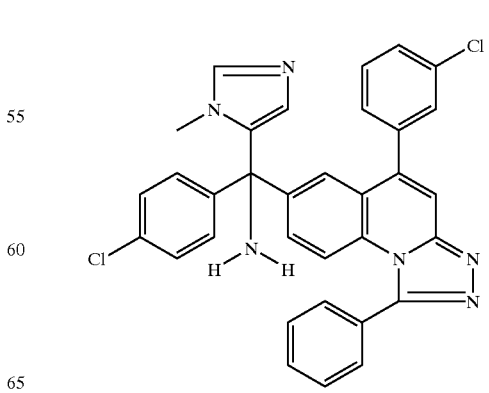
Comp 24[B14]

-continued
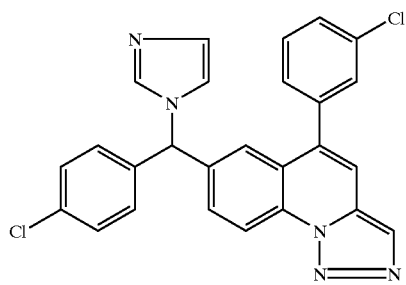
Comp 25[B16]; mp. 242° C.
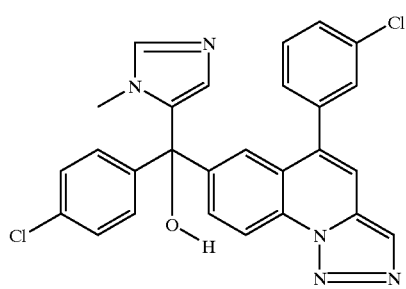
Comp 26[B9]; mp. 222° C.
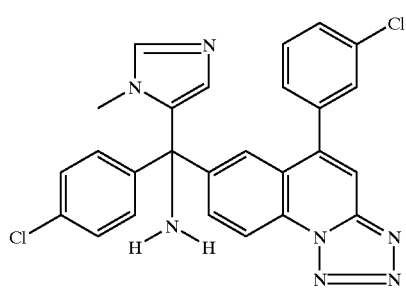
(B) Ethanedioate (1:1)
Comp 27[B24]; mp. 172° C.
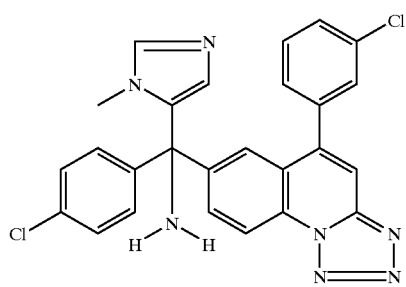
(A) Ethanedioate (1:1)
Comp 28[B24]; mp. 180° C.
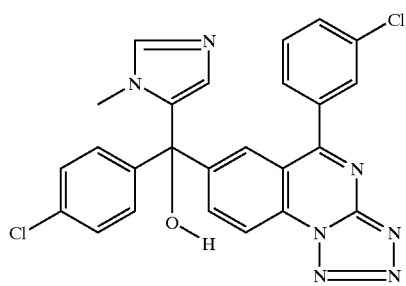
Comp 29[B8]; mp. 139° C.
-continued
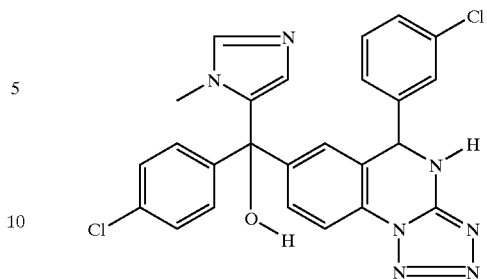
Comp 30[B10]; mp. 212° C.
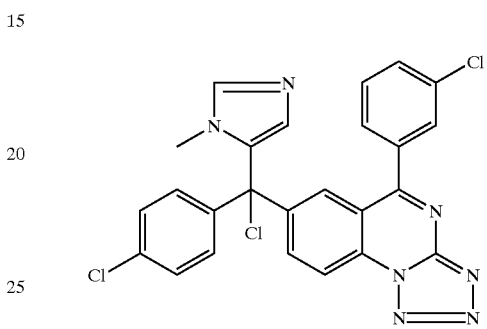
Hydrochloride (1:1)
Comp 31[B13]
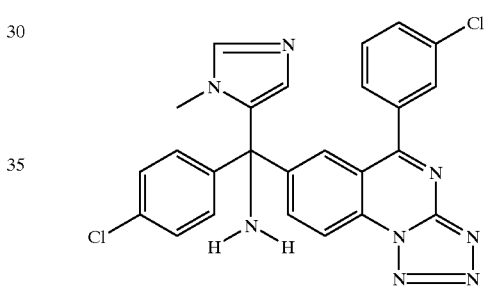
Comp 32[B14]; mp. 159° C.
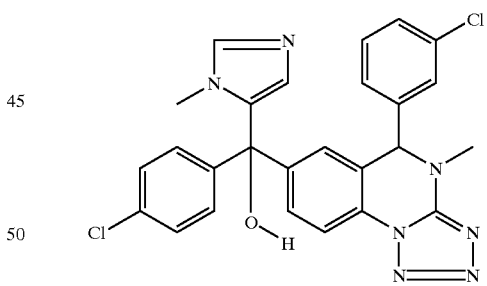
Comp 33[B11]; mp. 235° C.
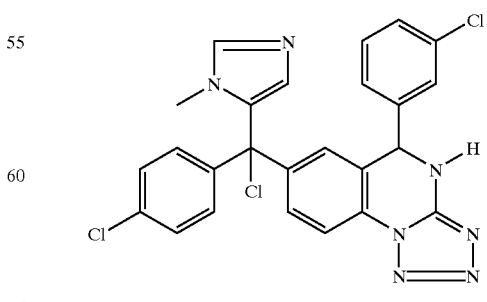
Hydrochloride (1:1)
Comp 34[B13]

-continued
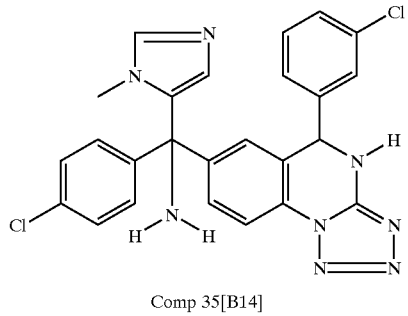
Comp 35[B14]
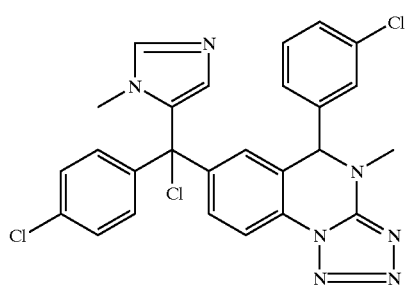
Hydrochloride (1:1)
Comp 36[B13]
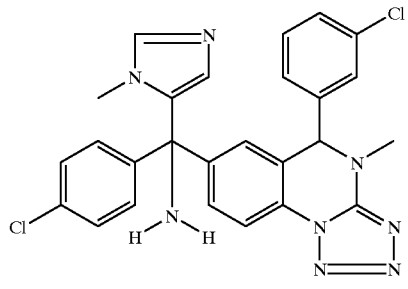
Comp 37; mp. 237° C.[B14]
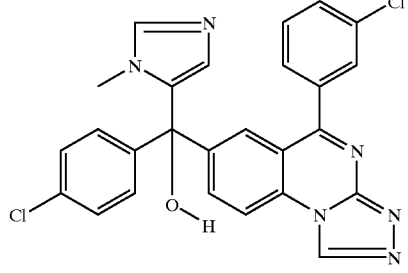
Comp 38[B3]; mp. >260° C.
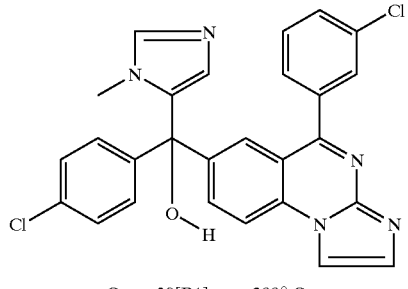
Comp 39[B1]; mp. 200° C.
-continued
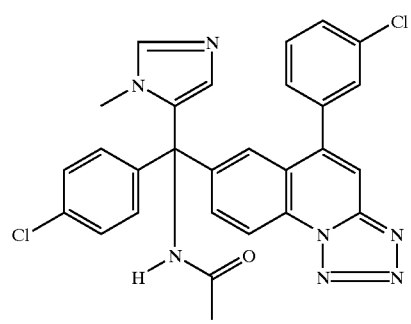
Comp 40[B17]; mp. >260° C.
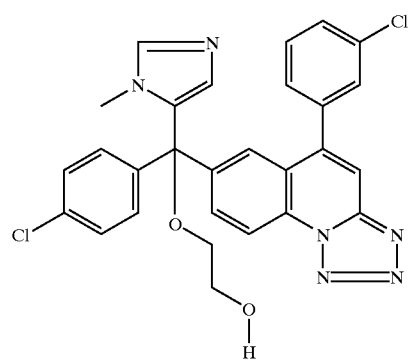
Ethanedioate (1:1) Hydrate (1:1)
Comp 41[B19]; mp. 150° C.
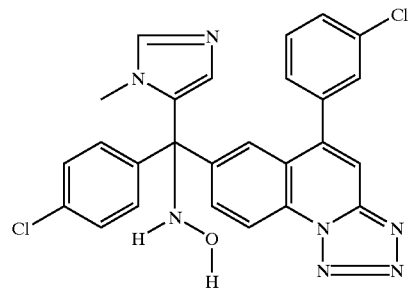
Comp 42[B25]; mp. 205° C.
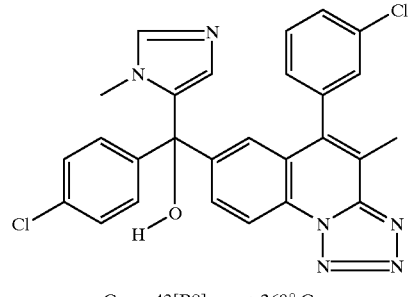
Comp 43[B8]; mp. >260° C.

-continued
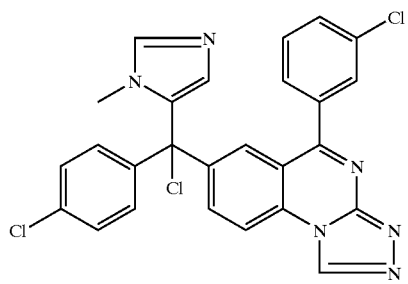
Hydrochloride (1:1)
Comp 44[B13]
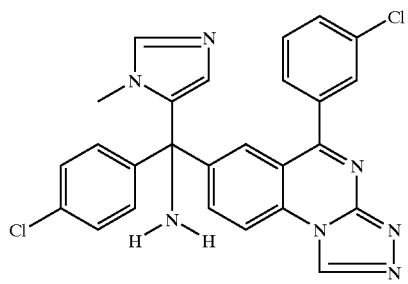
Comp 45[B14]; mp. 217° C.
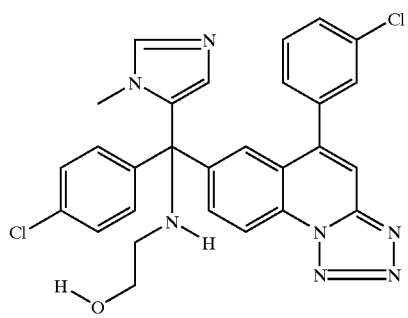
Comp 46[B25]; mp. 214° C.
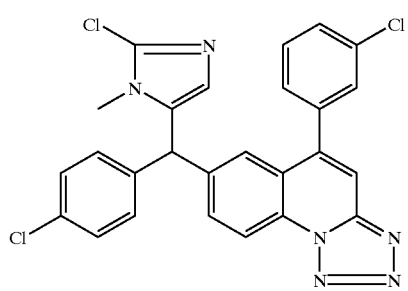
Hydrochloride (1:1)
Comp 47[B13]
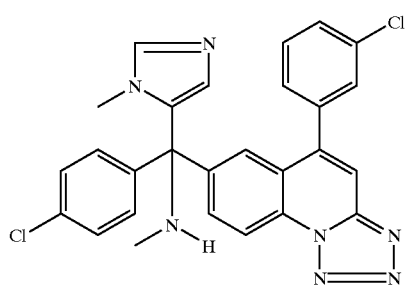
Comp 48[B14]; mp. 167° C.
-continued
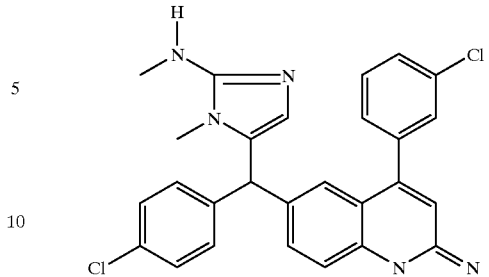
Comp 49[B22]; mp. 206° C.
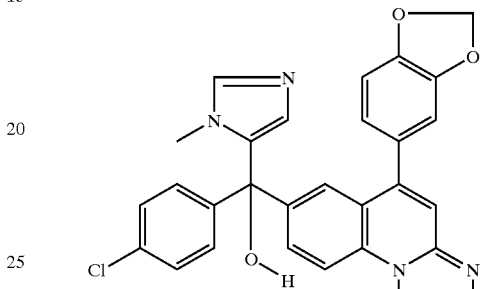
Comp 50[B8]; mp. 255° C.
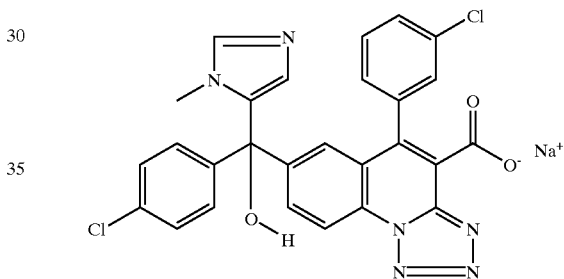
Comp 51[B8]
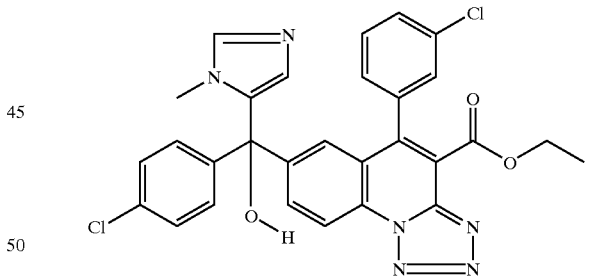
Comp 52[B8]; mp. >260° C.
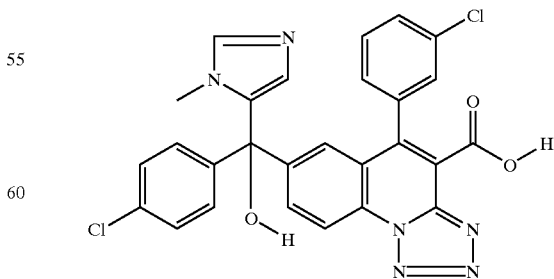
Hydrochloride (1:1)
Comp 53[B21]; mp. >260° C.

-continued
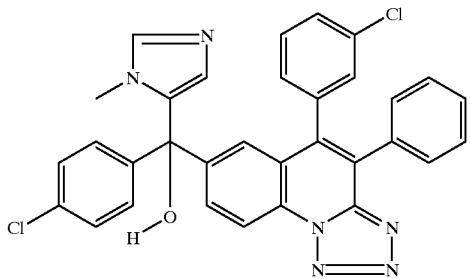
Comp 54[B8]
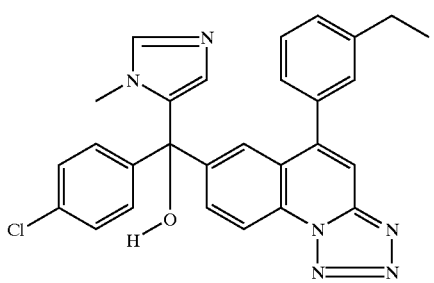
Comp 55[B8]; mp. 245° C.
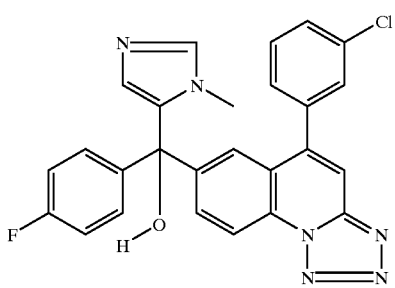
Comp 56[B8]; mp. 204° C.
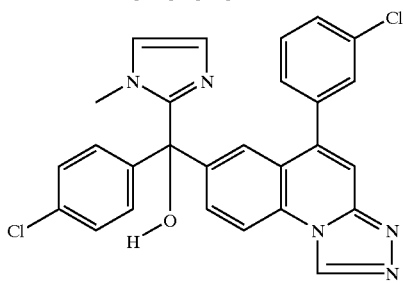
Hydrate (1:1)
Comp 57[B3]
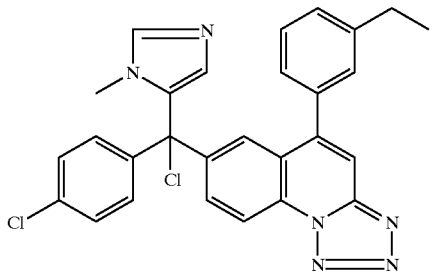
Hydrochloride (1:1)
Comp 58[B13]
-continued
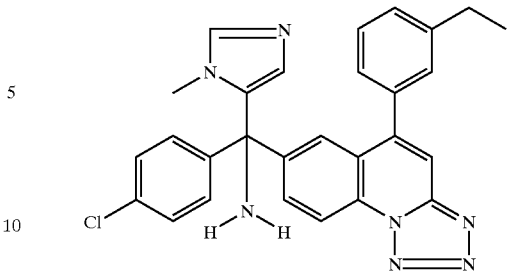
Comp 59[B14]; mp. 131° C.
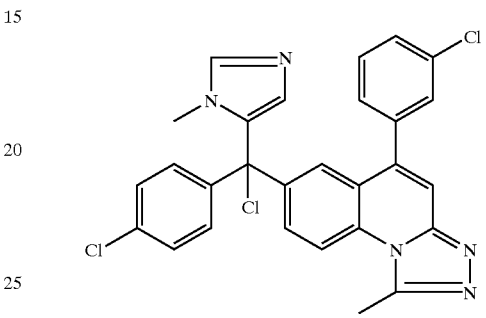
Hydrochloride (1:1)
Comp 60[B13]
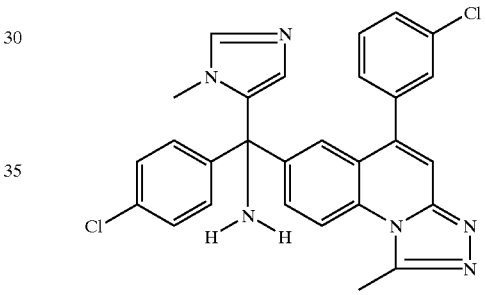
Hydrate (1:1)
Comp 61[B14]; mp. 199° C.
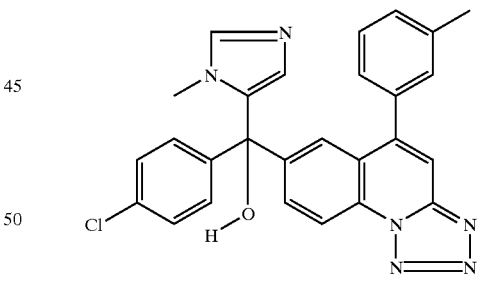
Comp 62[B8]; mp. 218° C.
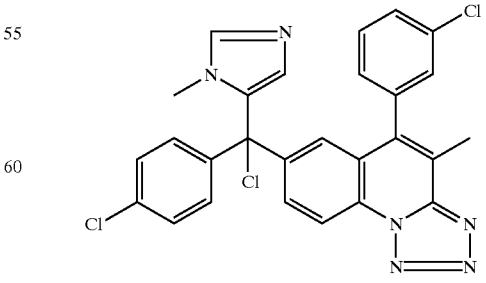
Hydrochloride (1:1)
Comp 63[B13]

-continued
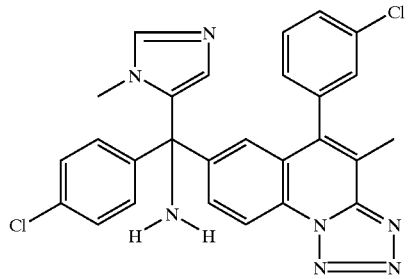
Comp 64[B14]; mp. >260° C.
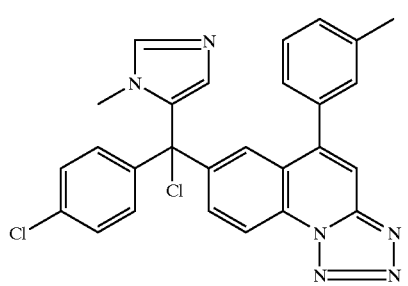
Hydrochloride (1:1)
Comp 65[B13]
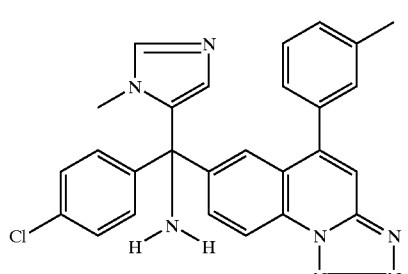
Comp 66[B14]; mp. 213° C.
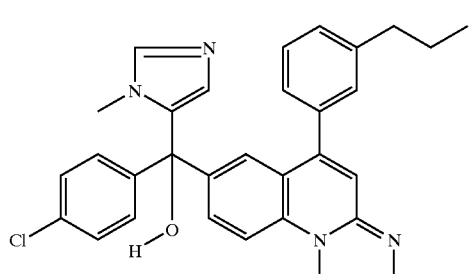
Comp 67[B8]; mp. 222° C.
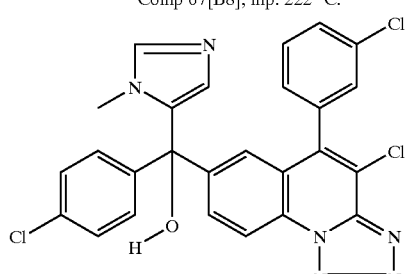
Comp 68[B8]; mp. >260° C.
-continued
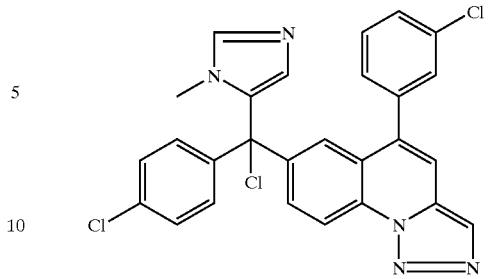
Hydrochloride (1:1)
Comp 69[B13]
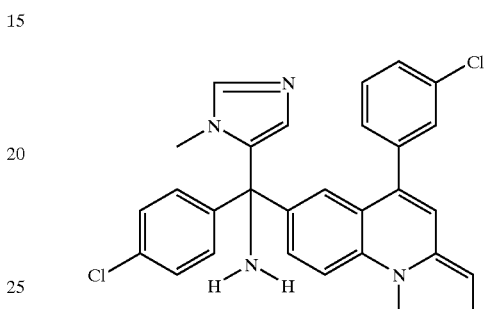
Comp 70[B14]; mp. 231° C.
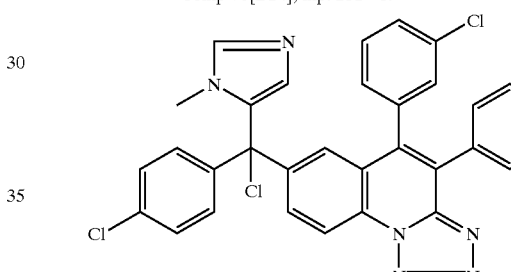
Hydrochloride (1:1)
Comp 71[B13]
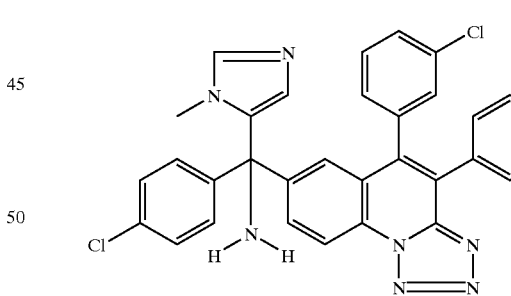
Comp 72[B14]; mp. >260° C.
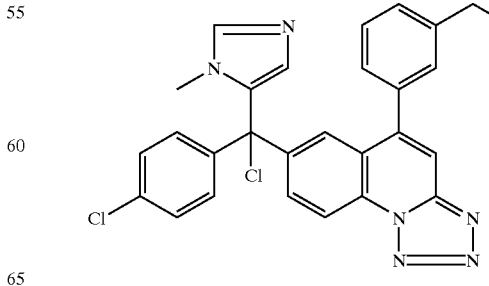
Hydrochloride (1:1)
Comp 73[B13]

-continued
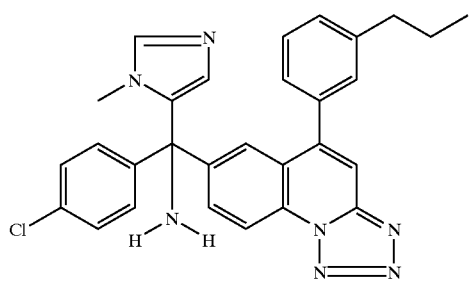
Comp 74[B14]; mp. 163° C.
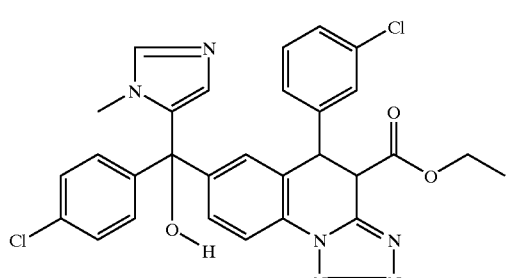
Comp 75[B28]; mp. 215° C.
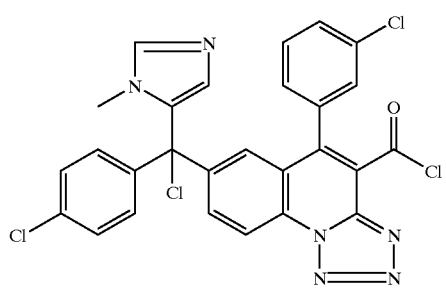
Hydrochloride (1:1)
Comp 76[B18]
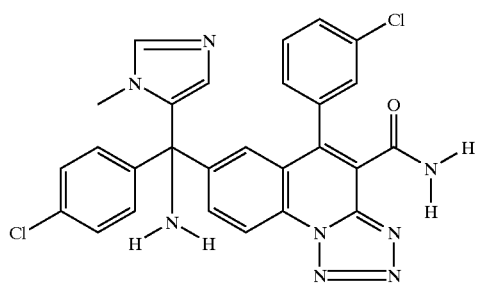
Comp 77[B26]; mp. >250° C.
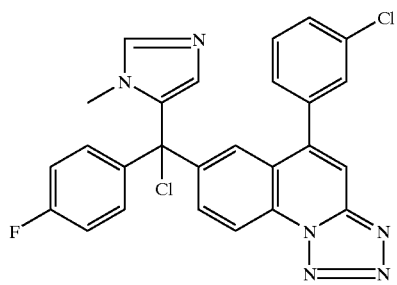
Hydrochloride (1:1)
Comp 78[B13]
-continued
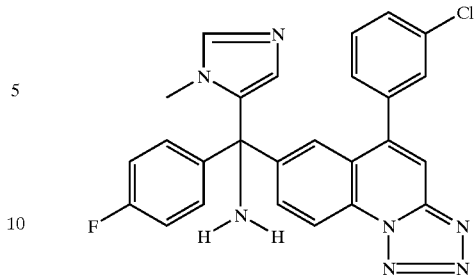
Comp 79[B14]; mp. 216° C.
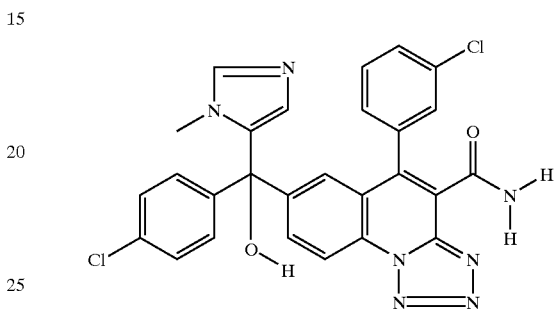
Comp 80[B26]; mp. >250° C.
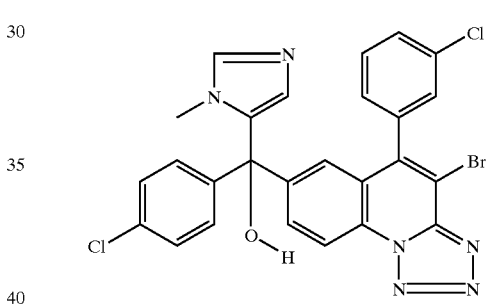
Comp 81[B20]; mp. 280° C.
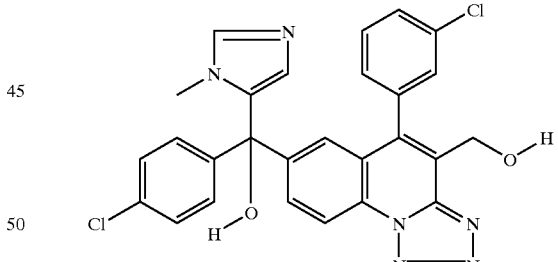
Hydrochloride (1:1)
Comp 82[B20]; mp. >280° C.
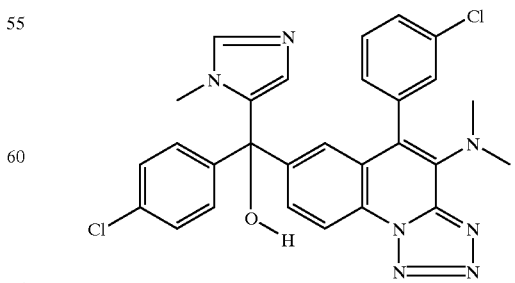
Comp 83[B8]; mp. 270° C.

-continued
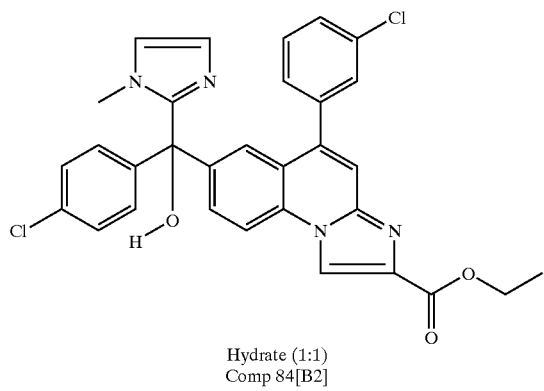
Hydrate (1:1)
Comp 84[B2]
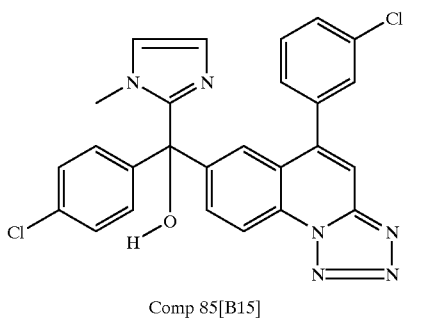
Comp 85[B15]
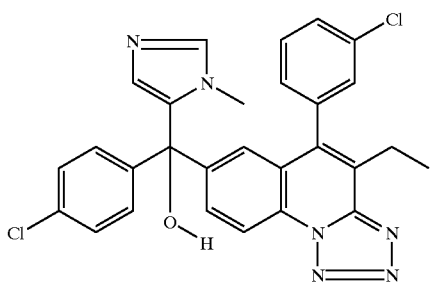
Comp 86[B8]; mp. 260° C.
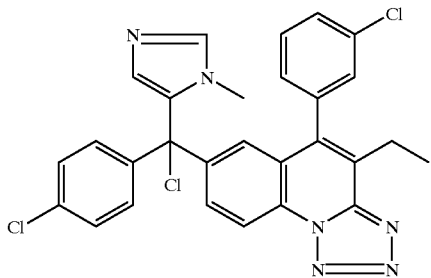
Hydrochloride (1:1)
Comp 87[B13]
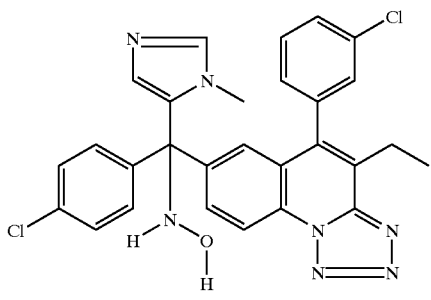
Comp 88[B25]; mp. 220° C.
-continued
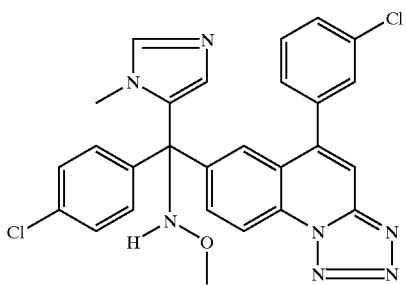
Comp 89[B25]; mp. 157° C.
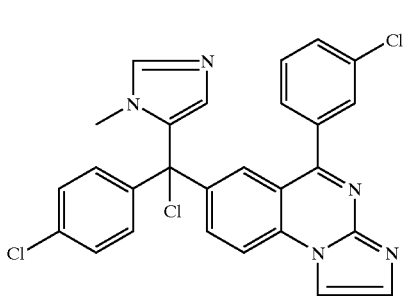
Hydrochloride (1:2)
Comp 90[B13]
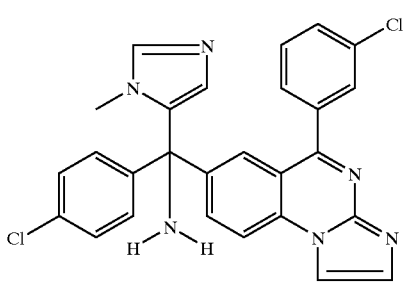
Hydrate (1:1)
Comp 91[B14]; mp. 173° C.
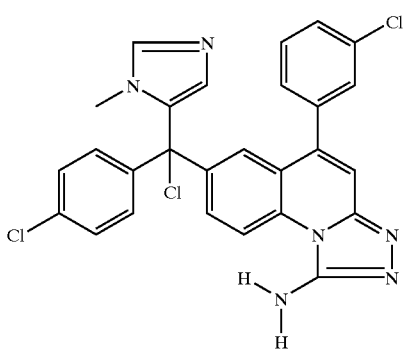
Hydrochloride (1:2)
Comp 92[B13]

-continued
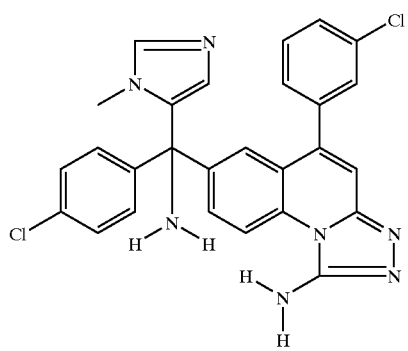
Ethanedioate (2:5) Hydrate (1:2)
Comp 93[B14]; mp. 208° C.
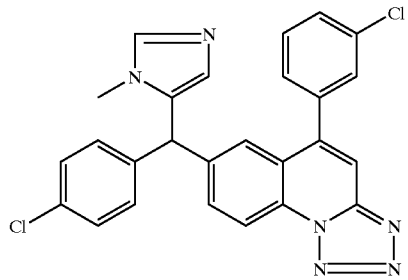
Comp 94[B12]; mp. 166° C.
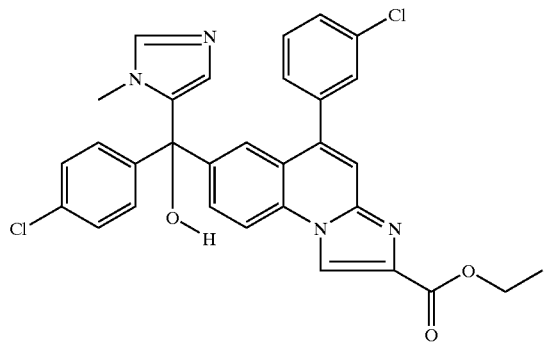
Comp 95[B2]; mp. 243° C.
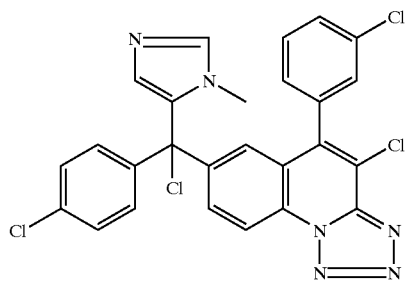
Hydrochloride (1:1)
Comp 96[B13]
-continued
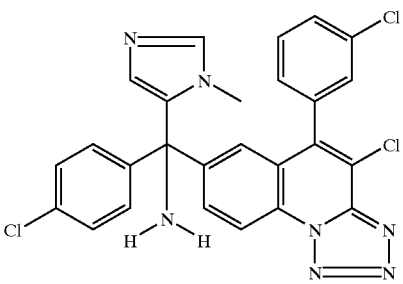
Comp 97[B14]; mp. 281° C.
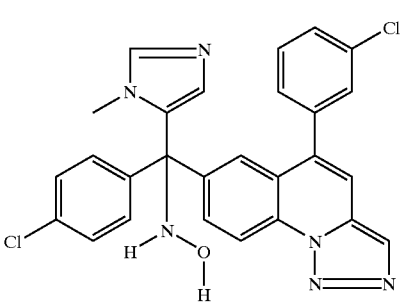
Comp 98[B25]; mp. 191° C.
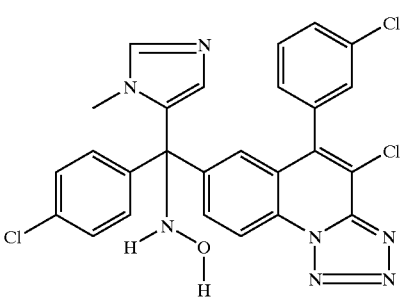
Comp 99[B25]; mp. 280° C.
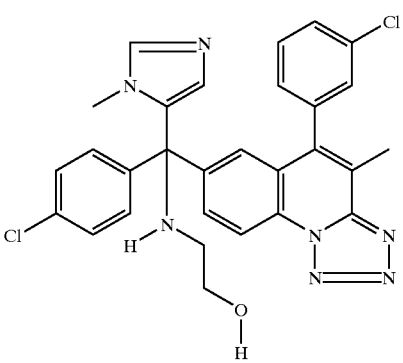
Comp 100[B25]; mp. 215° C.

-continued
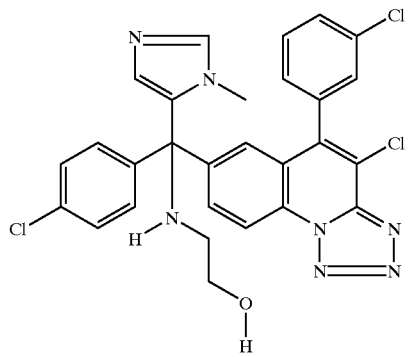
Comp 101[B25]; mp. 218° C.
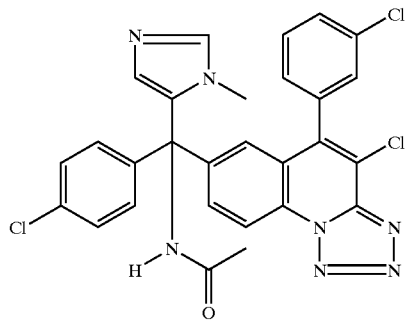
Comp 102[B17]; mp. 241° C.
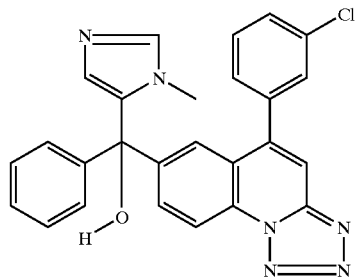
Comp 103[B20]; mp. 233° C.
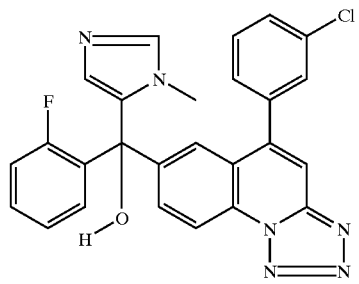
Comp 104[B8]; mp. 255° C.
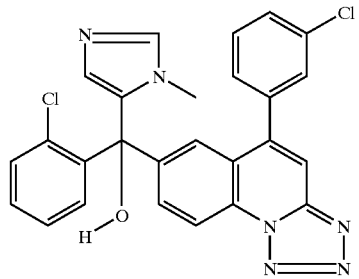
Comp 105[B20]; mp. 239° C.
-continued
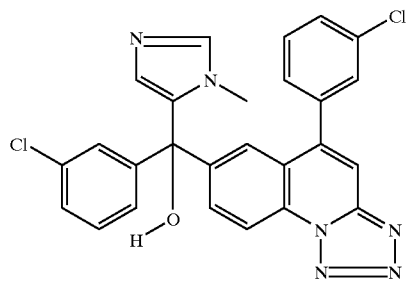
Comp 106[B8]; mp. 263° C.
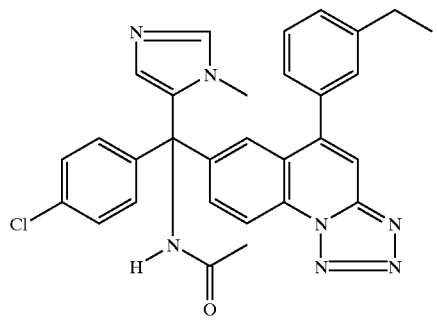
Comp 107[B17]; mp. 207° C.
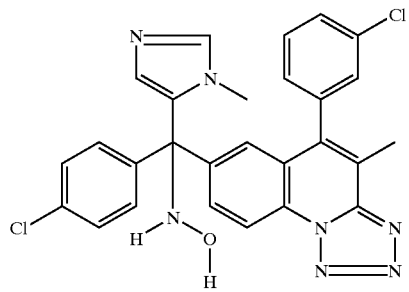
Comp 108[B25]; mp. 290° C.
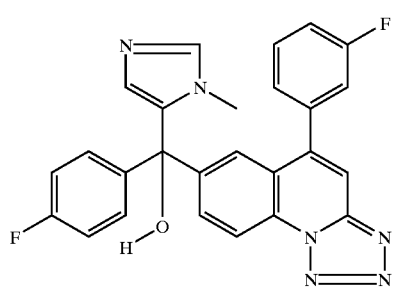
Comp 109[B8]; mp. 232° C.
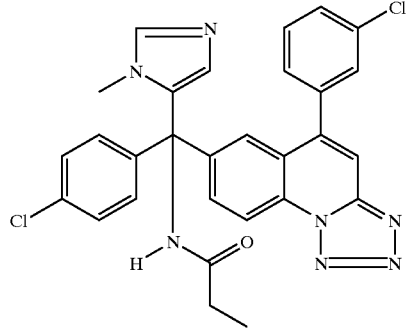
Comp 110[B17]; mp. 232° C.

-continued
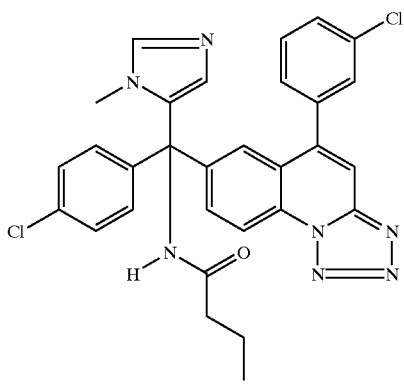
Comp 111[B17]; mp. 197° C.
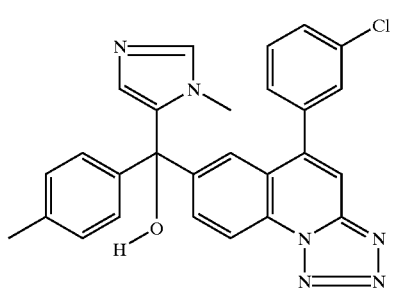
Comp 112[B8]; mp. 220° C.
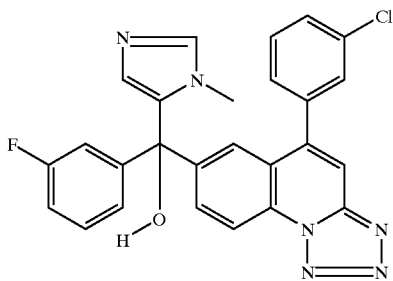
Comp 113[B8]; mp. 246° C.
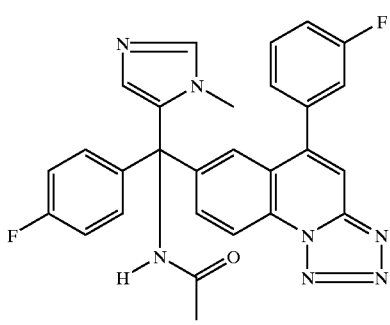
Comp 114[B17]; mp. 236° C.
-continued
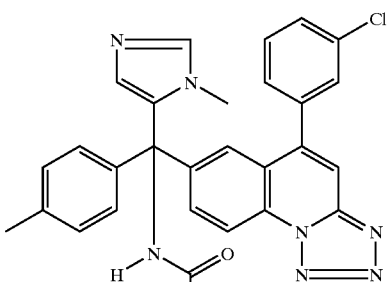
Comp 115[B17]; mp. 245° C.
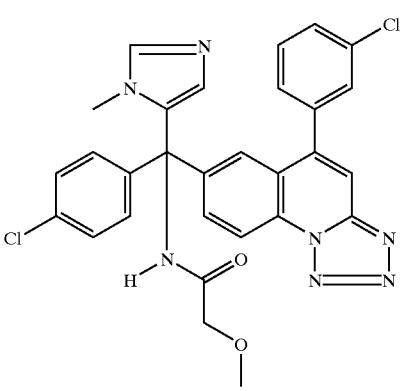
Comp 116[B17]; mp. 210° C.
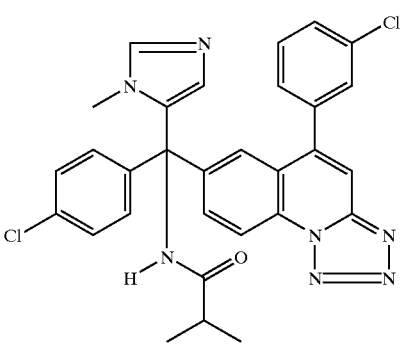
Comp 117[B17]; mp. 238° C.
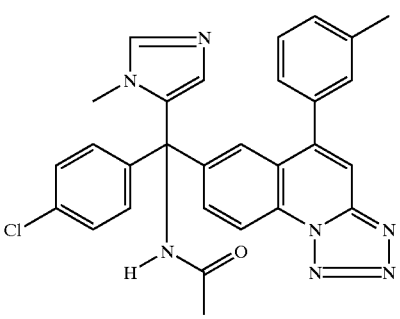
Comp 118[B17]; mp. 223° C.

-continued
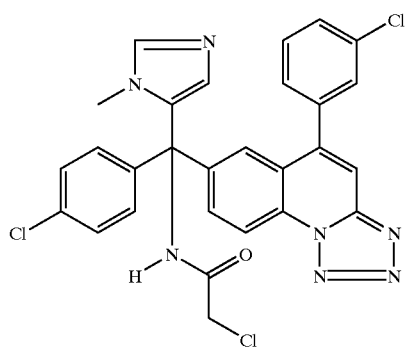
Sulfate (2:1)
Comp 119[B17]
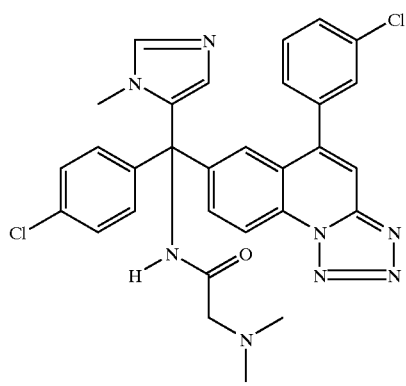
Comp 120[B27]; mp. 206° C.
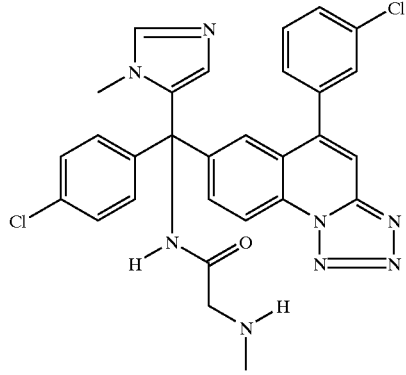
Comp 121[B27]; mp. 224° C.
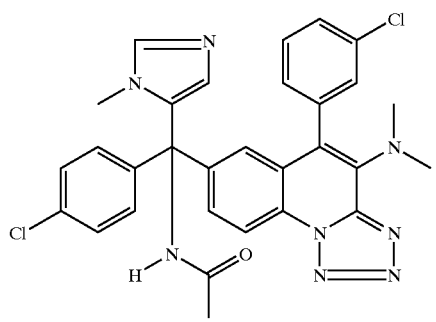
Comp 122[B17]; mp. >300° C.
-continued
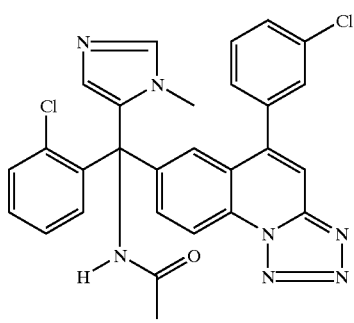
Comp 123[B17]; mp. 243° C.
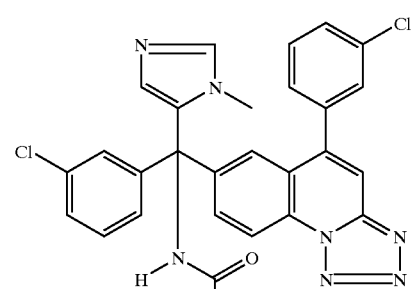
Comp 124[B17]; mp. 286° C.
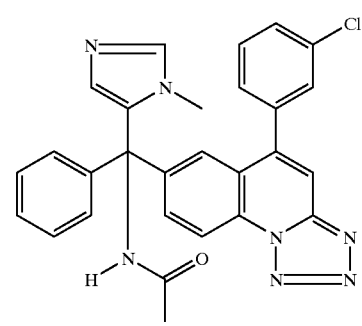
Hydrate (1:1)
Comp 125[B17]; mp. 235° C.
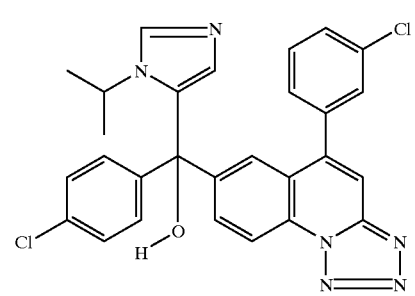
Comp 126; mp. 270° C.

-continued
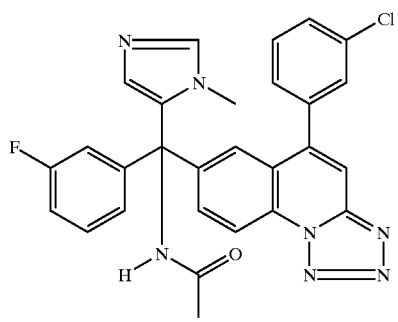
Comp 127[B17]; mp. 259° C.
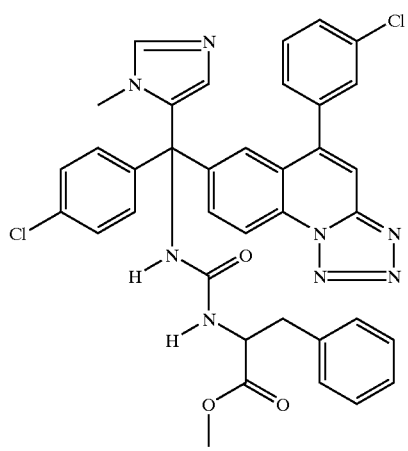
[R(R*,S*)] + [S(R*,R*)]
Comp 128[B23]; mp. 187° C.
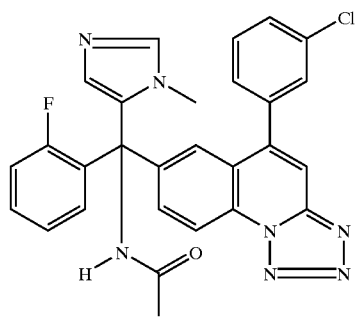
Comp 129[B17]; mp. 241° C.
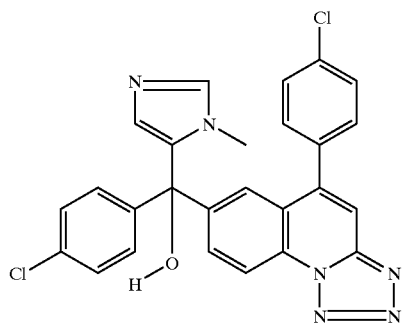
Comp 130[B8]; mp. 198° C.
-continued
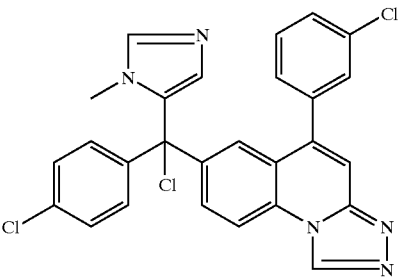
Hydrochloride (1:1)
Comp 131[B13]
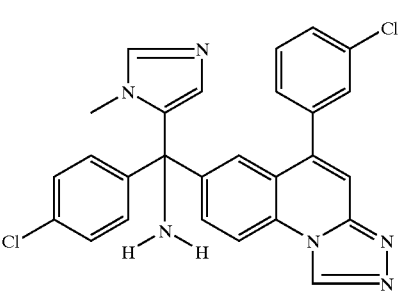
Comp 132[B14]; mp. 260° C.
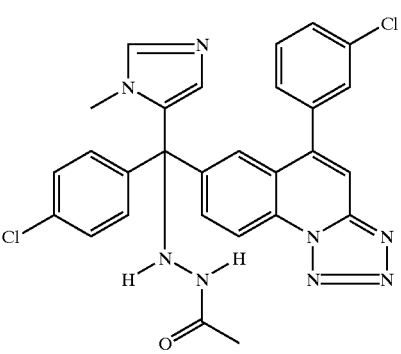
Comp 133[B25]; mp. 228° C.
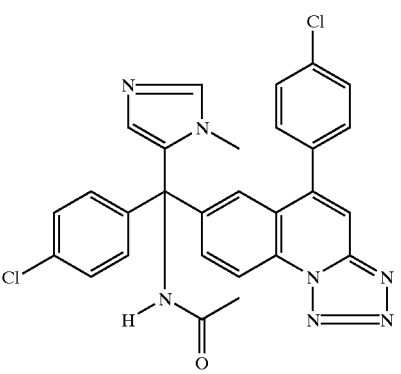
Comp 134[B17]; mp. 260° C.

-continued
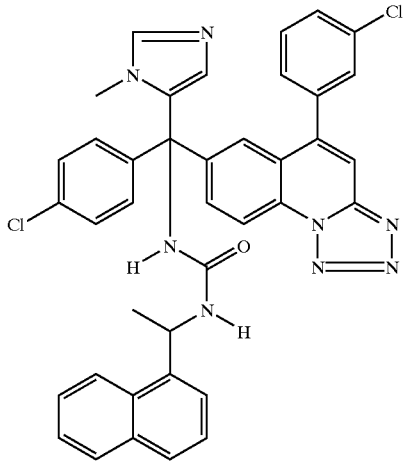
[R(R*,R*)] + [S(R*,S*)]
Comp 135[B23]; mp. 230° C.
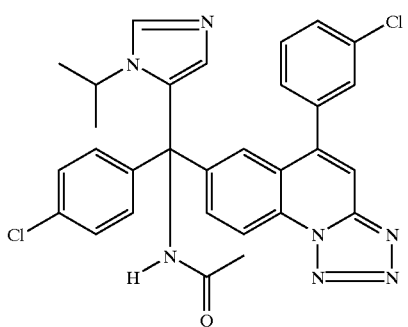
Comp 136[B17]; mp. 210° C.
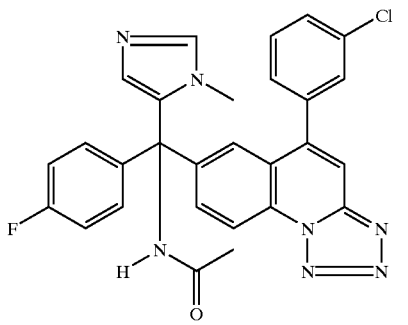
Hydrate (1:1)
Comp 137[B17]; mp. 217° C.
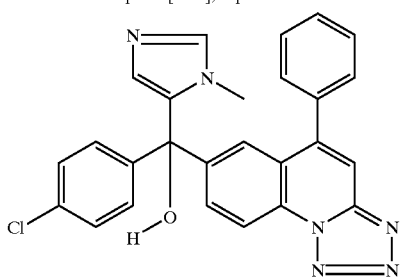
Comp 138[B8]; mp. 270° C.
-continued
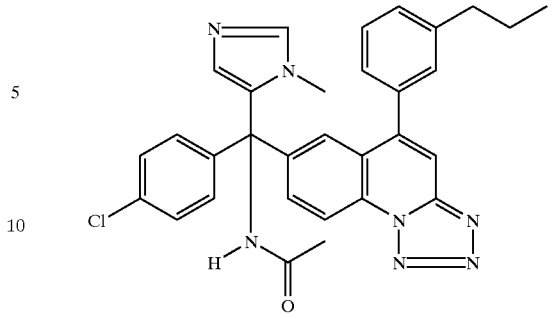
Hydrate (1:1)
Comp 139[B17]; mp. 185° C.
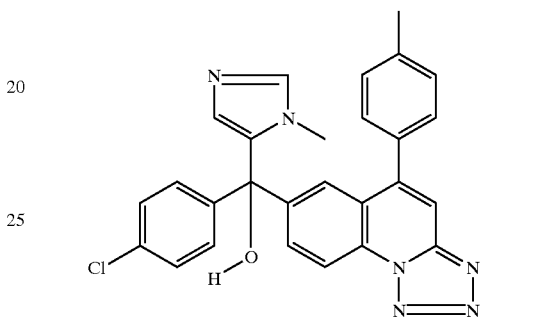
Comp 140[B8]
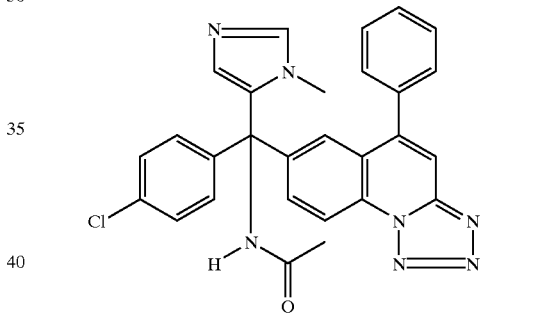
Comp 141[B17]
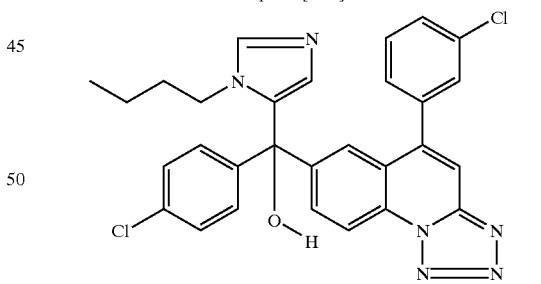
Comp 142[B8]; mp. 212° C.
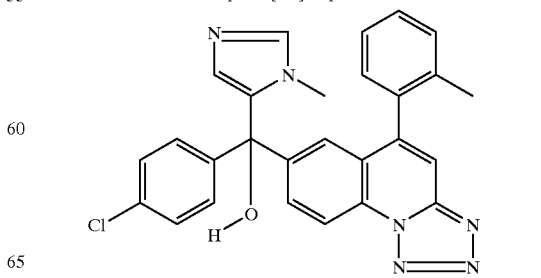
Comp 143[B8]; mp. >260° C.

-continued
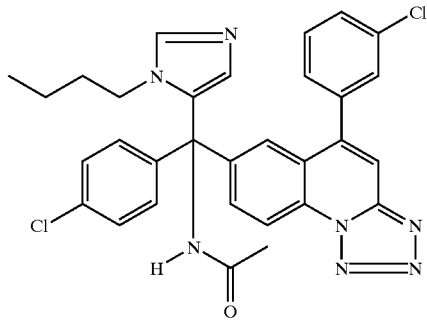
Comp 144[B17]
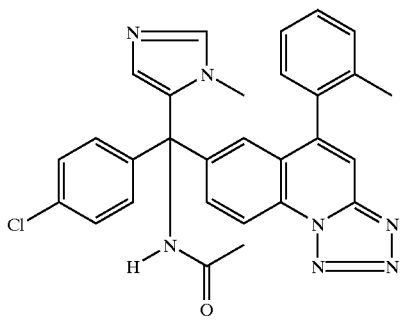
Comp 145[B17]
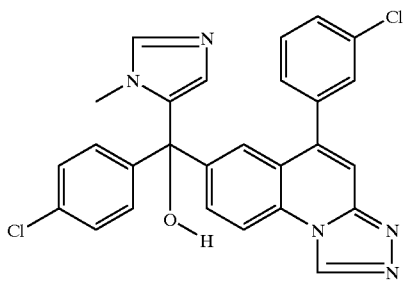
Comp 146[B15]
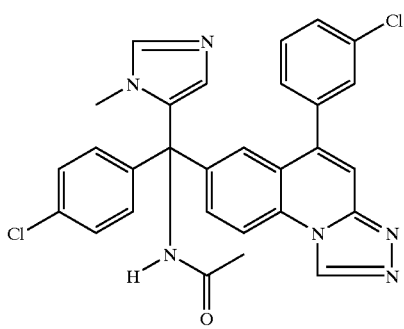
Comp 147[B17]
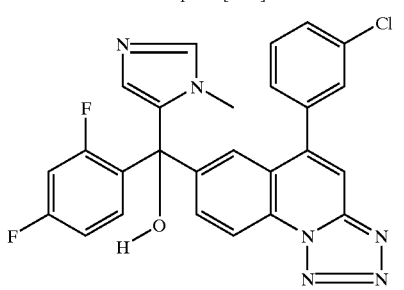
Comp 148[B8]
-continued
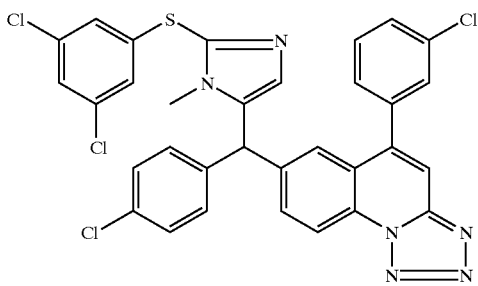
Comp 149
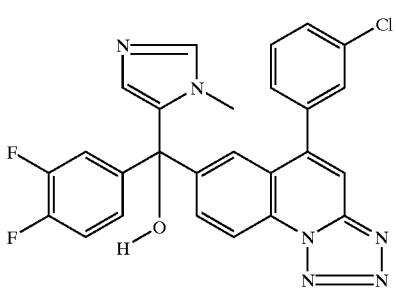
Comp 150[B8]
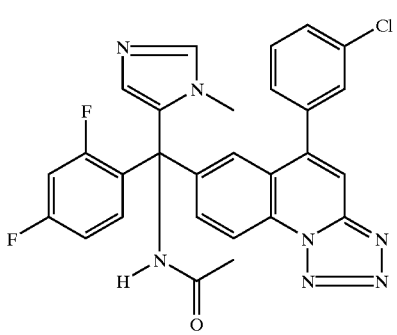
Comp 151[B17]
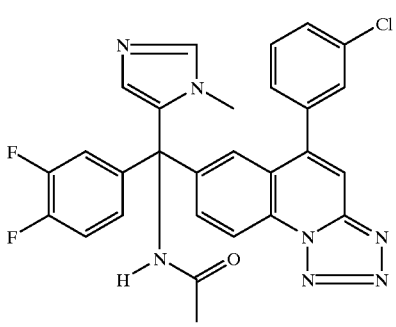
Comp 152[B17]
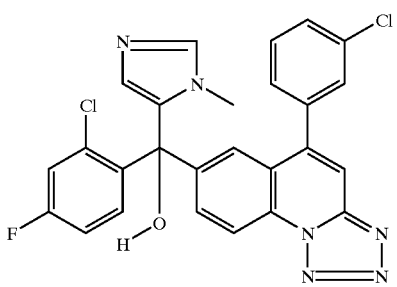
Comp 153[B8]

Comp 154[B17]

Comp 155[B8]

C. PHARMACOLOGICAL EXAMPLE

Example C.1

In Vitro Assay for Inhibition of Farnesyl Protein Transferase

An in vitro assay for inhibition of farnesyl transferase was performed essentially as described in WO 98/40383, pages 33–34.

Example C.2

Ras-Transformed Cell Phenotype Reversion Assay

The ras-transformed cell phenotype reversion assay was performed essentially as described in WO 98/40383, pages 34–36.

Example C.3

Farnesyl Protein Transferase Inhibitor Secondary Tumor Model

The farnesyl protein transferase inhibitor secondary tumor model was used as described in WO 98/40383, page 37.

Example C.4

Geranylgeranyltransferase Type I Assay

Background: The enzyme GGTase I catalyzes the covalent attachment of a C-20 geranylgeranyl moiety derived from geranylgeranyl pyrophosphate to the K-ras oncogene product $p_{21}^{K-ras}$. The geranylgeranylation proceeds via formation of a thioether linkage to a single, specific cysteine residue contained in a cys-A-A-X motif wherein A represents neutral amino acids and X represents a C-terminal leucine or methionine. Farnesylation of H,N, and K-ras isoforms by farnesyl protein transferase is required for activation and attachment of $p21^{ras}$ to plasma membranes.

However, the K-ras isoform, which is the dominant isoform of ras in human tumors, is also isoprenylated by GGTase I. Therefore, inhibitors of GGTase I may inhibit the aberrant growth of K-ras transformed human tumors which are resistant to protein farnesyltransferase inhibitors.

Methods: Compounds were screened in vitro using GGTase I enzyme prepared from Kirsten virus transformed human osteosarcoma (KHOS) cells. The assay measures the covalent attachment of radioactivity from [$^3$H]-geranylgeranyl pyrophosphate to the K-ras peptide substrate biotinKKKKKKSKTLCVIM or biotinYRASNRSCAIL substrate.

Measurements: Percent control GGTase I activity.

Derived Variables: Control enzyme activity=[CPM $^3$H-geranylgeranyl peptide product in the presence of vehicle solvent]

Test compound concentration=10 $\mu$M. Test compound % control activity=(CPM $^3$H-geranylgeranyl peptide product in the presence of test compound/control enzyme activity) X 100%

Standard Conditions: Compounds were dissolved in DMSO at a concentration of 20 mM. Further dilutions were prepared in DMSO. The final concentration of DMSO in the assay medium was 10%. The compound concentration tested for screening was 10 $\mu$M.

D. COMPOSITION EXAMPLE

Film-coated Tablets

Preparation of Tablet Core

A mixture of 100 g of a compound of formula (1), 570 g lactose and 200 g starch is mixed well and thereafter humidified with a solution of 5 g sodium dodecyl sulfate and 10 g polyvinyl-pyrrolidone in about 200 ml of water. The wet powder mixture is sieved, dried and sieved again. Then there are added 100 g microcrystalline cellulose. and 15 g hydrogenated vegetable oil. The whole is mixed well and compressed into tablets, giving 10.000 tablets, each comprising 10 mg of a compound of formula (I).

Coating

To a solution of 10 g methyl cellulose in 75 ml of denaturated ethanol there is added a solution of 5 g of ethyl cellulose in 150 ml of dichloromethane. Then there are added 75 ml of dichloromethane and 2.5 ml 1,2,3-propanetriol. 10 g of polyethylene glycol is molten and dissolved in 75 ml of dichloromethane. The latter solution is added to the former and then there are added 2.5 g of magnesium octadecanoate, 5 g of polyvinyl-pyrrolidone and 30 ml of concentrated colour suspension and the whole is homogenized. The tablet cores are coated with the thus obtained mixture in a coating apparatus.

What is claimed is:

1. A compound of formula (I)

or a pharmaceutically acceptable acid addition salt or a stereochemically isomeric form thereof, wherein =X¹—X²—X³— is a trivalent radical of formula
=N—CR⁶=CR⁷— (x-1),
=N—N=CR⁶— (x-2),
=N—NH—C(=O)— (x-3),
=N—N=N— (x-4),
=N—CR⁶=N— (x-5),
=CR⁶—CR⁷=CR⁸— (x-6),
=CR⁶—N=CR⁷— (x-7),
=CR⁶—NH—C(=O)— (x-8), or
=CR⁶—N=N— (x-9);
wherein each $R^6$, $R^7$ and $R^8$ are independently hydrogen, $C_{1-4}$alkyl, hydroxy, $C_{1-4}$alkyloxy, aryloxy, $C_{1-4}$alkyloxycarbonyl, hydroxy$C_{1-6}$alkyl, $C_{1-4}$alkyloxy$C_{1-4}$alkyl, mono- or di($C_{1-6}$alkyl)amino$C_{1-4}$alkyl, cyano, amino, thio, $C_{1-4}$alkylthio, arylthio or aryl;
>Y¹—Y² is a trivalent radical of formula
>CH—CHR⁹— (y-1),
>C=N— (y-2),
>CH—NR⁹— (y-3), or
>C=CR⁹— (y-4);
wherein each $R^9$ independently is hydrogen, halo, halocarbonyl, aminocarbonyl, hydroxy$C_{1-4}$alkyl, cyano, carboxyl, $C_{1-4}$alkyl, $C_{1-4}$alkyloxy, $C_{1-4}$alkyloxy$C_{1-4}$alkyl, $C_{1-4}$alkyloxycarbonyl, mono- or di($C_{1-6}$alkyl)amino, mono- or di($C_{1-4}$alkyl)amino$C_{1-4}$alkyl, or aryl;
r and s are each independently 0, 1, 2, 3, 4 or 5;
t is 0, 1, 2 or 3;
each $R^1$ and $R^2$ are independently hydroxy, halo, cyano, $C_{1-6}$alkyl, trihalomethyl, trihalomethoxy, $C_{2-6}$alkenyl, $C_{1-6}$alkyloxy, hydroxy$C_{1-6}$alkyloxy, $C_{1-6}$alkylthio, $C_{1-6}$alkyloxy$C_{1-6}$alkyloxy, $C_{1-6}$alkyloxycarbonyl, amino$C_{1-6}$alkyloxy, mono- or di($C_{1-6}$alkyl)amino, mono- or di($C_{1-6}$alkyl)amino$C_{1-6}$alkyloxy, aryl, aryl$C_{1-6}$ alkyl, aryloxy or aryl$C_{1-6}$alkyloxy, hydroxycarbonyl, $C_{1-6}$alkyloxycarbonyl, aminocarbonyl, amino$C_{1-6}$ alkyl, mono- or di($C_{1-6}$alkyl)aminocarbonyl, or mono- or di($C_{1-6}$alkyl)amino$C_{1-6}$alkyl; or
two $R^1$ or $R^2$ substituents adjacent to one another on the phenyl ring independently form together a bivalent radical of formula
—O—CH₂—O— (a-1),
—O—CH₂—CH₂—O— (a-2),
—O=CH=CH— (a-3),
—O—CH₂—CH₂— (a-4),
—O—CH₂—CH₂—CH₂— (a-5), or
—CH=CH—CH=CH— (a-6);
$R^3$ is hydrogen, halo, $C_{1-6}$alkyl, cyano, halo$C_{1-6}$alkyl, hydroxy$C_{1-6}$alkyl, cyano$C_{1-6}$alkyl, amino$C_{1-6}$alkyl, $C_{1-6}$alkyloxy$C_{1-6}$alkyl, $C_{1-6}$alkylthioC$_{1-6}$alkyl, aminocarbonyl, $C_{1-6}$alkyl, hydroxycarbonyl, hydroxycarbonyl$C_{1-6}$alkyl, $C_{1-6}$alkyloxycarbonyl$C_{1-6}$alkyl, $C_{1-6}$alkylcarbonyl$C_{1-6}$alkyl, $C_{1-6}$alkyloxycarbonyl, aryl, aryl$C_{1-6}$alkyloxyC1-6 alkyl, mono- or di($C_{1-6}$alkyl)amino$C_{1-6}$alkyl; or a radical of formula
—O—R¹⁰ (b-1),
—S—R¹⁰ (b-2), or
—NR¹¹R¹² (b-3),
wherein $R^{10}$ is hydrogen, $C_{1-6}$alkyl, $C_{1-6}$alkylcarbonyl, aryl, aryl$C_{1-6}$alkyl, $C_{1-6}$alkyloxycarbonyl $C_{1-6}$alkyl, or a radical of formula -Alk—OR¹³ or -Alk—NR¹⁴R¹⁵;
$R^{11}$ is hydrogen, $C_{1-6}$alkyl, aryl or aryl$C_{1-6}$alkyl;

$R^{12}$ is hydrogen, $C_{1-6}$alkyl, aryl, hydroxy, amino, $C_{1-6}$alkyloxy, $C_{1-6}$alkylcarbonyl$C_{1-6}$alkyl, aryl$C_{1-6}$alkyl, $C_{1-6}$alkylcarbonylamino, mono- or di($C_{1-6}$alkyl)amino, $C_{1-6}$alkylcarbonyl, aminocarbonyl, arylcarbonyl, halo$C_{1-6}$alkylcarbonyl, aryl$C_{1-6}$alkylcarbonyl, $C_{1-6}$alkyloxycarbonyl, $C_{1-6}$alkyloxy$C_{1-6}$alkylcarbonyl, mono- or di($C_{1-6}$alkyl)aminocarbonyl wherein the alkyl moiety may optionally be substituted by one or more substituents independently selected from aryl or $C_{1-3}$alkyloxycarbonyl, aminocarbonylcarbonyl, mono- or di($C_{1-6}$alkyl)amino$C_{1-6}$alkylcarbonyl, or a radical of formula -Alk—OR¹³ or -Alk—NR¹⁴R¹⁵;
wherein Alk is $C_{1-6}$alkanediyl;
$R^{13}$ is hydrogen, $C_{1-6}$alkyl, $C_{1-6}$alkylcarbonyl, hydroxy$C_{1-6}$alkyl, aryl or aryl$C_{1-6}$alkyl;
$R^{14}$ is hydrogen, $C_{1-6}$alkyl, aryl or aryl$C_{1-6}$alkyl;
$R^{15}$ is hydrogen, $C_{1-6}$alkyl, $C_{1-6}$alkylcarbonyl, aryl or aryl$C_{1-6}$alkyl;
$R^4$ is a radical of formula

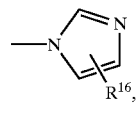

(c-1)

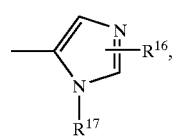

(c-2)

wherein $R^{16}$ is hydrogen, halo, aryl, $C_{1-6}$alkyl, hydroxy$C_{1-6}$alkyl, $C_{1-6}$alkyloxy$C_{1-6}$alkyl, $C_{1-6}$alkyloxy, $C_{1-6}$alkylthio, amino, mono- or di($C_{1-4}$alkyl)amino, hydroxycarbonyl, $C_{1-6}$alkyloxycarbonyl, $C_{1-6}$alkylthio$C_{1-6}$alkyl, $C_{1-6}$alkylS(O)$C_{1-6}$alkyl or $C_{1-6}$alkylS(O)₂$C_{1-6}$alkyl;
$R^{17}$ is hydrogen, $C_{1-6}$alkyl, $C_{1-6}$alkyloxy$C_{1-6}$alkyl, aryl$C_{1-6}$alkyl, trifluoromethyl or di($C_{1-4}$alkyl)aminosulfonyl;
$R^5$ is $C_{1-6}$alkyl, $C_{1-6}$alkyloxy or halo; aryl is phenyl, naphthalenyl or phenyl substituted with one or more substituents each independently selected from halo, $C_{1-6}$alkyl, $C_{1-6}$alkyloxy or trifluoromethyl; with the proviso that that when $R^{16}$ is bound to one of the nitrogen atoms in the imidazole ring of formula (c-1) or (c-2), $R^{16}$ is hydrogen, aryl, $C_{1-6}$alkyl, hydroxy$C_{1-6}$alkyl, $C_{1-6}$alkyloxy$C_{1-6}$alkyl, $C_1$ ₆alkyloxycarbonyl, $C_{1-6}$alkylS(O)$C_{1-6}$alkyl or $C_{1-6}$alkylS(O)₂$C_{1-6}$alkyl.

2. A compound according to claim 1 wherein each $R^1$ and $R^2$ are independently hydroxy, halo, cyano, $C_{1-6}$alkyl, trihalomethyl, trihalomethoxy, $C_{2-6}$alkenyl, $C_{1-6}$alkyloxy, hydroxy$C_{1-6}$alkyloxy, $C_{1-6}$alkylthio, $C_{1-6}$alkyloxy$C_{1-6}$alkyloxy, $C_{1-6}$alkyloxycarbonyl, amino$C_{1-6}$alkyloxy, mono- or di($C_{1-6}$alkyl)amino, mono- or di($C_{1-6}$alkyl)amino$C_{1-6}$alkyloxy, aryl, aryl$C_{1-6}$alkyl, aryloxy or aryl$C_{1-6}$alkyloxy, hydroxycarbonyl, or $C_{1-6}$alkyloxycarbonyl; or
two $R^1$ or $R^2$ substituents adjacent to one another on the phenyl ring independently form together a bivalent radical of formula
—O—CH₂—O— (a-1),
—O—CH₂—CH₂—O— (a-2),
—O=CH=CH— (a-3),
—O—CH₂—CH₂— (a-4),
—O—CH₂—CH₂—CH₂— (a-5), or
—CH=CH—CH=CH— (a-6);

$R^{17}$ is hydrogen, $C_{1-6}$alkyl, trifluoromethyl or di($C_{1-6}$alkyl)aminosulfonyl;

with the proviso that that when $R^{16}$ is bound to one of the nitrogen atoms in the imidazole ring of formula (c-1), $R^{16}$ is hydrogen, aryl, $C_{1-6}$alkyl, hydroxy$C_{1-6}$alkyl, $C_{1-6}$alkyloxy$C_{1-6}$alkyl, $C_{1-6}$alkyloxycarbonyl, $C_{1-6}$alkylS(O)$C_{1-6}$alkyl or $C_{1-6}$alkylS(O)$_2C_{1-6}$alkyl.

3. A compound according to claim 1 wherein =$X^1$—$X^2$—$X^3$ is a trivalent radical of formula (x-1), (x-2), (x-3), (x-4) or (x-9) wherein each $R^6$ independently is hydrogen, $C_{1-4}$alkyl, $C_{1-6}$alkyloxycarbonyl, amino or aryl and $R^7$ is hydrogen; >$Y^1$—$Y^2$— is a trivalent radical of formula (y-1), (y-2), (y-3), or (y-4) wherein each $R^9$ independently is hydrogen, halo, carboxyl, $C_{1-4}$alkyl or $C_{1-4}$alkyloxycarbonyl; r is 0, 1 or 2; s is 0 or 1; t is 0; $R^1$ is halo, $C_{1-6}$alkyl or two $R^1$ substituents ortho to one another on the phenyl ring independently form together a bivalent radical of formula (a-1); $R^2$ is halo; $R^3$ is halo or a radical of formula (b-1) or (b-3) wherein $R^{10}$ is hydrogen or a radical of formula -Alk- $OR^{13}$, $R^{11}$ is hydrogen, $R^{12}$ is hydrogen, $C_{1-6}$alkyl, $C_{1-6}$alkylcarbonyl, hydroxy, $C_{1-6}$alkyloxy or mono- or di($C_{1-6}$alkyl)amino$C_{1-6}$alkylcarbonyl, Alk is $C_{1-6}$alkanediyl and $R^{13}$ is hydrogen; $R^4$ is a radical of formula (c-1) or (c-2) wherein $R^{16}$ is hydrogen, halo or mono- or di($C_{1-4}$alkyl)amino; $R^{17}$ is hydrogen or $C_{1-6}$alkyl; aryl is phenyl.

4. A compound according to claim 1 wherein =$X^1$—$X^2$—$X^3$ is a trivalent radical of formula (x-1), >$Y^1$—$Y^2$ is a trivalent radical of formula (y-4), r is 0 or 1, s is 1, t is 0, R3 is 3-chloro, $R^2$ is 4-chloro or 4-fluoro, $R^3$ is hydrogen or a radical of formula (b-1) or (b-3), $R^4$ is a radical of formula (c-1) or (c-2), $R^6$ is hydrogen, $R^7$ is hydrogen, $R^9$ is hydrogen, $R^{10}$ is hydrogen, $R^{11}$ is hydrogen and $R^{12}$ is hydrogen.

5. A compound according to claim 1 wherein =$X^1$—$X^2$—$X^3$ is a trivalent radical of formula (x-2) or (x-3), >$Y^1$—$Y^2$ is a trivalent radical of formula (y-2), (y-3) or (y-4), r and s are 1, t is 0, $R^1$ is 3-chloro or 3-methyl, $R^2$ is 4-chloro, $R^3$ is a radical of formula (b-1) or (b-3), $R^4$ is a radical of formula (c-2), $R^6$ is $C_{1-4}$alkyl, $R^9$ is hydrogen, $R^{10}$ and $R^{11}$ are hydrogen and $R^{12}$ is hydrogen or hydroxy.

6. A compound according to claim 1 selected from:
7-[(4-fluorophenyl)(1H-imidazol-1-yl)methyl]-5-phenylimidazo[1,2-a]quinoline;
α-(4-chlorophenyl)-α-(1-methyl-1H-imidazol-5-yl)-5-phenylimidazo[1,2-a]quinoline-7-methanol; 5-(3-chlorophenyl)-α-(4-chlorophenyl)-α-(1-methyl-1H-imidazol-5-yl)-imidazol[1,2-a]quinoline-7-methanol; 5-(3-chlorophenyl)-α-(4-chlorophenyl)-α-(1-methyl-1H-imidazol-5-yl)imidazol[1,2-a]quinoline-7-methanamine; 5-(3-chlorophenyl)-α-(4-chlorophenyl)-α-(1-methyl-1H-imidazol-5-yl)tetrazolo[1,5-a]quinoline-7-methanamine; 5-(3-chlorophenyl)-α-(4-chlorophenyl)-1-methyl-α-(1-methyl-1H-imidazol-5-yl)-1,2,4-triazolo[4,3-a]quinoline-7-methanol; 5-(3-chlorophenyl)-α-(4-chlorophenyl)-α-($_1$-methyl-1H-imidazol-5-yl)tetrazolo[1,5-a]quinoline-7-methanamine; 5-(3-chlorophenyl)-α-(4-chlorophenyl)-α-(1-methyl-1H-imidazol-5-yl)tetrazolo[1,5-a]quinazoline-7-methanol; 5-(3-chlorophenyl)-α-(4-chlorophenyl)-4,5-dihydro-α-(1-methyl-1H-imidazol-5-yl)quinazoline-7-methanol; 5-(3-chlorophenyl)-α-(4-chlorophenyl)-α-(1-methyl-1H-imidazol-5-yl)tetrazolo[1,5-a]quinazoline-7-methanamine; 5-(3-chlorophenyl)-α-(4-chlorophenyl)-N-hydroxy-α-(1-methyl-1H-imidazol-5-yl)tetrahydro[1,5-a]quinoline-7-methanamine; α-(4-chlorophenyl)-α-(1-methyl-1H-imidazol-5-yl)- 5-(3-methylphenyl)tetrazolo[1,5-a]quinoline-7-methanamine;

pharmaceutically acceptable acid addition salt or a stereochemically isomeric form thereof.

7. A pharmaceutical composition comprising a pharmaceutically acceptable carrier, and as active ingredient a therapeutically effective amount of a compound as defined in claim 1.

8. A process for preparing a pharmaceutical composition as claimed in claim 7 wherein said compound is mixed with a pharmaceutically acceptable carrier.

9. A process for preparing a compound as claimed in claim 1, wherein
a) when =$X^1$—$X^2$—$X^3$ is a trivalent radical of formula (x-1) and $R^6$ and $R^7$ are hydrogen, as represented by compounds of formula (I-1), the process comprises reacting an intermediate of formula (II) with a reagent of formula (III) or a functional derivative thereof, followed by an intramolecular cyclization;

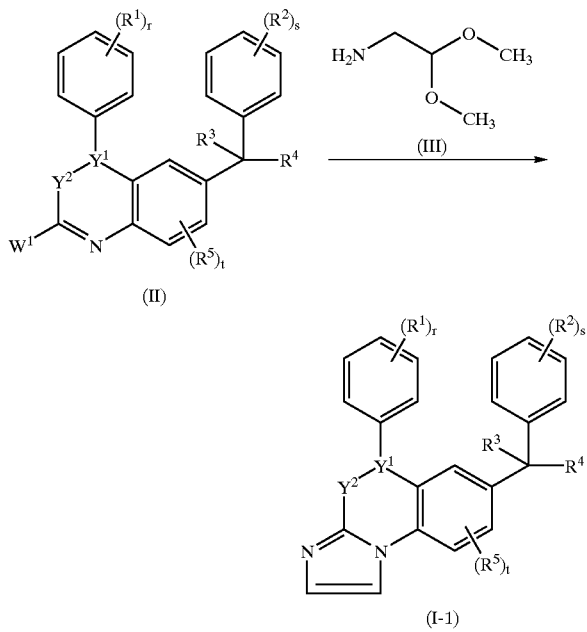

wherein $W^1$ is a leaving group;

b) when =$X^1$—$X^2$—$X^3$ is a trivalent radical of formula (x-1), >$Y^1$—$Y^2$ is a trivalent radical of formula (y-4), $R^9$ is hydrogen and at least one of $R^6$ and $R^7$ is not hydrogen, as represented by formula (I-1-a), the process comprises reacting a compound of formula (IV) with a reagent of formula (V), followed by an intramolecular cyclization;

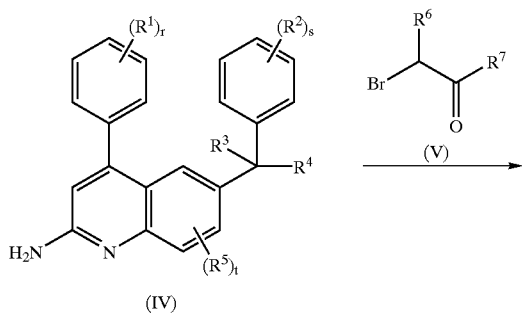

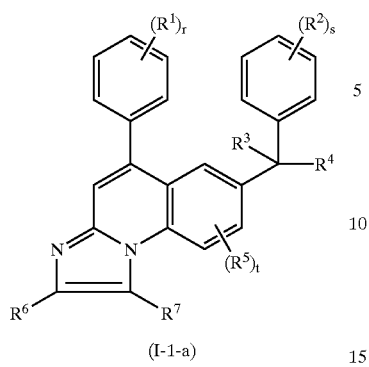

(I-1-a)

c) when =X¹—X²—X³ is a trivalent radical of formula (x-2), as represented by compounds of formula (I-2), the process comprises reacting a compound of formula (II) with an intermediate of formula (VI) or by reacting a compound of formula (VIII) with an intermediate of formula (VII) wherein the intermediate of formula (VII) is prepared by a process which comprises reacting an intermediate of formula (II) with $N_2H_4$;

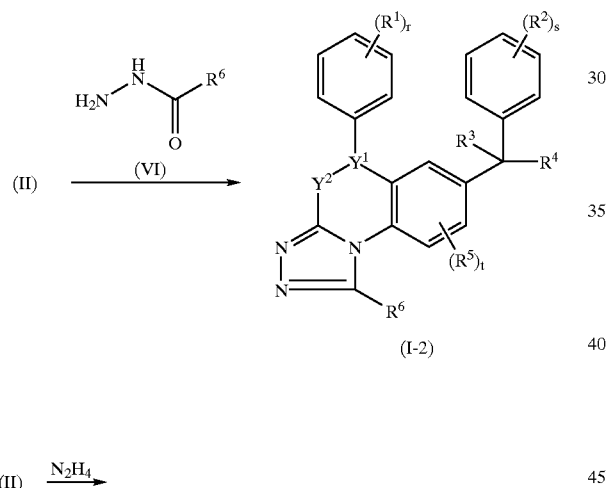

(I-2)

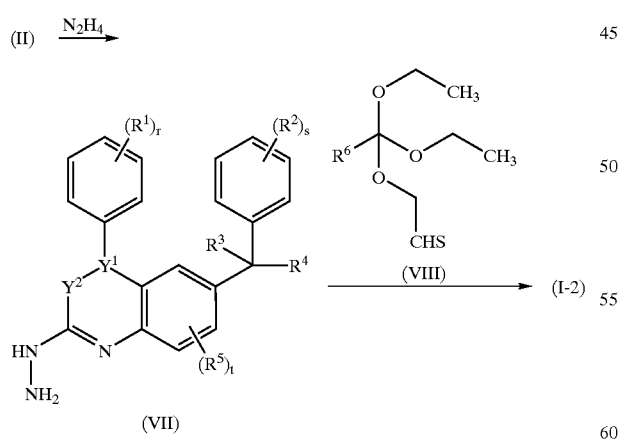

(VII)

d) when =X¹—X²—X³ is a trivalent radical of formula (x-2) and R⁶ is amino, as represented by compounds of formula (I-2-a), the process comprises reacting an intermediate of formula (VII) with BrCN;

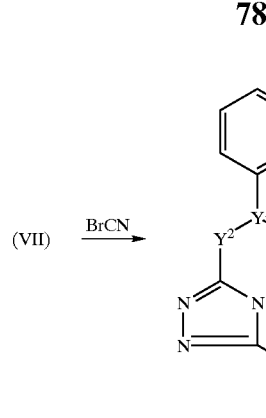

(I-2-a)

e) when =X¹—X²—X³ is a trivalent radical of formula (x-3), as represented by compounds of formula (I-3), the process comprises reacting an intermediate of formula (VII) with a compound of formula (IX) or by reacting a compound of formula (X) with an intermediate of formula (II);

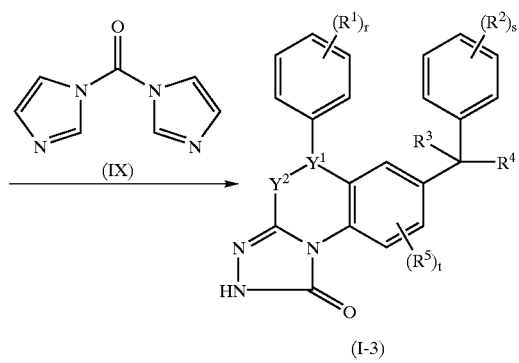

(I-3)

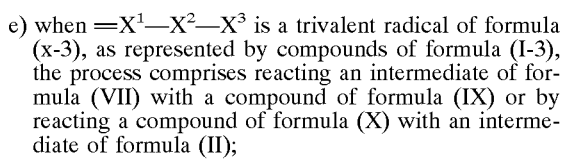

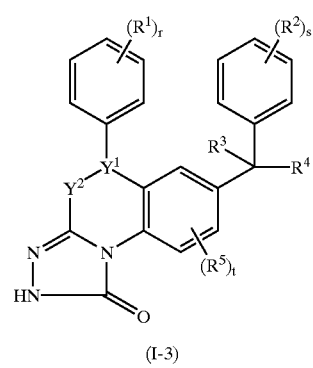

(I-3)

f) when =X¹—X²—X³ is a trivalent radical of formula (x-4), as represented by compounds of formula (I-4), the process comprises reacting an intermediate of formula (XI) with $NaN_3$;

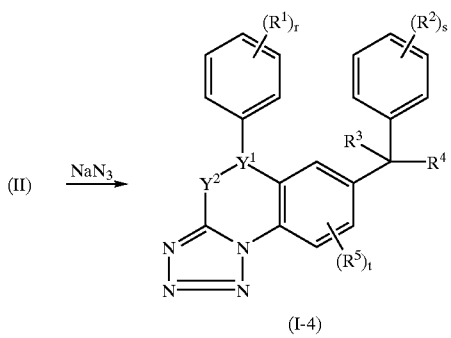

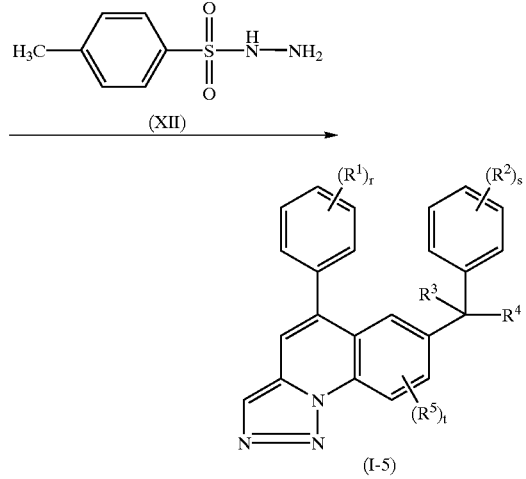

g) when $=X^1-X^2X^3$ is a trivalent radical of formula (x-9), $>Y^1-Y^2$ is a trivalent radical of formula (y-4) and $R^1$ is hydrogen, as represented by compounds of formula (I-5), the process comprises reacting an intermediate of formula (XI) with a compound of formula (XII) wherein the intermediate of formula (XI) is prepared by a process which comprises reacting an intermediate of formula (XIII) with $SeO_2$ and wherein the intermediate of formula (XIII) is prepared by a process which comprises reacting an intermediate of formula (XIV) with 2-propanone;

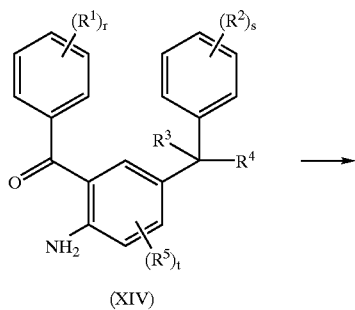

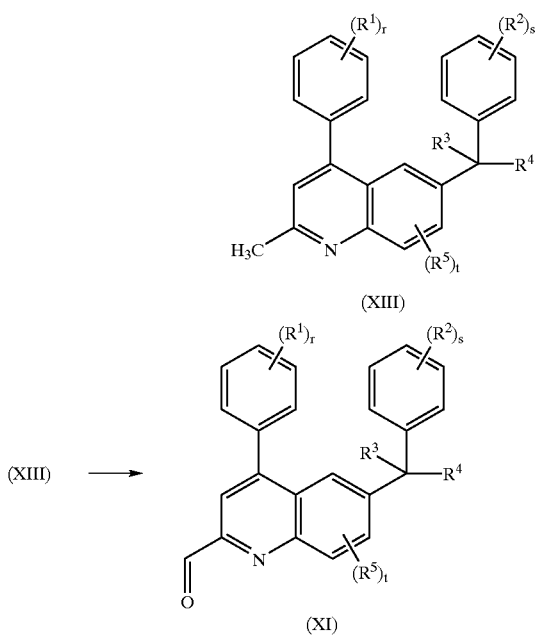

h) converting compounds of formula (I-6) wherein $>Y^1-Y^2$ is a trivalent radical of formula (y-2) or (y-4) to the corresponding compounds of formula (I-7) wherein $>Y^1-Y^2$ is a trivalent radical of formula (y-3) or (y-1) and $R^9$ is hydrogen by a process which comprises reacting compounds of formula (I-6) with $NaBH_4$ or $LiAlH_4$; or converting compounds of formula (I-7) to the corresponding compounds of formula (I-6) by oxidation with $MnO_2$;

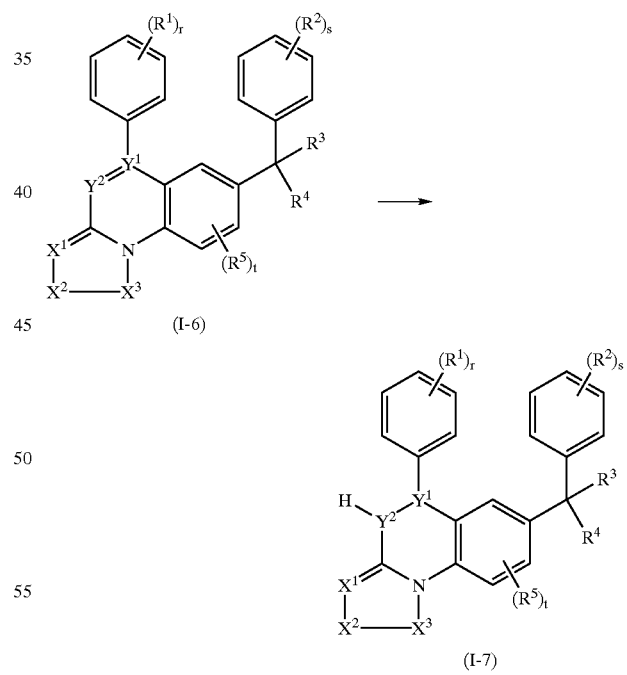

i) converting compounds of formula (I-7) to compounds of formula (I-7-a) wherein $>Y^1-Y^2$ is a trivalent radical of formula (y-3) or (y-1) and $R^9$ is other than hydrogen, by a process which comprises reacting these compounds of formula (I-7) with a reagent of formula $R^9$-$w^2$,

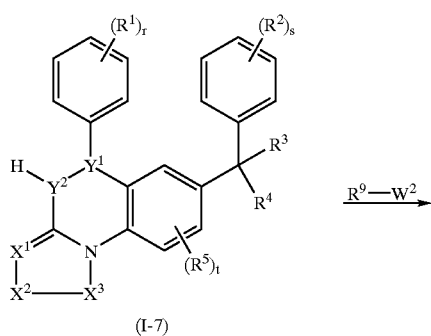

(I-7)

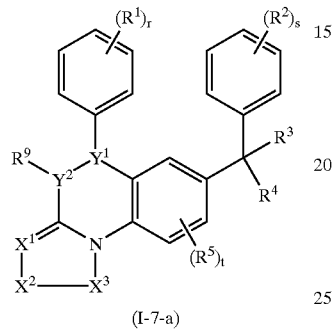

(I-7-a)

wherein W² is a leaving group;

j) converting compounds of formula (I-8) when R³ is a radical of formula (c-2) and R⁴ is hydroxy, to compounds of formula (I-8-a) wherein R⁴ is hydrogen, by a process which comprises stirring the compounds of formula (I-8) in acetic acid in the presence of formamide;

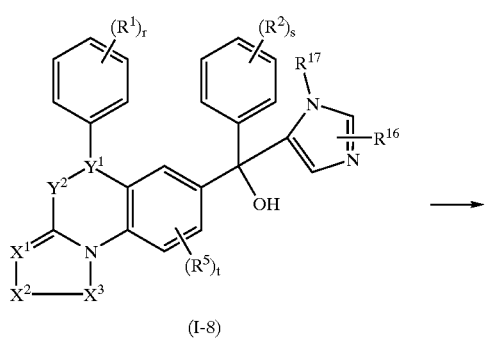

(I-8)

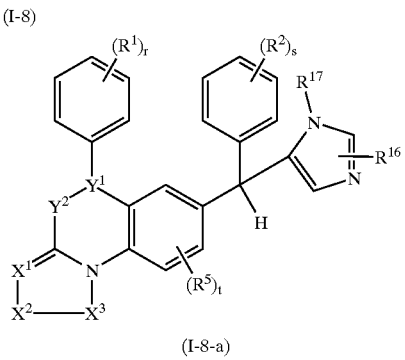

(I-8-a)

k) converting compounds of formula (I-8) to compounds of formula (I-8-b) wherein R⁴ is halo, by a process which comprises reacting the compounds of formula (I-8) with a halogenating agent; successively, treating the compounds of formula (I-8-b) with a reagent of formula H—NR¹¹R¹², to yield compounds of formula (I-8-c);

(I-8) →

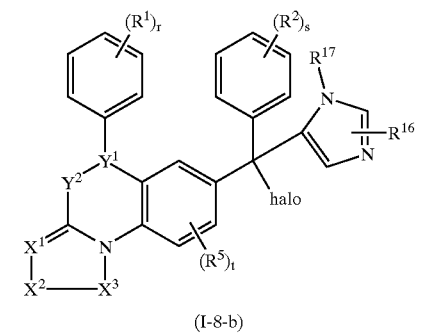

(I-8-b)

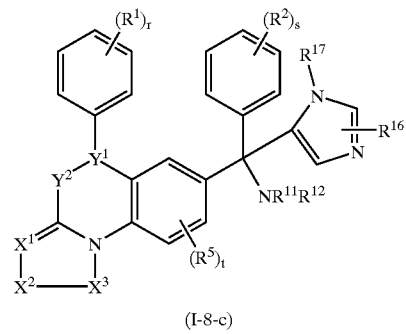

(I-8-c)

or l) interconverting a first compound of formula I to yield a second compound of formula I; or optionally converting a compound of formula (I) into a pharmaceutically acceptable acid addition salt, or converting an acid addition salt of a compound of formula (I) into a free base form with alkali; and, optionally, preparing stereochemically isomeric forms thereof.

* * * * *

UNITED STATES PATENT AND TRADEMARK OFFICE
CERTIFICATE OF CORRECTION

PATENT NO.  : 6,458,800 B1
DATED       : October 1, 2002
INVENTOR(S) : Angibaud et al.

It is certified that error appears in the above-identified patent and that said Letters Patent is hereby corrected as shown below:

Column 2,
Line 62, please delete "–O=CH=CH–" and insert -- –O–CH=CH– -- therefor.

Column 4,
Line 16, please delete "–O=CH=CH–" and insert -- –O–CH=CH– -- therefor.

Column 73,
Line 47, please delete "–O=CH=CH–" and insert -- –O–CH=CH– -- therefor.

Column 74,
Line 64, please delete "–O=CH=CH–" and insert -- –O–CH=CH– -- therefor.

Column 82,
Line 57, please insert
-- 10. A compound according to claim 6 wherein the compound is 5-(3-chlorophenyl)-α-(4-chlorophenyl)-α-(1-methyl-1$H$-imidazol-5-yl)tetrazolo[1,5-a]quinazoline-7-methanamine or a pharmaceutically acceptable acid addition salt or a stereochemically isomeric form thereof.

11. A pharmaceutical composition comprising a pharmaceutically acceptable carrier, and as active ingredient a therapeutically effective amount of a compound as defined in claim 10. --

Signed and Sealed this

Eighteenth Day of November, 2003

JAMES E. ROGAN
*Director of the United States Patent and Trademark Office*